(12) United States Patent
Collingwood et al.

(10) Patent No.: US 8,945,868 B2
(45) Date of Patent: Feb. 3, 2015

(54) METHODS AND COMPOSITIONS FOR MODIFICATION OF A HLA LOCUS

(75) Inventors: Trevor Collingwood, Novato, CA (US); Laurence J. N. Cooper, Austin, TX (US); Philip D. Gregory, Orinda, CA (US); Michael C. Holmes, Oakland, CA (US); Jeffrey C. Miller, San Leandro, CA (US); Edward J. Rebar, San Francisco, CA (US); Andreas Reik, Vallejo, CA (US); Fyodor Urnov, Richmond, CA (US)

(73) Assignees: Sangamo BioSciences, Inc., Richmond, CA (US); Board of Regents, The University of Texas Systems, Austin, TX (US)

( * ) Notice: Subject to any disclaimer, the term of this patent is extended or adjusted under 35 U.S.C. 154(b) by 66 days.

(21) Appl. No.: 13/188,417

(22) Filed: Jul. 21, 2011

(65) Prior Publication Data

US 2012/0060230 A1    Mar. 8, 2012

Related U.S. Application Data

(60) Provisional application No. 61/400,009, filed on Jul. 21, 2010, provisional application No. 61/404,685, filed on Oct. 6, 2010.

(51) Int. Cl.
 *C12N 15/00* (2006.01)
 *C12P 21/00* (2006.01)
 *C07K 14/74* (2006.01)

(52) U.S. Cl.
 CPC ....... *C07K 14/70539* (2013.01); *C07K 2319/81* (2013.01)
 USPC ....... 435/69.1; 435/252.3; 435/440; 435/455; 530/350

(58) Field of Classification Search
 CPC .............................. C12N 2501/40; C12N 1/00
 USPC ...................... 435/69.1, 252.3, 440, 455, 350
 See application file for complete search history.

(56) References Cited

U.S. PATENT DOCUMENTS

| | | | |
|---|---|---|---|
| 5,356,802 A | 10/1994 | Chandrasegaran |
| 5,436,150 A | 7/1995 | Chandrasegaran |
| 5,487,994 A | 1/1996 | Chandrasegaran |
| 5,789,538 A | 8/1998 | Rebar et al. |
| 5,925,523 A | 7/1999 | Dove et al. |
| 6,007,988 A | 12/1999 | Choo et al. |
| 6,013,453 A | 1/2000 | Choo et al. |
| 6,140,081 A | 10/2000 | Barbas |
| 6,140,466 A | 10/2000 | Barbas, III et al. |
| 6,200,759 B1 | 3/2001 | Dove et al. |
| 6,242,568 B1 | 6/2001 | Barbas, III et al. |
| 6,410,248 B1 | 6/2002 | Greisman et al. |
| 6,453,242 B1 | 9/2002 | Eisenberg et al. |
| 6,479,626 B1 | 11/2002 | Kim et al. |
| 6,503,717 B2 | 1/2003 | Case et al. |
| 6,534,261 B1 | 3/2003 | Cox, III et al. |
| 6,599,692 B1 | 7/2003 | Case et al. |
| 6,607,882 B1 | 8/2003 | Cox, III et al. |
| 6,689,558 B2 | 2/2004 | Case |
| 6,794,136 B1 | 9/2004 | Eisenberg et al. |
| 6,824,978 B1 | 11/2004 | Cox, III et al. |
| 6,903,185 B2 | 6/2005 | Kim et al. |
| 6,933,113 B2 | 8/2005 | Case et al. |
| 6,979,539 B2 | 12/2005 | Cox, III et al. |
| 7,013,219 B2 | 3/2006 | Case et al. |
| 7,030,215 B2 | 4/2006 | Liu et al. |
| 7,067,317 B2 | 6/2006 | Rebar et al. |
| 7,070,934 B2 | 7/2006 | Cox, III et al. |
| 7,153,949 B2 | 12/2006 | Kim et al. |
| 7,163,824 B2 | 1/2007 | Cox, III et al. |
| 7,253,273 B2 | 8/2007 | Collingwood |
| 7,262,054 B2 | 8/2007 | Jamieson et al. |
| 7,361,635 B2 | 4/2008 | Miller et al. |
| 2003/0232410 A1 | 12/2003 | Liljedahl et al. |
| 2005/0026157 A1 | 2/2005 | Baltimore et al. |
| 2005/0064474 A1 | 3/2005 | Urnov et al. |
| 2005/0208489 A1 | 9/2005 | Carroll et al. |
| 2005/0267061 A1 | 12/2005 | Martin |
| 2006/0063231 A1 | 3/2006 | Li et al. |
| 2006/0188987 A1 | 8/2006 | Guschin et al. |
| 2007/0218528 A1 | 9/2007 | Miller et al. |
| 2008/0015164 A1 | 1/2008 | Collingwood |
| 2008/0131962 A1 | 6/2008 | Miller et al. |
| 2008/0159996 A1 | 7/2008 | Ando et al. |
| 2008/0299580 A1* | 12/2008 | DeKelver et al. ................. 435/6 |
| 2009/0068164 A1 | 3/2009 | Segal et al. |

(Continued)

FOREIGN PATENT DOCUMENTS

| GB | 2338237 | 12/1999 |
|---|---|---|
| WO | WO 95/19431 A1 | 7/1995 |

(Continued)

OTHER PUBLICATIONS

Greisman HA etal., Science. Jan. 31, 1997;275(5300):657-61.A general strategy for selecting high-affinity zinc finger proteins for diverse DNA target sites.*
Voet, Biochemistry John Wiley and Sons, 1990, pp. 126-128.*
Ngo, J. et al., "Computational Complexity, Protein Structure Prediction, and the Levinthal Paradox", 1994, The Protein Folding Problem and Tertiary Structure Prediction, Merz et al. (eds.), Birkhauser Boston: Boston, MA, pp. 433-440 and 492-495.*
Rudinger, J., "Characteristics of the amino acids as components of a peptide hormone sequence",in Peptide Hormones, University Park Press: Baltimore, MD, pp. 1-7, 1976.*
Tan et al Proc Natl Acad Sci U S A. Oct. 14, 2003;100(21):11997-2002. Epub Sep. 26, 2003. Zinc-finger protein-targeted gene regulation: genomewide single-gene specificity.*
Beerli, et al., "Engineering Polydactyl Zinc-Finger Transcription Factors," *Nature Biotechnol.* 20:135-141 (2002).

(Continued)

*Primary Examiner* — Maria Leavitt
(74) *Attorney, Agent, or Firm* — Dahna S. Pasternak; Pasternak Patent Law

(57) ABSTRACT

Disclosed herein are methods and compositions for modulating the expression of a HLA locus or for selectively deleting or manipulating a HLA locus or HLA regulator.

9 Claims, 20 Drawing Sheets

(56) References Cited

U.S. PATENT DOCUMENTS

| | | |
|---|---|---|
| 2009/0258363 A1 | 10/2009 | Gregory et al. |
| 2011/0129898 A1 | 6/2011 | Doyon |
| 2011/0145940 A1 | 6/2011 | Voytas et al. |
| 2011/0158957 A1 | 6/2011 | Bonini |
| 2011/0201055 A1 | 8/2011 | Doyon |
| 2011/0287512 A1 | 11/2011 | Paschon |

FOREIGN PATENT DOCUMENTS

| | | |
|---|---|---|
| WO | WO 96/06166 A1 | 2/1996 |
| WO | WO 98/37186 A1 | 8/1998 |
| WO | WO 98/53057 A1 | 11/1998 |
| WO | WO 98/53058 A1 | 11/1998 |
| WO | WO 98/53059 A1 | 11/1998 |
| WO | WO 98/53060 A1 | 11/1998 |
| WO | WO 98/54311 A1 | 12/1998 |
| WO | WO 00/27878 A1 | 5/2000 |
| WO | WO 01/60970 A2 | 8/2001 |
| WO | WO 01/88197 A2 | 11/2001 |
| WO | WO 02/16536 A1 | 2/2002 |
| WO | WO 02/077227 A2 | 10/2002 |
| WO | WO 02/099084 A2 | 12/2002 |
| WO | WO 03/016496 A2 | 2/2003 |
| WO | WO2005/100392 | 10/2005 |
| WO | WO 2007/014275 A2 | 2/2007 |
| WO | WO 2007/129093 A2 | 11/2007 |
| WO | WO 2009/042163 A2 | 4/2009 |
| WO | WO 2011/146121 A1 | 11/2011 |

OTHER PUBLICATIONS

Bitinaite, et al., "FokI Dimerization Is Required for DNA Cleavage," *PNAS* 95(18):10570-10575 (1998).
Boch, et al., "Breaking the Code of DNA Binding Specificity of TAL-Type III Effectors," *Science* 326(5959):1509-1512 (2009).
Choo, et al., "Advances in Zinc Finger Engineering," *Curr. Opin. Struct. Biol.* 10:411-416 (2000).
Cohen, et al., "In Vivo Expression of MHC Class I Genes Depends on the Presence of a Downstream Barrier Element," *PLoS ONE* 4(8):e6748 (2009).
Davies, et al., "Combining CD19 Redirection and Alloanergization to Generate Tumor-Specific Human T Cells for Allogeneic Cell Therapy of B-Cell Malignancies," *Cancer Res.* 70(10):3915-3924 (2010).
Fehling, et al., "MHC Class I Expression in Mice Lacking the Proteasome Subunit LMP-7," *Science* 265(5176):1234-1237 (1994).
Garbi, et al., "Impaired Immune Responses and Altered Peptide Repertoire in Tapasin-Deficient Mice," *Nat. Immunol.* 1: 234-238 (2000).
Grandea III, et al., "Impaired Assembly Yet Normal Trafficking of MHC Class I Molecules in Tapasin Mutant Mice," *Immunity* 13(2):213-222 (2000).
Heuer, et al., "Repeat Domain Diversity of AVRBS3-Like Genes in Ralstonia Solanacearum Strains and Association With Host Preferences in the Field," *Appl. Environ. Microbiol.* 73(13):4379-4384 (2007).
Isalan, et al., "A Rapid, Generally Applicable Method to Engineer Zinc Fingers Illustrated by Targeting the HIV-1 Promoter," *Nature Biotechnology* 19(7):656-660 (2001).
Kageshita, et al., "Down-Regulation of HLA Class I Antigen-Processing Molecules in Malignant Melanoma," *Am. Jour. Pathol.* 154(3): 745-754 (1999).
Kim, et al., "Chimeric Restriction Endonuclease," *PNAS* 91(3):883-887 (1994).
Kim, et al., "Insertion and Deletion Mutants of FokI Restriction Endonuclease," *J. Biol. Chem.* 269(50):31978-31982 (1994).
Kim, et al., "Hybrid Restriction Enzymes: Zinc Finger Fusions to FOK I Cleavage Domain," *PNAS* 93(3):1156-1160 (1996).
Leibundgut-Landmann, et al., "Mini Review: Specificity and Expression of CIITA, The Master Regulator of MHC Class II Genes," *Eur.J.Immunol.* 34:1513-1525 (2004).
Li, et al., "Functional Domains in FOK I Restriction Endonuclease," *PNAS* 89(10):4275-4279 (1992).
Li, et al., "Alteration of the Cleavage Distance of FOK I Restriction Endonuclease by Insertion Mutagenesis," *PNAS* 90(7):2764-2768 (1993).
Moscou, et al., "A Simple Cipher Governs DNA Recognition by TAL Effectors," *Science* 326(5959):1501 (2009).
Pabo, et al., "Design and Selection of Novel CYS2HIS2 Zinc Finger Proteins," *Ann. Rev. Biochem.* 70:313-340 (2001).
Perez, et al., "Establishment of HIV-1 Resistance in CD4+ T Cells by Genome Editing Using Zinc-Finger Nucleases," *Nat. Biotechnol.* 26(7):808-816.
Segal, et al., "Custom DNA-Binding Proteins Come of Age: Polydactyl Zinc-Finger Proteins," *Curr. Opin. Biotechnol.* 12(6):632-637 (2001).
Urnov, et al., "Highly Efficient Endogenous Human Gene Correction Using Designed Zinc-Finger Nucleases," *Nature* 435(7042):646-651 (2005).
Villard, et al., "A Functionally Essential Domain of RFX5 Mediates Activation of Major Histocompatibility Complex Class II Promoters by Promoting Cooperative Binding Between RFX and NF-Y," *Mol. Cell. Biol.* 20(10):3364-3376 (2000).
Zhu, et al., "Overexpression of MIR-152 Leads to Reduced Expression of Human Leukocyte Antigen-G and Increased Natural Killer Cell Mediated Cytolysis in JEG-3 Cells," *Am. J. Obstet. & Gynecol.* 202(6):592 (2010).
Andrew C. Jamieson et al; "Drug Discovery With Engineered Zinc-Finger Proteins"; Nature Publishing Group; Nature Reviews Drug Discovery; vol. 2; May 2003; pp. 361-369.
Myriam L'Haridon et al; "Transcriptional Regulation of the MHC Class I HLA-A11 Promoter by the Zinc Finger Protein ZFX"; Nucleic Acids Research; 1996; vol. 24, No. 10; pp. 1928-1935.
Thomas Scholl et al; "A Zinc Finger Protein That Represses Transcription of the Human MHC Class II Gene, DPA1,2"; The American Association of Immunologists; 1996; vol. 156; pp. 1448-1457.
Hiroki Torikai et al; "Toward Eliminating HLA Class I Expression to Generate Universal Cells From Allogeneic Donors"; Blood; Aug. 22, 2013; vol. 122; No. 8; pp. 1341-1350.

\* cited by examiner

Figure 1- HLA Class I and Class II gene clusters

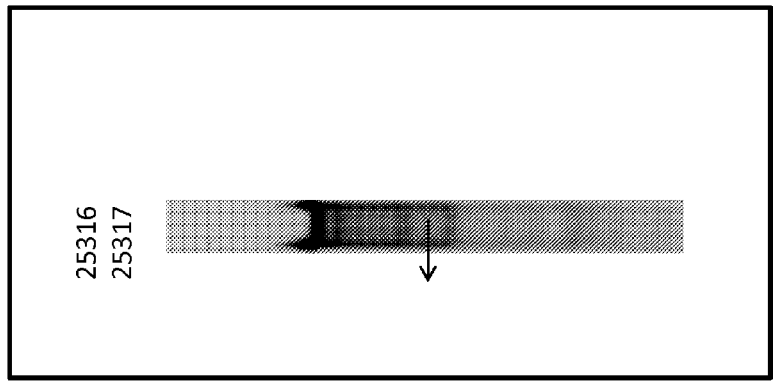
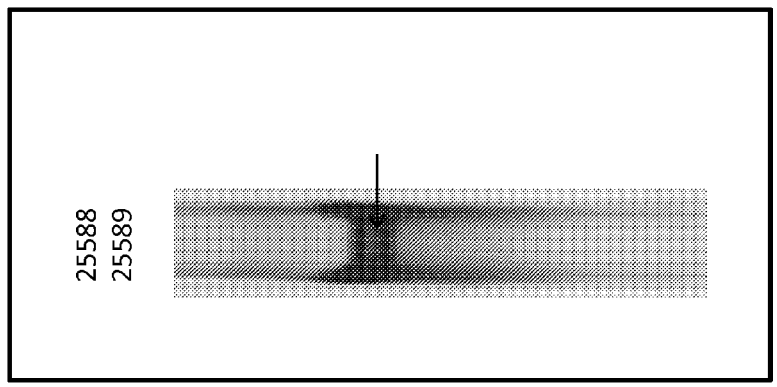
Figure 7

Figure 8
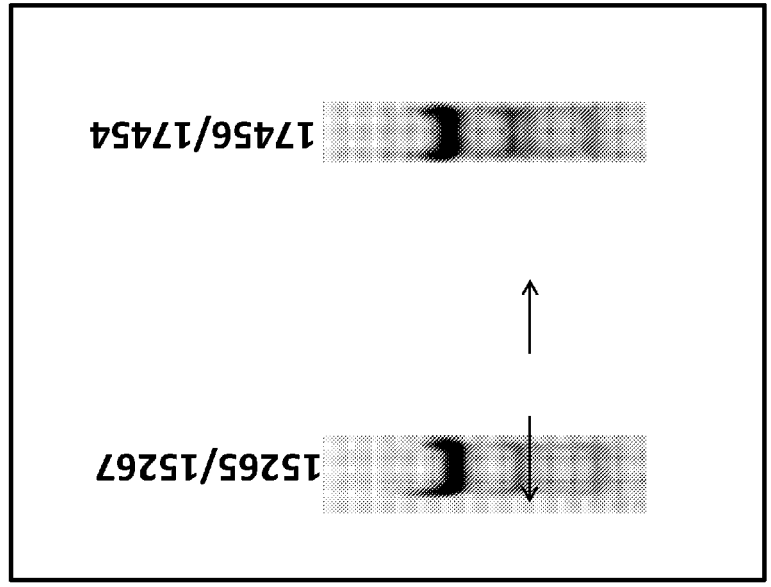
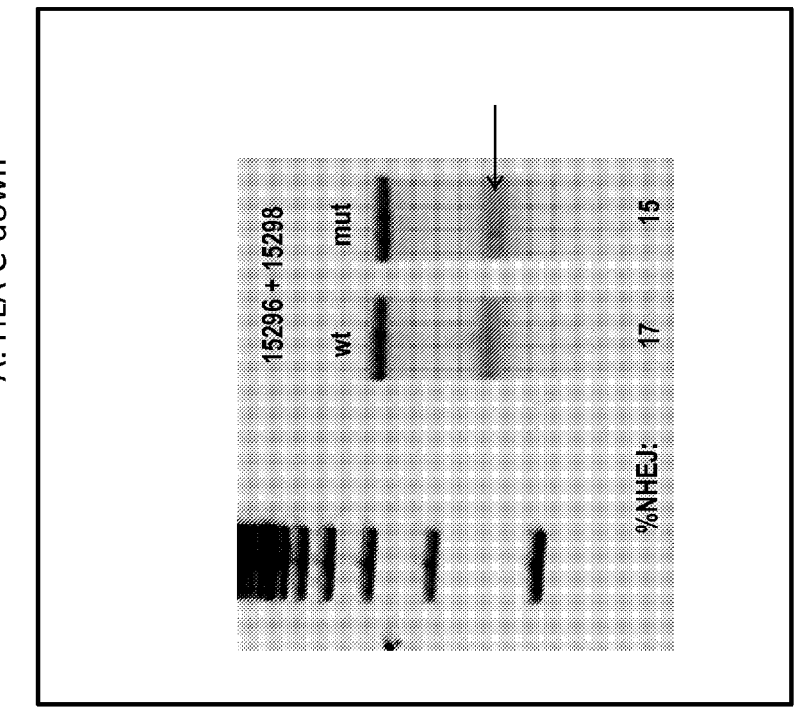

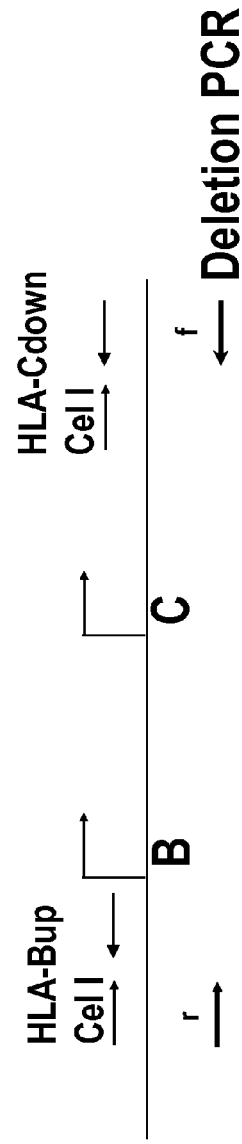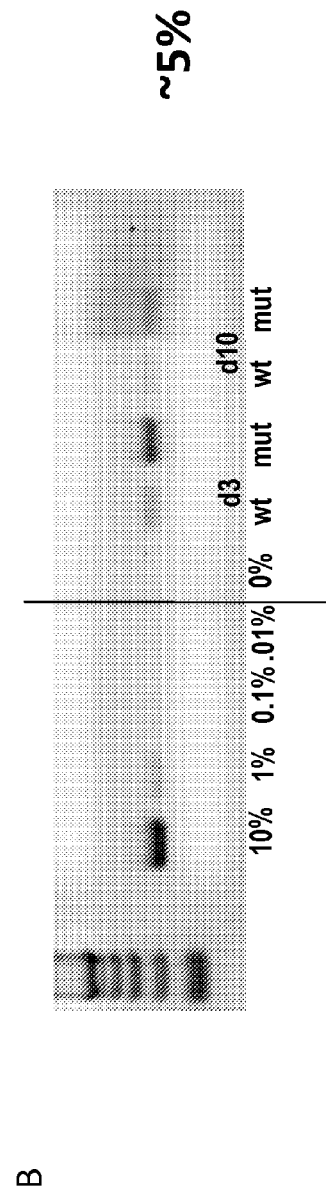
Figure 9

SEQUENCE LISTING

```
<160> NUMBER OF SEQ ID NOS: 141

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gln Ser Ser His Leu Thr Arg
1               5

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Arg Ser Asp His Leu Thr Thr
1               5

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Arg Ser Asp Thr Leu Ser Gln
1               5
```

```
<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Ser Ala Asp Leu Ser Arg
1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gln Ser Ser Asp Leu Ser Arg
1               5

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Arg Ser Asp Ala Leu Thr Gln
1               5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gln Lys Thr His Leu Ala Lys
1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Arg Ser Asp Thr Leu Ser Asn
1               5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9
```

```
Arg Lys Asp Val Arg Ile Thr
1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Arg Ser Asp His Leu Ser Thr
1               5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Asp Ser Ser Ala Arg Lys Lys
1               5

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gln Asn Ala His Arg Lys Thr
1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Arg Ser Asp Ser Leu Leu Arg
1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Arg Asn Asp Asp Arg Lys Lys
1               5

<210> SEQ ID NO 15
<211> LENGTH: 7
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 15

Asp Arg Ser His Leu Ser Arg
1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Arg Ser Asp Asp Leu Thr Arg
1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Asp Arg Ser Asp Leu Ser Arg
1               5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gln Ser Gly His Leu Ser Arg
1               5

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Asp Arg Ser Ala Leu Ser Arg
1               5

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gln Ser Ser Asp Leu Arg Arg
1               5
```

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Asp Arg Ser His Leu Ala Arg
1               5

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Arg Ser Asp Asp Leu Ser Lys
1               5

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ser Ser Glu Leu Leu Asn Glu
1               5

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Thr Ser Ser His Leu Ser Arg
1               5

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gln Ser Gly Asp Arg Asn Lys
1               5

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 26

Arg Ser Ala Asn Leu Ala Arg
1               5

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Arg Ser Asp Asn Leu Arg Glu
1               5

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gln Ser Gly Asp Leu Thr Arg
1               5

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Asp Gln Ser Thr Leu Arg Asn
1               5

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Asp Arg Ser Asn Leu Ser Arg
1               5

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Asp Ala Phe Thr Arg Thr Arg
1               5

<210> SEQ ID NO 32
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 32

Arg Ser Asp Asn Leu Ser Glu
1               5

<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Ala Ser Lys Thr Arg Lys Asn
1               5

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Thr Ser Gly Asn Leu Thr Arg
1               5

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Arg Ser Asp Ala Leu Ala Arg
1               5

<210> SEQ ID NO 36
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gln Ser Gly Asn Leu Ala Arg
1               5

<210> SEQ ID NO 37
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Thr Ser Gly His Leu Ser Arg
1               5
```

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Arg Ser Ala Asp Leu Thr Arg
1               5

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Gln Ser Ala Asp Arg Thr Lys
1               5

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Thr Ser Gly Ser Leu Ser Arg
1               5

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Arg Ser Asp Asn Leu Ser Ala
1               5

<210> SEQ ID NO 42
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Arg Ser Asp Asn Arg Thr Thr
1               5

<210> SEQ ID NO 43
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 43

Gln Arg Ser Asn Leu Val Arg
1               5

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Asp Arg Ser Ala Leu Ala Arg
1               5

<210> SEQ ID NO 45
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Arg Ser Asp His Leu Ser Ala
1               5

<210> SEQ ID NO 46
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Glu Ser Arg Tyr Leu Met Val
1               5

<210> SEQ ID NO 47
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Asp Asn Ala Asn Arg Thr Lys
1               5

<210> SEQ ID NO 48
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Arg Ser Asp Ala Leu Ser Thr
1               5

<210> SEQ ID NO 49
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Ala Ser Ser Asn Arg Lys Thr
1               5

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Arg Ser Ala Asn Leu Thr Arg
1               5

<210> SEQ ID NO 51
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Thr Ser Gly Ser Leu Thr Arg
1               5

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Arg Ser Asp Asn Leu Ser Gln
1               5

<210> SEQ ID NO 53
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Ala Ser Asn Asp Arg Lys Lys
1               5

<210> SEQ ID NO 54
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Arg Ser Asp Asn Leu Ser Arg
```

```
<210> SEQ ID NO 55
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Asp Asn Asn Ala Arg Ile Asn
1               5

<210> SEQ ID NO 56
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Arg Ser Asp Ser Leu Ser Val
1               5

<210> SEQ ID NO 57
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Gln Asn Gln His Arg Ile Asn
1               5

<210> SEQ ID NO 58
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Arg Ser Asp His Leu Ser Arg
1               5

<210> SEQ ID NO 59
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Asp Ser Ser Asp Arg Lys Lys
1               5

<210> SEQ ID NO 60
<211> LENGTH: 7
<212> TYPE: PRT
<213> ORGANISM: Artificial Sequence
<220> FEATURE:
<223> OTHER INFORMATION: Description of Artificial Sequence: Synthetic
```

```
                            peptide

<400> SEQUENCE: 60

Asp Arg Ser His Leu Thr Arg
1               5

<210> SEQ ID NO 61
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Arg Ser Asp Asn Leu Thr Thr
1               5

<210> SEQ ID NO 62
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Gln Ser Gly Ala Leu Val Ile
1               5

<210> SEQ ID NO 63
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Arg Ser Asp His Leu Ser Glu
1               5

<210> SEQ ID NO 64
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Arg Lys His Asp Arg Thr Lys
1               5

<210> SEQ ID NO 65
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Arg Ser Asp Asp Arg Lys Thr
1               5

<210> SEQ ID NO 66
```

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Arg Ser Asp Asn Leu Ser Thr
1               5

<210> SEQ ID NO 67
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Arg Ser Asp Val Leu Ser Ala
1               5

<210> SEQ ID NO 68
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Asp Arg Ser Asn Arg Ile Lys
1               5

<210> SEQ ID NO 69
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Arg Arg Glu Asp Leu Ile Thr
1               5

<210> SEQ ID NO 70
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Thr Ser Ser Asn Leu Ser Arg
1               5

<210> SEQ ID NO 71
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71
```

```
Lys Arg Cys Asn Leu Arg Cys
1               5
```

<210> SEQ ID NO 72
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

```
Gln Thr Thr His Arg Asn Arg
1               5
```

<210> SEQ ID NO 73
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

```
Gln Ser Ser Thr Arg Ala Arg
1               5
```

<210> SEQ ID NO 74
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

```
Arg Ser Asp Asn Leu Thr Arg
1               5
```

<210> SEQ ID NO 75
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

```
Gln Ser Ser Asp Leu Thr Arg
1               5
```

<210> SEQ ID NO 76
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

```
Arg Ser Asp Asn Leu Ala Arg
1               5
```

<210> SEQ ID NO 77
<211> LENGTH: 7
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 77

Gln Lys Val Asn Leu Met Ser
1               5

<210> SEQ ID NO 78
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Leu Ser Gln Asp Leu Asn Arg
1               5

<210> SEQ ID NO 79
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Arg Ser Asp Ser Leu Ser Ala
1               5

<210> SEQ ID NO 80
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Ser Ser Ser Asn Leu Thr Lys
1               5

<210> SEQ ID NO 81
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Arg Asn Arg Asp Arg Ile Thr
1               5

<210> SEQ ID NO 82
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Asn Ser Arg Asn Arg Lys Thr
1               5
```

```
<210> SEQ ID NO 83
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Arg Ser Asp Asp Leu Ser Arg
1               5

<210> SEQ ID NO 84
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Ala Arg Ser Thr Arg Thr Asn
1               5

<210> SEQ ID NO 85
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Arg Ser Asp His Leu Thr Gln
1               5

<210> SEQ ID NO 86
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Ala Ser Met Ala Leu Asn Glu
1               5

<210> SEQ ID NO 87
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Arg Ser Asp Val Leu Ser Glu
1               5

<210> SEQ ID NO 88
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88
```

```
Arg Asn Gln His Arg Lys Thr
1               5

<210> SEQ ID NO 89
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Arg Ser Ala Asp Arg Lys Asn
1               5

<210> SEQ ID NO 90
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Gln Trp Gly Thr Arg Tyr Arg
1               5

<210> SEQ ID NO 91
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Glu Arg Gly Thr Leu Ala Arg
1               5

<210> SEQ ID NO 92
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Trp Arg Ser Ser Leu Ala Ser
1               5

<210> SEQ ID NO 93
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

His Lys Trp Val Leu Arg Gln
1               5

<210> SEQ ID NO 94
<211> LENGTH: 7
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 94

Asp Arg Ser Asn Leu Thr Arg
1               5

<210> SEQ ID NO 95
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Gln Ser Gly Ser Leu Thr Arg
1               5

<210> SEQ ID NO 96
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Thr Ser Ser Asn Arg Lys Thr
1               5

<210> SEQ ID NO 97
<211> LENGTH: 28
<212> TYPE: DNA
<213> ORGANISM: Homo sapiens

<400> SEQUENCE: 97
gtatggctgc gacgtggggt cggacggg                                     28

<210> SEQ ID NO 98
<211> LENGTH: 28
<212> TYPE: DNA
<213> ORGANISM: Homo sapiens

<400> SEQUENCE: 98
ttatctggat ggtgtgagaa cctggccc                                     28

<210> SEQ ID NO 99
<211> LENGTH: 28
<212> TYPE: DNA
<213> ORGANISM: Homo sapiens

<400> SEQUENCE: 99
tcctctggac ggtgtgagaa cctggccc                                     28

<210> SEQ ID NO 100
<211> LENGTH: 28
<212> TYPE: DNA
<213> ORGANISM: Homo sapiens

<400> SEQUENCE: 100
atggagccgc gggcgccgtg gatagagc                                     28

<210> SEQ ID NO 101
```

```
<211> LENGTH: 28
<212> TYPE: DNA
<213> ORGANISM: Homo sapiens

<400> SEQUENCE: 101
ctggctcgcg gcgtcgctgt cgaaccgc                                              28

<210> SEQ ID NO 102
<211> LENGTH: 28
<212> TYPE: DNA
<213> ORGANISM: Homo sapiens

<400> SEQUENCE: 102
tccaggagct caggtcctcg ttcagggc                                              28

<210> SEQ ID NO 103
<211> LENGTH: 28
<212> TYPE: DNA
<213> ORGANISM: Homo sapiens

<400> SEQUENCE: 103
cggcggacac cgcggctcag atcaccca                                              28

<210> SEQ ID NO 104
<211> LENGTH: 28
<212> TYPE: DNA
<213> ORGANISM: Homo sapiens

<400> SEQUENCE: 104
aggtggatgc ccaggacgag ctttgagg                                              28

<210> SEQ ID NO 105
<211> LENGTH: 28
<212> TYPE: DNA
<213> ORGANISM: Homo sapiens

<400> SEQUENCE: 105
agggagcaga agcagcgcag cagcgcca                                              28

<210> SEQ ID NO 106
<211> LENGTH: 28
<212> TYPE: DNA
<213> ORGANISM: Homo sapiens

<400> SEQUENCE: 106
ctggaggtgg atgcccagga cgagcttt                                              28

<210> SEQ ID NO 107
<211> LENGTH: 28
<212> TYPE: DNA
<213> ORGANISM: Homo sapiens

<400> SEQUENCE: 107
gagcagaagc agcgcagcag cgccacct                                              28

<210> SEQ ID NO 108
<211> LENGTH: 28
<212> TYPE: DNA
<213> ORGANISM: Homo sapiens

<400> SEQUENCE: 108
cctcagtttc atgggattc aagggaac                                               28
```

```
<210> SEQ ID NO 109
<211> LENGTH: 28
<212> TYPE: DNA
<213> ORGANISM: Homo sapiens

<400> SEQUENCE: 109
cctaggaggt catgggcatt tgccatgc                                           28

<210> SEQ ID NO 110
<211> LENGTH: 28
<212> TYPE: DNA
<213> ORGANISM: Homo sapiens

<400> SEQUENCE: 110
tcgcggcgtc gctgtcgaac cgcacgaa                                           28

<210> SEQ ID NO 111
<211> LENGTH: 28
<212> TYPE: DNA
<213> ORGANISM: Homo sapiens

<400> SEQUENCE: 111
ccaagagggg agccgcggga gccgtggg                                           28

<210> SEQ ID NO 112
<211> LENGTH: 28
<212> TYPE: DNA
<213> ORGANISM: Homo sapiens

<400> SEQUENCE: 112
gaaataaggc atactggtat tactaatg                                           28

<210> SEQ ID NO 113
<211> LENGTH: 28
<212> TYPE: DNA
<213> ORGANISM: Homo sapiens

<400> SEQUENCE: 113
gaggagagca ggccgattac ctgaccca                                           28

<210> SEQ ID NO 114
<211> LENGTH: 28
<212> TYPE: DNA
<213> ORGANISM: Homo sapiens

<400> SEQUENCE: 114
tctcccaggg tggttcagtg gcagaatt                                           28

<210> SEQ ID NO 115
<211> LENGTH: 28
<212> TYPE: DNA
<213> ORGANISM: Homo sapiens

<400> SEQUENCE: 115
gcgggggaaa gagaggagga gagaagga                                           28

<210> SEQ ID NO 116
<211> LENGTH: 28
<212> TYPE: DNA
<213> ORGANISM: Homo sapiens

<400> SEQUENCE: 116
agaaggctgt gggctcctca gagaaaat                                           28
```

<210> SEQ ID NO 117
<211> LENGTH: 28
<212> TYPE: DNA
<213> ORGANISM: Homo sapiens

<400> SEQUENCE: 117
actctggggt agatggagag cagtacct                                          28

<210> SEQ ID NO 118
<211> LENGTH: 28
<212> TYPE: DNA
<213> ORGANISM: Homo sapiens

<400> SEQUENCE: 118
ttgcggatcc gggagcagct tttctcct                                          28

<210> SEQ ID NO 119
<211> LENGTH: 28
<212> TYPE: DNA
<213> ORGANISM: Homo sapiens

<400> SEQUENCE: 119
ttgattcgag acatggtgta ggtgaagc                                          28

<210> SEQ ID NO 120
<211> LENGTH: 28
<212> TYPE: DNA
<213> ORGANISM: Homo sapiens

<400> SEQUENCE: 120
ccacagccag agcctcagca ggagcctg                                          28

<210> SEQ ID NO 121
<211> LENGTH: 28
<212> TYPE: DNA
<213> ORGANISM: Homo sapiens

<400> SEQUENCE: 121
cgcaagaggc tggagaggct gaggactg                                          28

<210> SEQ ID NO 122
<211> LENGTH: 28
<212> TYPE: DNA
<213> ORGANISM: Homo sapiens

<400> SEQUENCE: 122
ctggatgggg cttggctgat ggtcagca                                          28

<210> SEQ ID NO 123
<211> LENGTH: 28
<212> TYPE: DNA
<213> ORGANISM: Homo sapiens

<400> SEQUENCE: 123
gcccgcgggc agttctgcgc gggggtca                                          28

<210> SEQ ID NO 124
<211> LENGTH: 28
<212> TYPE: DNA
<213> ORGANISM: Homo sapiens

<400> SEQUENCE: 124
gctcccaggc agcgggcggg aggctgga                                          28

<210> SEQ ID NO 125
<211> LENGTH: 28
<212> TYPE: DNA
<213> ORGANISM: Homo sapiens

<400> SEQUENCE: 125
ctactcgggc catcggcggc tgcctcgg                                    28

<210> SEQ ID NO 126
<211> LENGTH: 28
<212> TYPE: DNA
<213> ORGANISM: Homo sapiens

<400> SEQUENCE: 126
ttgatgtcag ggaagatctc tctgatga                                    28

<210> SEQ ID NO 127
<211> LENGTH: 28
<212> TYPE: DNA
<213> ORGANISM: Homo sapiens

<400> SEQUENCE: 127
gctcgaaggc ttggtggccg gggccagt                                    28

<210> SEQ ID NO 128
<211> LENGTH: 28
<212> TYPE: DNA
<213> ORGANISM: Homo sapiens

<400> SEQUENCE: 128
ttgttgctcc aggccacagc actgttgc                                    28

<210> SEQ ID NO 129
<211> LENGTH: 28
<212> TYPE: DNA
<213> ORGANISM: Homo sapiens

<400> SEQUENCE: 129
ctgactttgc atgtgcaaac gccttcaa                                    28

<210> SEQ ID NO 130
<211> LENGTH: 28
<212> TYPE: DNA
<213> ORGANISM: Homo sapiens

<400> SEQUENCE: 130
ccgtagaact ggacttgaca gcggaagt                                    28

<210> SEQ ID NO 131
<211> LENGTH: 28
<212> TYPE: DNA
<213> ORGANISM: Homo sapiens

<400> SEQUENCE: 131
tctcggagaa tgacgagtgg acccagga                                    28

<210> SEQ ID NO 132
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 132

Thr Gly Gly Gln Arg Pro
1               5

<210> SEQ ID NO 133
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Thr Gly Gln Lys Pro
1               5

<210> SEQ ID NO 134
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Thr Gly Ser Gln Lys Pro
1               5

<210> SEQ ID NO 135
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Arg Val Trp Asp Leu Pro Gly Val Leu Lys
1               5                   10

<210> SEQ ID NO 136
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Cys Ile Pro Pro Asp Ser Leu Leu Phe Pro Ala
1               5                   10

<210> SEQ ID NO 137
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137
gggctatatt gttgggtcag gtaatcggcc tgctctcctc attctcccag ggtggttcag      60
tggcagaatt ctg                                                        73

<210> SEQ ID NO 138
```

```
<211> LENGTH: 51
<212> TYPE: DNA
<213> ORGANISM: Homo sapiens

<400> SEQUENCE: 138
ctcctctctt tccccgcat tctcccaggg tggttcagtg gcagaattct g       51

<210> SEQ ID NO 139
<211> LENGTH: 59
<212> TYPE: DNA
<213> ORGANISM: Homo sapiens

<400> SEQUENCE: 139
gggctatatt gttgggtcag gtaatcggcc tgctctcctc atgaaataag gcatactgg    59

<210> SEQ ID NO 140
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Thr Gly Glu Lys Pro
1               5

<210> SEQ ID NO 141
<211> LENGTH: 9
<212> TYPE: PRT
<213> ORGANISM: Unknown
<220> FEATURE:
<223> OTHER INFORMATION: Description of Unknown: Naturally-occuring
      meganuclease recognition sequence

<400> SEQUENCE: 141

Leu Ala Gly Leu Ile Asp Ala Asp Gly
1               5
```

METHODS AND COMPOSITIONS FOR MODIFICATION OF A HLA LOCUS

CROSS-REFERENCE TO RELATED APPLICATIONS

The present application claims the benefit of U.S. Provisional Application No. 61/400,009, filed Jul. 21, 2010 and U.S. Provisional Applications No. 61/404,685, filed Oct. 6, 2010, the disclosures of which are hereby incorporated by reference in their entireties.

STATEMENT OF RIGHTS TO INVENTIONS MADE UNDER FEDERALLY SPONSORED RESEARCH

Not Applicable.

TECHNICAL FIELD

The present disclosure is in the fields of gene expression, genome engineering and gene therapy.

BACKGROUND

MHC antigens were first characterized as proteins that played a major role in transplantation reactions. Rejection is mediated by T cells reacting to the histocompatibility antigens on the surface of implanted tissues, and the largest group of these antigens is the major histocompatibility antigens (MHC). These proteins are expressed on the surface of all higher vertebrates and are called H-2 antigens in mice (for histocompatibility-2 antigens) and HLA antigens (for human leukocyte antigens) in human cells.

The MHC proteins serve a vital role in T cell stimulation. Antigen presenting cells (often dendritic cells) display peptides that are the degradation products of foreign proteins on the cell surface on the MHC. In the presence of a co-stimulatory signal, the T cell becomes activated, and will act on a target cell that also displays that same peptide/MHC complex. For example, a stimulated T helper cell will target a macrophage displaying an antigen in conjunction with its MHC, or a cytotoxic T cell (CTL) will act on a virally infected cell displaying foreign viral peptides.

MHC proteins are of two classes, I and II. The class I MHC proteins are heterodimers of two proteins, the α chain, which is a transmembrane protein encoded by the MHC1 gene, and the β2 microblogulin chain, which is a small extracellular protein that is encoded by a gene that does not lie within the MHC gene cluster. The α chain folds into three globular domains and when the β2 microglobulin chain is associated, the globular structure complex is similar to an antibody complex. The foreign peptides are presented on the two most N-terminal domains which are also the most variable. Class II MHC proteins are also heterodimers, but the heterodimers comprise two transmembrane proteins encoded by genes within the MHC complex. The class I MHC:antigen complex interacts with cytotoxic T cells while the class II MHC presents antigens to helper T cells. In addition, class I MHC proteins tend to be expressed in nearly all nucleated cells and platelets (and red blood cells in mice) while class II MHC protein are more selectively expressed. Typically, class II MHC proteins are expressed on B cells, some macrophage and monocytes, Langerhans cells, and dendritic cells.

The class I HLA gene cluster in humans comprises three major loci, B, C and A, as well as several minor loci. The class II HLA cluster also comprises three major loci, DP, DQ and DR, and both the class I and class II gene clusters are polymorphic, in that there are several different alleles of both the class I and II genes within the population. There are also several accessory proteins that play a role in HLA functioning as well. The Tap1 and Tap2 subunits are parts of the TAP transporter complex that is essential in loading peptide antigens on to the class I HLA complexes, and the LMP2 and LMP7 proteosome subunits play roles in the proteolytic degradation of antigens into peptides for display on the HLA. Reduction in LMP7 has been shown to reduce the amount of MHC class I at the cell surface, perhaps through a lack of stabilization (see Fehling et al (1999) Science 265:1234-1237). In addition to TAP and LMP, there is the tapasin gene, whose product forms a bridge between the TAP complex and the HLA class I chains and enhances peptide loading. Reduction in tapasin results in cells with impaired MHC class I assembly, reduced cell surface expression of the MHC class I and impaired immune responses (see Grandea et al (2000) Immunity vol 13:213-222 and Garbi et al (2000) Nat Immunol 1:234-238).

Regulation of class I expression is generally at the transcriptional level, and several stimuli such as viral infection etc. can cause a change in transcription. The class I genes are down-regulated in some specific tissues, and the source of this down-regulation seems to be within the promoter and 3' intergenic sequences (see Cohen et al (2009) PLos ONE 4(8): e6748). There is also evidence that microRNAs are capable of regulating some class I MHC genes (see Zhu et al, (2010) Am. J. Obstet Gynecol 202(6):592).

Regulation of class II MHC expression is dependent upon the activity of the MHCII enhanceosome complex. The enhanceosome components (one of the most highly studied components of the enhanceosome complex is the RFX5 gene product (see Villard et al (2000) MCB 20(10): 3364-3376)) are nearly universally expressed and expression of these components does not seem to control the tissue specific expression of MHC class II genes or their IFN-γ induced up-regulation. Instead, it appears that a protein known as CIITA (class II transactivator) which is a non-DNA binding protein, serves as a master control factor for MCHII expression. In contrast to the other enhanceosome members, CIITA does exhibit tissue specific expression, is up-regulated by IFN-γ, and has been shown to be inhibited by several bacteria and viruses which can cause a down regulation of MHC class II expression (thought to be part of a bacterial attempt to evade immune surveillance (see Leibund Gut-Landmann et al (2004) Eur. J. Immunol 34:1513-1525)).

Regulation of the class I or II genes can be disrupted in the presence of some tumors and such disruption can have consequences on the prognosis of the patients. For example, in some melanomas, an observed reduction in Tap 1, Tap 2 and HLA class I antigens was found to be more common in metastatic melanomas (P<0.05) than in primary tumors (see Kageshita et al (1999) Am Jour of Pathol 154(3):745-754).

In humans, susceptibility to several diseases is suspected to be tied to HLA haplotype. These diseases include Addison's disease, ankylosing spondylitis, Behçet's disease, Buerger's disease, celiac disease, chronic active hepatitis, Graves' disease, juvenile rheumatoid arthritis, psoriasis, psoriatic arthritis, rheumatoid arthritis, Sjögren syndrome, and lupus erythematosus, among others.

HLA haplotype also plays a major role in transplant rejection. The acute phase of transplant rejection can occur within about 1-3 weeks and usually involves the action of host T lymphocytes on donor tissues due to sensitization of the host system to the donor class I and class II HLA molecules. In most cases, the triggering antigens are the class I HLAs. For best success, donors are typed for HLA haplotype and matched to the patient recipient as completely as possible. But donation even between family members, which can share a high percentage of HLA haplotype identity, is still often not successful. Thus, in order to preserve the graft tissue within the recipient, the patient often must be subjected to profound immunosuppressive therapy to prevent rejection. Such therapy can lead to complications and significant morbidities due to opportunistic infections that the patient may have difficulty overcoming.

Cell therapy is a specialized type of transplant wherein cells of a certain type (e.g. T cells reactive to a tumor antigen or B cells) are given to a recipient. Cell therapy can be done with cells that are either autologous (derived from the recipient) or allogenic (derived from a donor) and the cells may be immature cells such as stem cells, or completely mature and functional cells such as T cells. In fact, in some diseases such certain cancers, T cells may be manipulated ex vivo to increase their avidity for certain tumor antigens, expanded and then introduced into the patient suffering from that cancer type in an attempt to eradicate the tumor. This is particularly useful when the endogenous T cell response is suppressed by the tumor itself. However, the same caveats apply for cell therapy as apply for more well known solid organ transplants in regards to rejection. Donor T cells express class I HLA antigens and thus are capable of eliciting a rejection response from the recipient's endogenous immune system.

Thus, there remains a need for compositions and methods for the manipulation of HLA genes and gene expression in cells.

SUMMARY

Disclosed herein are methods and compositions for manipulating HLA gene complexes or HLA gene expression. In particular, provided herein are methods and compositions for modulating expression of an HLA gene so as to treat HLA-related disorders, for example human disorders related to HLA haplotype of the individual. Additionally, provided herein are methods and compositions for deleting or repressing an HLA gene to produce an HLA null cell, cell fragment (e.g. platelet), tissue or whole organism. Additionally, these methods and compositions may be used to create a cell, cell fragment, tissue or organism that is null for just one HLA gene, or more than one HLA gene, or is completely null for all HLA genes. In certain embodiments, the HLA null cells or tissues are human cells or tissues that are advantageous for use in transplants.

Thus, in one aspect, engineered DNA-binding domains (e.g., zinc finger proteins or TALE DNA binding domain proteins) that modulate expression of an HLA allele are provided. In certain embodiments, the DNA binding domain comprises engineered zinc finger proteins that are non-naturally occurring as well as zinc finger proteins whose recognition helices have been altered (e.g., by selection and/or rational design) to bind to a pre-selected target site. Any of the zinc finger proteins described herein may include 1, 2, 3, 4, 5, 6 or more zinc fingers, each zinc finger having a recognition helix that binds to a target subsite in the selected sequence(s) (e.g., gene(s)). In some embodiments, one or more of the recognition helices of the zinc finger domains of the zinc finger protein is non-naturally occurring. In certain embodiments, the zinc finger proteins have the recognition helices shown in Table 1. In other embodiments, the zinc finger proteins bind to the target sites shown in Table 2. In other embodiments, the DNA binding domain comprises a TALE DNA binding domain (e.g., a TALE DNA binding domain comprising naturally occurring and/or non-naturally occurring TALE binding domains).

In certain embodiments, the DNA-binding proteins (e.g., zinc finger proteins (ZFPs) or TALE DNA binding proteins) as described herein can be placed in operative linkage with a regulatory domain (or functional domain) as part of a fusion protein. In certain embodiments, the regulatory domain is an activation domain or repression domain for fusion with the DNA-binding domain, and such fusion proteins (i.e. ZFP- or TALE-transcription factor fusions: ZFP-TF and TALE-TF respectively) can be used either to activate or to repress gene expression. In some embodiments, repressors are provided which are capable of preferentially binding to HLA genes or modulators of HLA gene expression. In certain embodiments, the activity of the regulatory domain is regulated by an exogenous small molecule or ligand such that interaction with the cell's transcription machinery will not take place in the absence of the exogenous ligand. Such external ligands control the degree of interaction of the ZFP-TF or TALE-TF with the transcription machinery.

In one embodiment, the repressors are capable of binding to a specific HLA A, HLA B or HLA C transcriptional regulatory region and are able to repress expression in only one of the above genes. In another aspect, a repressor is provided that is capable of interacting with transcriptional regulatory regions common to HLA A, HLA B and HLA C such that all three genes are regulated with one DNA binding domain (e.g., ZFP TF or TALE TF). In another embodiment, a repressor is capable of binding to a regulator of HLA class II expression or function (e.g. CIITA or RFX5) to repress its activity and thus repress HLA class II expression or function.

In other embodiments, repressing DNA binding domain-transcription factor fusions are provided which preferentially bind to known HLA haplotypes to repress expression of only one allele.

In another aspect, DNA-binding domain-transcription factor fusions that specifically activate the expression of HLA genes are provided. Such fusions may up-regulate a class of HLA genes by increasing expression of a regulator, or may cause expression of such a class in tissues where these genes are not normally expressed. In another embodiment, provided are DNA-binding domain-transcription factor fusions (e.g., ZFP TFs or TALE TFs) that activate specific HLA genes as desired.

In another aspect, the fusion protein comprises a DNA-binding protein (e.g., ZFP or TALE) as described herein in operative linkage with a functional domain comprising a nuclease (e.g., ZFNs or TALENs). In certain embodiments, provided herein are zinc finger nucleases (ZFNs) or TALE DNA binding domains fused to a nuclease (TALENS) that cleave an HLA gene. In certain embodiments, the ZFNs and/or TALENs bind to target sites in a human HLA class I gene and/or target sites in a human HLA class II gene. In some embodiments, cleavage within the HLA gene(s) with these nucleases results in permanent disruption (e.g., mutation) of the HLA gene. In certain embodiments, two pairs of ZFNs and/or TALENs may be used to cause larger deletions. The deletions may comprise a small portion of one HLA gene, or HLA regulator gene, or may comprise larger segments. In some embodiments, the deletions caused by the ZFNs or TALENs may delete one or more HLA genes or may delete an entire HLA gene complex (i.e., all of the class I HLA genes, or all of the HLA class II genes). The deletions may also encompass the deletion of a subset of a class of HLA genes. The zinc finger DNA binding proteins may include 1, 2, 3, 4, 5, 6 or more zinc fingers, each zinc finger having a recognition helix that binds to a target subsite in the target gene. In certain embodiments, the zinc finger proteins comprise 4 or 5 or 6 fingers (where the fingers are designated F1, F2, F3, F4, F5 and F6 and ordered F1 to F4 or F5 or F6 from N-terminus to C-terminus) and the fingers comprise the amino acid sequence of the recognition regions shown in Table 1.

Any of the ZFN or TALEN proteins described herein may further comprise a cleavage domain and/or a cleavage half-domain (e.g., a wild-type or engineered FokI cleavage half-domain). Thus, in any of the ZFNs or TALENs described herein, the nuclease domain may comprise a wild-type nuclease domain or nuclease half-domain (e.g., a FokI cleavage half domain). In other embodiments, the ZFNs or TALENs comprise engineered (non-naturally occurring) nuclease domains or half-domains, for example engineered FokI cleavage half domains that form obligate heterodimers. See, e.g., U.S. Patent Publication No. 20080131962.

In another aspect, the disclosure provides a polynucleotide encoding any of the proteins described herein. Any of the polynucleotides described herein may also comprise sequences (donor or patch sequences) for targeted insertion into the HLA genes.

In yet another aspect, a gene delivery vector comprising any of the polynucleotides described herein is provided. In certain embodiments, the vector is an adenovirus vector (e.g., an Ad5/F35 vector), a lentiviral vector (LV) including integration competent or integration-defective lentiviral vectors, or an adenovirus associated viral vector (AAV). Thus, also provided herein are adenovirus (Ad) vectors, LV or adenovirus associate viral vectors (AAV) comprising a sequence encoding at least one nuclease as described herein (e.g., ZFN or TALEN) and/or a donor sequence for targeted integration into a target gene. In certain embodiments, the Ad vector is a chimeric Ad vector, for example an Ad5/F35 vector. In certain embodiments, the lentiviral vector is an integrase-defective lentiviral vector (IDLV) or an integration competent lentiviral vector. In certain embodiments the vector is pseudo-typed with a VSV-G envelope, or with other envelopes.

In additional embodiments, the target gene is a gene (e.g., in a human cell) that regulates HLA expression (an HLA regulator gene). In certain embodiments, a CTIIA, a RFX5 gene, aTAP1, TAP2 or tapasin gene, or combination thereof are targeted for regulation (e.g., activation, repression or inactivation). In some embodiments, the target gene encodes a microRNA capable of regulating HLA genes. The vectors described herein may also comprise donor sequences. In additional embodiments, the donor sequences comprise human HLA genes or HLA regulator genes that are not endogenous to the host cell. In some embodiments, the HLA genes or HLA regulator genes of interest are inserted into the location of the endogenous HLA genes or HLA regulator genes, and in other embodiments the HLA genes or HLA regulator genes of interest are inserted into randomly selected loci, or into a separate locus after genome-wide delivery. In some embodiments, the separate locus for HLA transgene or HLA regulator transgene insertion is the PPP1R12C locus (see U.S Patent Publication Number 20080299580). In other embodiments, the HLA transgene or HLA regulator transgene is inserted into a CCR-5 locus. In some aspects, the donor comprises another nucleic acid of interest. By way of example only, this donor may contain a gene encoding a polypeptide of interest, or it may comprise a sequence encoding a structural RNA (shRNA, miRNA, RNAi etc.). In some embodiments, cells are provided wherein an HLA gene or HLA regulator gene of interest has been manipulated in a desired fashion (e.g. knocked-out, corrected etc.) and a donor and one or more additional of ZFNs and/or TALENs are provided to insert the donor into another locus (e.g. AAVS1).

In certain embodiments, a single vector comprises sequences encoding one or more nucleases as described herein (e.g., ZFNs and/or TALENs) and the donor sequence(s). In other embodiments, the donor sequence(s) are contained in a first vector and the nuclease-encoding sequences are present in a second vector.

In yet another aspect, the disclosure provides a cell (e.g., an isolated cell) comprising any of the proteins, polynucleotides and/or vectors described herein. In certain embodiments, the cell is selected from the group consisting of a stem/progenitor cell, a lymphocyte, a B cell, or a T-cell (e.g., CD4+ T-cell). In other embodiments, the cell is a cell fragment, including, but not limited to a platelet.

In another aspect, described herein are methods of inactivating an HLA gene or HLA regulator gene in a cell by introducing one or more proteins, polynucleotides and/or vectors into the cell as described herein. In any of these methods the nucleases may induce targeted mutagenesis, targeted deletions, targeted insertions of cellular DNA sequences, and/or facilitate targeted recombination at a predetermined chromosomal locus. Thus, in certain embodiments, the nucleases (e.g., ZFNs and/or TALENs) delete and/or insert one or more nucleotides at the target gene. In some embodiments the HLA gene is inactivated by nuclease (ZFN and/or TALEN) cleavage followed by non-homologous end joining. In other embodiments, a genomic sequence in the target gene is replaced, for example using one or more pairs of ZFNs (or vector encoding said ZFNs) and/or one or more TALENs as described herein and a "donor" sequence that is inserted into the gene following targeted cleavage with the ZFN(s) and/or TALEN(s). The donor sequence may be present in the nuclease fusion vector, present in a separate vector (e.g., Ad, AAV or LV vector) or, alternatively, may be introduced into the cell using a different nucleic acid delivery mechanism. In some embodiments, the ZFNs and/or TALENs are delivered using the mRNAs that encode them. In some embodiments, the nucleic acids may be delivered by electroporation or another technique suitable for the delivery of naked nucleic acid.

In another aspect, methods of using the DNA-binding proteins and fusions thereof for mutating an HLA gene and/or inactivating HLA function in a cell or cell line are provided. Thus, a method for inactivating an HLA gene in a human cell is provided, the method comprising administering to the cell any of the proteins or polynucleotides described herein. Methods are also provided herein for altering MHC function in any model organism.

In another aspect, the compositions and methods described herein can be used, for example, in the treatment or prevention or amelioration of any HLA-related disorder (i.e., related to HLA haplotype). The methods typically comprise (a) cleaving an endogenous HLA gene or HLA regulator gene in an isolated cell (e.g., T-cell or lymphocyte) using a nuclease (e.g., ZFN or TALEN) such that the HLA or HLA regulator gene is inactivated; and (b) introducing the cell into the subject, thereby treating or preventing an HLA-related disorder. In certain embodiments, the HLA-related disorder is graft-versus-host disease (GVHD). The nuclease(s) can be introduced as mRNA, in protein form and/or as a DNA sequence encoding the nuclease(s). In certain embodiments, the isolated cell introduced into the subject further comprises additional genomic modification, for example, an integrated exogenous sequence (into the cleaved HLA or HLA regulatory gene or a different gene, for example a safe harbor gene) and/or inactivation (e.g., nuclease-mediated) of additional genes, for example one or more TCR genes. The exogenous sequence may be introduced via a vector (e.g. Ad, AAV, LV), or by using a technique such as electroporation. In some aspects, the composition may comprise isolated cell fragments and/or differentiated cells.

In some embodiments, nuclease fusions as described herein may be utilized for targeting stem cells such as induced pluripotent stem cells (iPSC), human embryonic stem cells (hES), mesenchymal stem cells (MSC), hematopoietic stem cells (HSC) or neuronal stem cells wherein the activity of the nuclease fusion will result in an HLA allele containing a deletion. In some embodiments, the methods may be used to create stem cells in which more than one HLA gene has been altered. In other embodiments, the invention provides methods for producing stem cells that have an HLA null phenotype. In some aspects, the stem cells may be null for one or more or all HLA class II gene expression. In other aspects, the stem cells may be null for one or more or all HLA class I gene expression. In some aspects, the stem cells are null for all HLA gene expression. In other embodiments, the stem cells that have been modified at the HLA locus/loci are then differentiated.

Also provided are pharmaceutical compositions comprising the modified stem cells. Such pharmaceutical compositions may be used prophylactically or therapeutically and may comprise iPSCs, hES, MSCs, HSCs or combinations and/or derivatives thereof. In other embodiments, cells, cell fragments (e.g., platelets) or tissues derived from such modified stem cells are provided such that such tissues are modified in the HLA loci as desired. In some aspects, such cells are partially differentiated (e.g. hematopoietic stem cells) while in others fully differentiated cells are provided (e.g. lymphocytes or megakarocytes) while in still others, fragments of differentiated cells are provided. In other embodiments, stem cells, and/or their differentiated progeny are provided that contain an altered HLA or HLA regulator gene or genes, and they also can contain an additional genetic modification including a deletion, alteration or insertion of a donor DNA at another locus of interest.

In some embodiments, cells treated with the DNA-binding domains or fusion proteins as described herein (e.g., ZFP-TF, TALE DNA binding domains TFs, ZFNs, and/or TALENs) may be mature cells such as CD4+ T cells or NK cells. Such cells may comprise a protein comprising a DNA-binding domain as described herein for regulation of an HLA gene or HLA regulator gene, or may comprise a nuclease fusion (e.g., ZFN or TALEN) for introduction of a deletion and/or insertion into an HLA gene. In some aspects, such ZFN or TALEN comprising cells may additionally comprise an exogenous DNA sequence. In some aspects, the mature cells may be used for cell therapy, for example, for a T cell transplant. In other embodiments, the cells for use in T cell transplant contain another gene modification of interest. In one aspect, the T cells contain an inserted chimeric antigen receptor (CAR) specific for a cancer marker. In a further aspect, the inserted CAR is specific for the CD19 marker characteristic of B cell malignancies. Such cells would be useful in a therapeutic composition for treating patients without having to match HLA haplotype, and so would be able to be used as an "off-the-shelf" therapeutic for any patient in need thereof. In some aspects, cells in which genes encoding the TCRα and/or TCRβ chains have been manipulated or in which genes encoding TCR chains with desired specificity and affinity have been introduced are provided. In other embodiments, HLA modified platelets are provided for therapeutic use in treatment of disorders such as thrombocytopenia or other bleeding disorders.

In still further aspects, the invention provides methods and compositions for the generation of specific model systems for the study of HLA disorders. In certain embodiments, models in which mutant HLA alleles are generated in embryonic stem cells for the generation of cell and animal lines are provided. In certain embodiments, the model systems comprise in vitro cell lines, while in other embodiments, the model systems comprise transgenic animals. In other embodiments, the invention provides methods and compositions for correcting a mutated HLA gene or HLA regulator and also provides methods and compositions for replacing one HLA allele with another.

In some embodiments, model systems are provided for HLA disorders wherein the target alleles (e.g., specific HLA haplotypes) are tagged with expression markers. In certain embodiments, mutant alleles (e.g., mutant HLA or HLA regulators) are tagged. In certain embodiments, the model systems comprise in vitro cell lines, while in other embodiments, the model systems comprise transgenic animals.

Additionally, pharmaceutical compositions containing the nucleic acids and/or DNA-binding domains (or fusion proteins comprising the DNA-binding domains) are also provided. For example, certain compositions include a nucleic acid comprising a sequence that encodes one of the ZFPs and/or TALE DNA binding domains described herein operably linked to a regulatory sequence, combined with a pharmaceutically acceptable carrier or diluent, wherein the regulatory sequence allows for expression or repression of the nucleic acid in a cell. In certain embodiments, the ZFPs and/or TALE DNA binding domains encoded are specific for an HLA allele. Protein based compositions include one of more ZFPs TALE DNA binding domains as disclosed herein and a pharmaceutically acceptable carrier or diluent.

Any of the methods described herein can be practiced in vitro, in vivo and/or ex vivo. In certain embodiments, the methods are practiced ex vivo, for example to modify T-cells or NK cells prior to use for treating a subject in need thereof.

These and other aspects will be readily apparent to the skilled artisan in light of disclosure as a whole.

BRIEF DESCRIPTION OF THE DRAWINGS

FIG. 3A ("parental") depicts the parental HEK293 cells lacking any ZFN treatment. The column on the left indicates staining for the HLA A2 allele while the column on the right indicates staining for the HLA A3 allele. The furthermost left peak in each panel indicates the isotype control (background). In the parental cells, the peak to the furthest right indicates the results for the antibodies staining a B-LCL clone (positive control). The second to most left peak indicates the amount of A2 or A3 positive cells prior to cytokine (IFN gamma) treatment, while the second furthest to the right peak indicates the results for HLA A2 or A3 expression following cytokine treatment. FIGS. 3B to 3D, corresponding to cell clones 18-1 (A2+A3−) (FIG. 3B), 8.18 (A2−A3+) (FIG. 3C) and 83 (A2−A3−) (FIG. 3D) contain the same analyses as shown in FIG. 3A (except the positive B cell staining the line farthest to the right in the parental panels is not shown). Thus, these data indicate that when the allele of interest is disrupted, no expression of the cell marker is observed, even upon cytokine stimulation.

FIG. 4A depicts the results when using HLA A3 specific CTLs and HEK293 target cells with increasing concentrations of their peptide antigen. Cells that contain the unmodified A3 HLA gene product are lysed (parental, 8.18 and B-LCL). In FIG. 4B, a lysis experiment was carried out using CTLs specific for HLA A2 in conjunction with a specific peptide antigen. When increasing concentrations of peptide are used, the CTLs are able to lyse those cells containing an intact HLA A2 gene product (parental HEK293, 18-1 and B-LCL). Thus, when expression of the HLA A gene targeted by the CTLs is disrupted, the cells are no longer susceptible to CTL directed lysis.

FIG. 5A depicts the results using standard cell culture conditions following transfection, while FIG. 5B depicts the results using the "transient cold shock" methodology. Up to nearly 42% of the cells can display an HLA A2 disruption characteristic using the "cold shock" methodology.

FIG. 7, panels A and B, depict gels displaying the results of a Cel-I mismatch analysis for ZFNs specific for the HLA C (FIG. 7A) and HLA B (FIG. 7B) genes. The arrows indicate the band on the gel indicative of gene modification.

FIG. 8, panels A and B, depict gels displaying the results of a Cel-I mismatch analysis for ZNFs specific for a target sequence downstream of the HLA C gene ("HLA C-down") and a target sequence upstream of the HLA B gene ("HLA B-up"). FIG. 8A depicts the results for the HLA C-down specific ZFN pair where ZFNs containing a wild type FokI catalytic domain (wt) and the ZFN pair containing an EL/KK heterodimeric FokI domain (mut) are shown. The arrow depicts the band indicating the mismatch. The percent gene modification detected is shown at the bottom of each lane ("% NHEJ"). FIG. 8B depicts the results for two HLA B-up ZFN pairs where the arrow point out the bands indicative of gene modification.

FIG. 9, panels A and B, illustrates an experiment designed to create a large deletion that includes both the HLA B and the HLA C locus. FIG. 9A is a schematic of the HLA gene complex in the area of HLA B and HLA C, and the regions targeted by the HLA B-up and HLA C-down ZFNs are indicated. The location of the primers used for the PCR to visualize the deletion are also indicated. FIG. 9B depicts the results of the deletion specific PCR following cleavage with the HLA B-up and HLA C-down ZFNs in K562 cells. The lanes on the left side of the gel are a dilution series of a deletion PCR product that we inserted into a plasmid in order to quantitate the signal from the PCR. The deletion PCR was performed on DNAs isolated 3 and 10 days following nucleofection, and the ZFNs used contained either the wild-type ("wt") or mutated ("mut") FokI catalytic domain (as discussed above in FIG. 8). The results indicate that at day 3, approximately 5% of the alleles contained the HLA B and HLA C deletion.

FIG. 10A depicts the results of a Cel I mismatch assay with ZFNs targeted the TAP1 gene, while FIG. 10B depicts the results when the ZFNs targeted the TAP2 gene. ZFNs used are indicated above the appropriate lanes. These results indicate that these ZFNs are active in cleaving target DNA.

DETAILED DESCRIPTION

Figure 1:
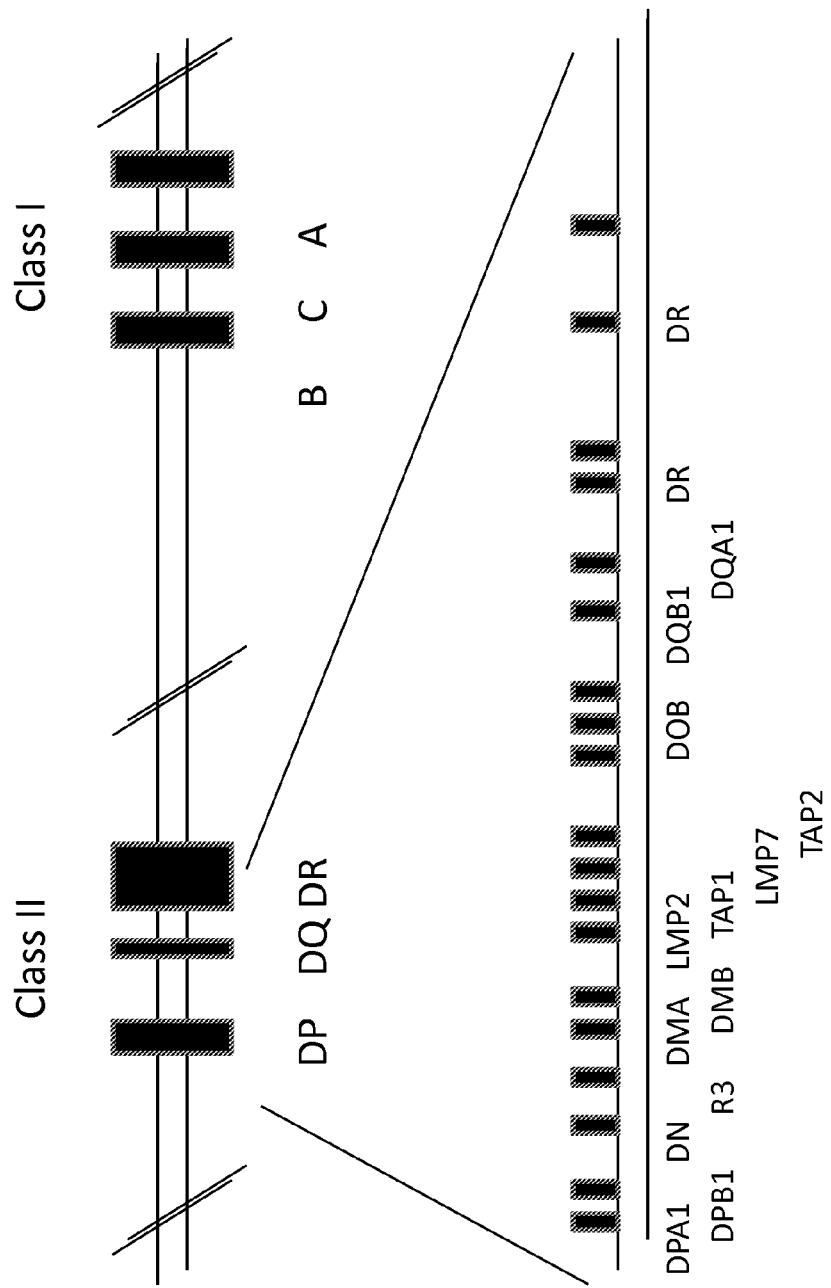
FIG. 1 depicts a schematic of some of the genes of the MHC Class I and Class II clusters.

Disclosed herein are DNA binding domains (e.g., ZFP and/or TALE DNA binding proteins) and fusion proteins comprising these DNA binding domains (e.g., ZFNs, TALENs, ZFP-TFs and TALE-TFs) for targeting an HLA gene or an HLA regulator. The proteins described herein can repress or activate a specific HLA gene, and change its expression. Similarly, DNA-binding proteins as described herein can target a HLA regulator and through modulating its expression, can cause a change in HLA expression. Also disclosed and provided herein are compositions including ZFNs and/or TALENs and methods for altering an HLA gene. These include compositions and methods using engineered DNA-binding domains, i.e., non-naturally occurring proteins which bind to a predetermined nucleic acid target sequence. The DNA binding domains and fusion proteins comprising these DNA-binding domains as described herein can act efficiently and specifically on a desired HLA gene or genes, and can result in a deletion of the specific gene and/or the introduction of an alternate gene of interest into the targeted locus. Cells targeted in this manner can be used as therapeutics, for example, transplants, or can be used to generate either in vitro or in vivo model systems to study HLA gene function. Such cells can also be used as drug screening tools to isolate and characterize small molecules or other types of therapeutics for compounds that will act upon HLA expression. Cells can also be generated in which following knock out of the desired HLA genes, other HLA genes may be inserted to change the HLA gene products that are expressed on the cell's surface. Additionally, other genes of interest may be inserted into cells in which the HLA genes have been manipulated.

Thus, the methods and compositions described herein provide methods for treatment of HLA related disorders, and these methods and compositions can comprise zinc finger transcription factors capable of modulating target genes as well as engineered zinc finger nucleases.

General

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolfe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

Definitions

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues.

The term also applies to amino acid polymers in which one or more amino acids are chemical analogues or modified derivatives of corresponding naturally-occurring amino acids.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ $M^{-1}$ or lower. "Affinity" refers to the strength of binding: increased binding affinity being correlated with a lower $K_d$.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

A "TALE DNA binding domain" or "TALE" is a polypeptide comprising one or more TALE repeat domains/units. The repeat domains are involved in binding of the TALE to its cognate target DNA sequence. A single "repeat unit" (also referred to as a "repeat") is typically 33-35 amino acids in length and exhibits at least some sequence homology with other TALE repeat sequences within a naturally occurring TALE protein.

Zinc finger binding domains can be "engineered" to bind to a predetermined nucleotide sequence, for example via engineering (altering one or more amino acids) of the recognition helix region of a naturally occurring zinc finger protein. Similarly, TALEs can be "engineered" to bind to a predetermined nucleotide sequence, for example by engineering of the amino acids involved in DNA binding (the repeat variable diresidue or RVD region). Therefore, engineered zinc finger proteins or TALE proteins are proteins that are non-naturally occurring. Non-limiting examples of methods for engineering zinc finger proteins and TALEs are design and selection. A designed protein is a protein not occurring in nature whose design/composition results principally from rational criteria. Rational criteria for design include application of substitution rules and computerized algorithms for processing information in a database storing information of existing ZFP or TALE designs and binding data. See, for example, U.S. Pat. Nos. 6,140,081; 6,453,242; and 6,534,261; see also WO 98/53058; WO 98/53059; WO 98/53060; WO 02/016536 and WO 03/016496.

A "selected" zinc finger protein or TALE is a protein not found in nature whose production results primarily from an empirical process such as phage display, interaction trap or hybrid selection. See e.g., U.S. Pat. Nos. 5,789,538; 5,925,523; 6,007,988 ; 6,013,453; 6,200,759; WO 95/19431; WO 96/06166; WO 98/53057; WO 98/54311; WO 00/27878; WO 01/60970 WO 01/88197 and WO 02/099084.

"Recombination" refers to a process of exchange of genetic information between two polynucleotides. For the purposes of this disclosure, "homologous recombination (HR)" refers to the specialized form of such exchange that takes place, for example, during repair of double-strand breaks in cells via homology-directed repair mechanisms. This process requires nucleotide sequence homology, uses a "donor" molecule to template repair of a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to resynthesize genetic information that will become part of the target, and/or related processes. Such specialized HR often results in an alteration of the sequence of the target molecule such that part or all of the sequence of the donor polynucleotide is incorporated into the target polynucleotide.

In the methods of the disclosure, one or more targeted nucleases as described herein create a double-stranded break in the target sequence (e.g., cellular chromatin) at a predetermined site, and a "donor" polynucleotide, having homology to the nucleotide sequence in the region of the break, can be introduced into the cell. The presence of the double-stranded break has been shown to facilitate integration of the donor sequence. The donor sequence may be physically integrated or, alternatively, the donor polynucleotide is used as a template for repair of the break via homologous recombination, resulting in the introduction of all or part of the nucleotide sequence as in the donor into the cellular chromatin. Thus, a first sequence in cellular chromatin can be altered and, in certain embodiments, can be converted into a sequence present in a donor polynucleotide. Thus, the use of the terms "replace" or "replacement" can be understood to represent replacement of one nucleotide sequence by another, (i.e., replacement of a sequence in the informational sense), and does not necessarily require physical or chemical replacement of one polynucleotide by another.

In any of the methods described herein, additional pairs of zinc-finger proteins can be used for additional double-stranded cleavage of additional target sites within the cell.

In certain embodiments of methods for targeted recombination and/or replacement and/or alteration of a sequence in a region of interest in cellular chromatin, a chromosomal sequence is altered by homologous recombination with an exogenous "donor" nucleotide sequence. Such homologous recombination is stimulated by the presence of a double-stranded break in cellular chromatin, if sequences homologous to the region of the break are present.

In any of the methods described herein, the first nucleotide sequence (the "donor sequence") can contain sequences that are homologous, but not identical, to genomic sequences in the region of interest, thereby stimulating homologous recombination to insert a non-identical sequence in the region of interest. Thus, in certain embodiments, portions of the donor sequence that are homologous to sequences in the region of interest exhibit between about 80 to 99% (or any integer therebetween) sequence identity to the genomic sequence that is replaced. In other embodiments, the homology between the donor and genomic sequence is higher than 99%, for example if only 1 nucleotide differs as between donor and genomic sequences of over 100 contiguous base pairs. In certain cases, a non-homologous portion of the donor sequence can contain sequences not present in the region of interest, such that new sequences are introduced into the region of interest. In these instances, the non-homologous sequence is generally flanked by sequences of 50-1,000 base pairs (or any integral value therebetween) or any number of base pairs greater than 1,000, that are homologous or identical to sequences in the region of interest. In other embodiments, the donor sequence is non-homologous to the first sequence, and is inserted into the genome by non-homologous recombination mechanisms.

Any of the methods described herein can be used for partial or complete inactivation of one or more target sequences in a cell by targeted integration of donor sequence that disrupts expression of the gene(s) of interest. Cell lines with partially or completely inactivated genes are also provided.

Furthermore, the methods of targeted integration as described herein can also be used to integrate one or more exogenous sequences. The exogenous nucleic acid sequence can comprise, for example, one or more genes or cDNA molecules, or any type of coding or noncoding sequence, as well as one or more control elements (e.g., promoters). In addition, the exogenous nucleic acid sequence may produce one or more RNA molecules (e.g., small hairpin RNAs (shRNAs), inhibitory RNAs (RNAis), microRNAs (miRNAs), etc.).

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "cleavage half-domain" is a polypeptide sequence which, in conjunction with a second polypeptide (either identical or different) forms a complex having cleavage activity (preferably double-strand cleavage activity). The terms "first and second cleavage half-domains;" "+ and − cleavage half-domains" and "right and left cleavage half-domains" are used interchangeably to refer to pairs of cleavage half-domains that dimerize.

An "engineered cleavage half-domain" is a cleavage half-domain that has been modified so as to form obligate heterodimers with another cleavage half-domain (e.g., another engineered cleavage half-domain). See, also, U.S. Patent Publication Nos. 2005/0064474, 20070218528 and 2008/0131962, incorporated herein by reference in their entireties.

The term "sequence" refers to a nucleotide sequence of any length, which can be DNA or RNA; can be linear, circular or branched and can be either single-stranded or double stranded. The term "donor sequence" refers to a nucleotide sequence that is inserted into a genome. A donor sequence can be of any length, for example between 2 and 10,000 nucleotides in length (or any integer value therebetween or thereabove), preferably between about 100 and 1,000 nucleotides in length (or any integer therebetween), more preferably between about 200 and 500 nucleotides in length.

"Chromatin" is the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

A "chromosome," is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes.

A "target site" or "target sequence" is a nucleic acid sequence that defines a portion of a nucleic acid to which a binding molecule will bind, provided sufficient conditions for binding exist. For example, the sequence 5' GAATTC 3' is a target site for the Eco RI restriction endonuclease. Exemplary target sites for various targeted ZFPs are shown in Table 2.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer. An exogenous molecule can also be the same type of molecule as an endogenous molecule but derived from a different species than the cell is derived from. For example, a human nucleic acid sequence may be introduced into a cell line originally derived from a mouse or hamster.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

A "fusion" molecule is a molecule in which two or more subunit molecules are linked, preferably covalently. The subunit molecules can be the same chemical type of molecule, or can be different chemical types of molecules. Examples of the first type of fusion molecule include, but are not limited to, fusion proteins (for example, a fusion between a ZFP DNA-binding domain and one or more activation domains) and fusion nucleic acids (for example, a nucleic acid encoding the fusion protein described supra). Examples of the second type of fusion molecule include, but are not limited to, a fusion between a triplex-forming nucleic acid and a polypeptide, and a fusion between a minor groove binder and a nucleic acid.

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" of gene expression refers to a change in the activity of a gene. Modulation of expression can include, but is not limited to, gene activation and gene repression. Genome editing (e.g., cleavage, alteration, inactivation, random mutation) can be used to modulate expression. Gene inactivation refers to any reduction in gene expression as compared to a cell that does not include a ZFP as described herein. Thus, gene inactivation may be partial or complete.

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs.

"Eukaryotic" cells include, but are not limited to, fungal cells (such as yeast), plant cells, animal cells, mammalian cells and human cells (e.g., T-cells).

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion polypeptide in which a ZFP DNA-binding domain is fused to an activation domain, the ZFP DNA-binding domain and the activation domain are in operative linkage if, in the fusion polypeptide, the ZFP DNA-binding domain portion is able to bind its target site and/or its binding site, while the activation domain is able to up-regulate gene expression. When a fusion polypeptide in which a ZFP DNA-binding domain is fused to a cleavage domain, the ZFP DNA-binding domain and the cleavage domain are in operative linkage if, in the fusion polypeptide, the ZFP DNA-binding domain portion is able to bind its target site and/or its binding site, while the cleavage domain is able to cleave DNA in the vicinity of the target site.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one ore more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis. See Ausubel et al., supra. The ability of a protein to interact with another protein can be determined, for example, by co-immunoprecipitation, two-hybrid assays or complementation, both genetic and biochemical. See, for example, Fields et al. (1989) *Nature* 340:245-246; U.S. Pat. No. 5,585,245 and PCT WO 98/44350.

A "vector" is capable of transferring gene sequences to target cells. Typically, "vector construct," "expression vector," and "gene transfer vector," mean any nucleic acid construct capable of directing the expression of a gene of interest and which can transfer gene sequences to target cells. Thus, the term includes cloning, and expression vehicles, as well as integrating vectors.

A "reporter gene" or "reporter sequence" refers to any sequence that produces a protein product that is easily measured, preferably although not necessarily in a routine assay. Suitable reporter genes include, but are not limited to, sequences encoding proteins that mediate antibiotic resistance (e.g., ampicillin resistance, neomycin resistance, G418 resistance, puromycin resistance), sequences encoding colored or fluorescent or luminescent proteins (e.g., green fluorescent protein, enhanced green fluorescent protein, red fluorescent protein, luciferase), and proteins which mediate enhanced cell growth and/or gene amplification (e.g., dihydrofolate reductase). Epitope tags include, for example, one or more copies of FLAG, His, myc, Tap, HA or any detectable amino acid sequence. "Expression tags" include sequences that encode reporters that may be operably linked to a desired gene sequence in order to monitor expression of the gene of interest.

DNA-Binding Domains

Described herein are compositions comprising a DNA-binding domain that specifically bind to a target site in any gene comprising a HLA gene or a HLA regulator. Any DNA-binding domain can be used in the compositions and methods disclosed herein.

In certain embodiments, the DNA binding domain comprises a zinc finger protein. Preferably, the zinc finger protein is non-naturally occurring in that it is engineered to bind to a target site of choice. See, for example, Beerli et al. (2002) *Nature Biotechnol.* 20:135-141; Pabo et al. (2001) *Ann. Rev. Biochem.* 70:313-340; Isalan et al. (2001) *Nature Biotechnol.* 19:656-660; Segal et al. (2001) *Curr. Opin. Biotechnol.* 12:632-637; Choo et al. (2000) *Curr. Opin. Struct. Biol.* 10:411-416; U.S. Pat. Nos. 6,453,242; 6,534,261; 6,599,692; 6,503,717; 6,689,558; 7,030,215; 6,794,136; 7,067,317; 7,262,054; 7,070,934; 7,361,635; 7,253,273; and U.S. Patent Publication Nos. 2005/0064474; 2007/0218528; 2005/0267061, all incorporated herein by reference in their entireties.

An engineered zinc finger binding domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 6,453,242 and 6,534,261, incorporated by reference herein in their entireties.

Exemplary selection methods, including phage display and two-hybrid systems, are disclosed in U.S. Pat. Nos. 5,789, 538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237. In addition, enhancement of binding specificity for zinc finger binding domains has been described, for example, in co-owned WO 02/077227.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein. In addition, enhancement of binding specificity for zinc finger binding domains has been described, for example, in co-owned WO 02/077227.

Selection of target sites; ZFPs and methods for design and construction of fusion proteins (and polynucleotides encoding same) are known to those of skill in the art and described in detail in U.S. Pat. Nos. 6,140,081; 5,789,538; 6,453,242; 6,534,261; 5,925,523; 6,007,988; 6,013,453; 6,200,759; WO 95/19431; WO 96/06166; WO 98/53057; WO 98/54311; WO 00/27878; WO 01/60970 WO 01/88197; WO 02/099084; WO 98/53058; WO 98/53059; WO 98/53060; WO 02/016536 and WO 03/016496.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

Alternatively, the DNA-binding domain may be derived from a nuclease. For example, the recognition sequences of homing endonucleases and meganucleases such as I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII are known. See also U.S. Pat. Nos. 5,420,032; 6,833,252; Belfort et al. (1997) *Nucleic Acids Res.* 25:3379-3388; Dujon et al. (1989) *Gene* 82:115-118; Perler et al. (1994) *Nucleic Acids Res.* 22, 1125-1127; Jasin (1996) *Trends Genet.* 12:224-228; Gimble et al. (1996) *J. Mol. Biol.* 263:163-180; Argast et al. (1998) *J. Mol. Biol.* 280:345-353 and the New England Biolabs catalogue. In addition, the DNA-binding specificity of homing endonucleases and meganucleases can be engineered to bind non-natural target sites. See, for example, Chevalier et al. (2002) *Molec. Cell* 10:895-905; Epinat et al. (2003) *Nucleic Acids Res.* 31:2952-2962; Ashworth et al. (2006) *Nature* 441:656-659; Paques et al. (2007) *Current Gene Therapy* 7:49-66; U.S. Patent Publication No. 20070117128.

In certain embodiments, the DNA binding domain is an engineered zinc finger protein that binds (in a sequence-specific manner) to a target site in a HLA gene or HLA regulatory gene and modulates expression of HLA. The ZFPs can bind selectively to a specific haplotype of interest. For a discussion of HLA haplotypes identified in the United States population and their frequency according to different races, see Maiers et al (2007) *Human Immunology* 68: 779-788, incorporated by reference herein. Additionally, ZFPs are provided that bind to functional HLA regulator genes including, but not limited to, Tap1, Tap2, Tapascin, CTFIIA, and RFX5. HLA target sites typically include at least one zinc finger but can include a plurality of zinc fingers (e.g., 2, 3, 4, 5, 6 or more fingers). Usually, the ZFPs include at least three fingers. Certain of the ZFPs include four, five or six fingers. The ZFPs that include three fingers typically recognize a target site that includes 9 or 10 nucleotides; ZFPs that include four fingers typically recognize a target site that includes 12 to 14 nucleotides; while ZFPs having six fingers can recognize target sites that include 18 to 21 nucleotides. The ZFPs can also be fusion proteins that include one or more regulatory domains, which domains can be transcriptional activation or repression domains.

Specific examples of targeted ZFPs are disclosed in Table 1. The first column in this table is an internal reference name (number) for a ZFP and corresponds to the same name in column 1 of Table 2. "F" refers to the finger and the number following "F" refers which zinc finger (e.g., "F1" refers to finger 1).

TABLE 1

Zinc finger proteins

| Target | SBS # | F1 | F2 | F3 | F4 | F5 | F6 |
|---|---|---|---|---|---|---|---|
| *Class I* | | | | | | | |
| HLA A2 | 18889 | QSSHLTR (SEQ ID NO: 1) | RSDHLTT (SEQ ID NO: 2) | RSDTLSQ (SEQ ID NO: 3) | RSADLSR (SEQ ID NO: 4) | QSSDLSR (SEQ ID NO: 5) | RSDALTQ (SEQ ID NO: 6) |
| HLA A2 | 18881 | QKTHLAK (SEQ ID NO: 7) | RSDTLSN (SEQ ID NO: 8) | RKDVRIT (SEQ ID NO: 9) | RSDHLST (SEQ ID NO: 10) | DSSARKK (SEQ ID NO: 11) | NA |
| HLA A2 | 24859 | QNAHRKT (SEQ ID NO: 12) | RSDSLLR (SEQ ID NO: 13) | RNDDRKK (SEQ ID NO: 14) | RSDHLST (SEQ ID NO: 10) | DSSARKK (SEQ ID NO: 11) | NA |
| HLA A3 | 25191 | DRSHLSR (SEQ ID NO: 15) | RSDDLTR (SEQ ID NO: 16) | DRSDLSR (SEQ ID NO: 17) | QSGHLSR (SEQ ID NO: 18) | NA | NA |
| HLA A3 | 25190 | DRSALSR (SEQ ID NO: 19) | QSSDLRR (SEQ ID NO: 20) | DRSALSR (SEQ ID NO: 19) | DRSHLAR (SEQ ID NO: 21) | RSDDLSK (SEQ ID NO: 22) | DRSHLAR (SEQ ID NO: 21) |
| HLA B | 25316 | SSELLNE (SEQ ID NO: 23) | TSSHLSR (SEQ ID NO: 24) | QSGDRNK (SEQ ID NO: 25) | RSANLAR (SEQ ID NO: 26) | RSDNLRE (SEQ ID NO: 27) | NA |
| HLA B | 25317 | QSGDLTR (SEQ ID NO: 28) | RSDDLTR (SEQ ID NO: 16) | DQSTLRN (SEQ ID NO: 29) | DRSNLSR (SEQ ID NO: 30) | DAFTRTR (SEQ ID NO: 31) | NA |
| HLA B-up | 15267 | RSDNLSE (SEQ ID NO: 32) | ASKTRKN (SEQ ID NO: 33) | TSGNLTR (SEQ ID NO: 34) | RSDALAR (SEQ ID NO: 35) | NA | NA |
| HLA B-up | 15265 | DRSALSR (SEQ ID NO: 19) | QSGNLAR (SEQ ID NO: 36) | DRSALSR (SEQ ID NO: 19) | QSGHLSR (SEQ ID NO: 18) | NA | NA |
| HLA B-up | 17454 | RSDNLSE (SEQ ID NO: 32) | ASKTRKN (SEQ ID NO: 33) | QSGHLSR (SEQ ID NO: 18) | TSGHLSR (SEQ ID NO: 37) | QSGHLSR (SEQ ID NO: 18) | NA |
| HLA B-up | 17456 | RSADLTR (SEQ ID NO: 38) | QSGDLTR (SEQ ID NO: 28) | QSGNLAR (SEQ ID NO: 36) | QSGDLTR (SEQ ID NO: 28) | NA | NA |
| HLA C-down | 15296 | QSGHLSR (SEQ ID NO: 18) | RSDHLST (SEQ ID NO: 10) | QSADRTK (SEQ ID NO: 39) | TSGSLSR (SEQ ID NO: 40) | QSADRTK (SEQ ID NO: 39) | NA |
| HLA C-down | 15298 | QSGDLTR (SEQ ID NO: 28) | RSDHLST (SEQ ID NO: 10) | QSADRTK (SEQ ID NO: 39) | RSDNLSA (SEQ ID NO: 41) | RSDNRTT (SEQ ID NO: 42) | NA |
| HLA C | 25588 | QRSNLVR (SEQ ID NO: 43) | SRSALAR (SEQ ID NO: 44) | QSSDLRR (SEQ ID NO: 20) | RSDDLTR (SEQ ID NO: 16) | RSDDLTR (SEQ ID NO: 16) | NA |
| HLA C | 25589 | RSDDLTR (SEQ ID NO: 16) | DRSDLSR (SEQ ID NO: 17) | QSGHLSR (SEQ ID NO: 18) | RSDHLSA (SEQ ID NO: 45) | ESRYLMV (SEQ ID NO: 46) | NA |
| *Class II* | | | | | | | |
| DBP2-up | 15872 | RSDHLST (SEQ ID NO: 10) | DNANRTK (SEQ ID NO: 47) | QSGDLTR (SEQ ID NO: 28) | RSDALST (SEQ ID NO: 48) | ASSNRKT (SEQ ID NO: 49) | NA |
| DBP2-up | 15873 | TSGNLTR (SEQ ID NO: 34) | DRSDLSR (SEQ ID NO: 17) | RSDNLSE (SEQ ID NO: 32) | RSANLTR (SEQ ID NO: 50) | QSGHLSR (SEQ ID NO: 18) | NA |
| DRA-down | 15909 | RSDNLSE (SEQ ID NO: 32) | TSGSLTR (SEQ ID NO: 51) | TSGHLSR (SEQ ID NO: 37) | RSDNLSQ (SEQ ID NO: 52) | ASNDRKK (SEQ ID NO: 53) | NA |
| DRA-down | 15910 | RSDNLSR (SEQ ID NO: 54) | DNNARIN (SEQ ID NO: 55) | RSDSLSV (SEQ ID NO: 56) | QNQHRIN (SEQ ID NO: 57) | RSDHLSR (SEQ ID NO: 58) | NA |
| *Regulators* | | | | | | | |
| TAP1 | 28386 | DSSDRKK (SEQ ID NO: 59) | DRSHLTR (SEQ ID NO: 60) | RSDALAR (SEQ ID NO: 35) | QSSDLSR (SEQ ID NO: 5) | RSDNLTT (SEQ ID NO: 61) | NA |
| TAP1 | 28385 | RSANLAR (SEQ ID NO: 26) | QSGHLSR (SEQ ID NO: 18) | TSGNLTR (SEQ ID NO: 34) | QSGALVI (SEQ ID NO: 62) | RSDHLSE (SEQ ID NO: 63) | RKHDRTK (SEQ ID NO: 64) |

TABLE 1-continued

Zinc finger proteins

| Target | SBS # | F1 | F2 | F3 | F4 | F5 | F6 |
|---|---|---|---|---|---|---|---|
| TAP2 | 28394 | QSSDLSR (SEQ ID NO: 5) | QSGDLTR (SEQ ID NO: 28) | QSSHLTR (SEQ ID NO: 1) | RSDDRKT (SEQ ID NO: 65) | TSGNLTR (SEQ ID NO: 34) | RSDDLTR (SEQ ID NO: 16) |
| TAP2 | 28393 | RSDNLST (SEQ ID NO: 66) | RSDALAR (SEQ ID NO: 35) | RSDVLSA (SEQ ID NO: 67) | DRSNRIK (SEQ ID NO: 68) | RREDLIT (SEQ ID NO: 69) | TSSNLSR (SEQ ID NO: 70) |
| Tapasin | 28406 | RSDNLSE (SEQ ID NO: 32) | KRCNLRC (SEQ ID NO: 71) | DRSDLSR (SEQ ID NO: 17) | QTTHRNR (SEQ ID NO: 72) | DRSDLSR (SEQ ID NO: 17) | QSSTRAR (SEQ ID NO: 73) |
| Tapasin | 28405 | QSSDLSR (SEQ ID NO: 5) | RSDNLRT (SEQ ID NO: 74) | QSSHLTR (SEQ ID NO: 1) | QSSDLTR (SEQ ID NO: 75) | RSDNLAR (SEQ ID NO: 76) | QKVNLMS (SEQ ID NO: 77) |
| Tapasin | 28404 | TSGNLTR (SEQ ID NO: 34) | LSQDLNR (SEQ ID NO: 78) | RSDSLSA (SEQ ID NO: 79) | DRSHLAR (SEQ ID NO: 21) | RSDHLST (SEQ ID NO: 10) | QSGHLSR (SEQ ID NO: 18) |
| Tapasin | 28403 | RSDDLTR (SEQ ID NO: 16) | SSSNLTK (SEQ ID NO: 80) | TSGSLSR (SEQ ID NO: 40) | QSGKLTR (SEQ ID NO: 28) | RSDHLSE (SEQ ID NO: 63) | RNRDRIT (SEQ ID NO: 81) |
| CTIIA | 15486 | RSDDLRT (SEQ ID NO: 16) | RSDHLSE (SEQ ID NO: 63) | NSRNRKT (SEQ ID NO: 82) | RSDNLSQ (SEQ ID NO: 52) | ASNDRKK (SEQ ID NO: 53) | NA |
| CTIIA | 15487 | RSDDLSR (SEQ ID NO: 83) | RNDDRKK (SEQ ID NO: 14) | DRSDLSR (SEQ ID NO: 17) | RSDHLSE (SEQ ID NO: 63) | ARSTRTN (SEQ ID NO: 84) | NA |
| RFX5 | 15506 | TSGNLTR (SEQ ID NO: 34) | QSGNLAR (SEQ ID NO: 36) | RSDGLTQ (SEQ ID NO: 85) | ASMALNE (SEQ ID NO: 86) | TSSNLSR (SEQ ID NO: 70) | NA |
| RFX5 | 15507 | RSDVLSE (SEQ ID NO: 87) | RNQHRKT (SEQ ID NO: 88) | RSDHLST (SEQ ID NO: 10) | QSSDLRR (SEQ ID NO: 20) | RSDNLSR (SEQ ID NO: 66) | RSADRKN (SEQ ID NO: 89) |
| Others | | | | | | | |
| TRAC | 25539 | QSGDLRT (SEQ ID NO: 28) | QWGTRLR (SEQ ID NO: 90) | ERGTLAR (SEQ ID NO: 91) | RSDNLRE (SEQ ID NO: 27) | QSGDLTR (SEQ ID NO: 28) | TSGSLTR (SEQ ID NO: 51) |
| TRAC | 25540 | QSGDLTR (SEQ ID NO: 28) | WRSSLAS (SEQ ID NO: 92) | QSGDLTR (SEQ ID NO: 28) | HKWVLRQ (SEQ ID NO: 93) | DRSNLTR (SEQ ID NO: 94) | NA |
| TRBC | 16783 | RSDVLSA (SEQ ID NO: 67) | DRSNRIK (SEQ ID NO: 68) | RSDVLSE (SEQ ID NO: 87) | QSGNLAR (SEQ ID NO: 36) | QSGSLTR (SEQ ID NO: 95) | NA |
| TRBC | 16787 | RSDHLST (SEQ ID NO: 10) | RSDNLTR (SEQ ID NO: 74) | DRSNLSR (SEQ ID NO: 30) | TSSNRKT (SEQ ID NO: 96) | RSANLAR (SEQ ID NO: 26) | RNDDRKK (SEQ ID NO: 14) |

The sequence for the target sites of these proteins are disclosed in Table 2. Table 2 shows target sequences for the indicated zinc finger proteins. Nucleotides in the target site that are contacted by the ZFP recognition helices are indicated in uppercase letters; non-contacted nucleotides indicated in lowercase.

TABLE 2

Zinc finger target sites

| Target | SBS # | Target site | |
|---|---|---|---|
| Class I | | | |
| HLA A2 | 18889 | gtATGGCTGCGACGTGGGGTcggacggg_ | (SEQ ID NO: 97) |
| HLA A2 | 18881 | ttATCTGGATGGTGTGAgaacctggccc_ | (SEQ ID NO: 98) |
| HLA A2 | 24859 | tcCTCTGGACGGTGTGAgaacctggccc_ | (SEQ ID NO: 99) |
| HLA A3 | 25191 | atGGAGCCGCGGGCgccgtggatagagc_ | (SEQ ID NO: 100) |
| HLA A3 | 25190 | ctGGCTCGCGGCGTCGCTGTCgaaccgc_ | (SEQ ID NO: 101) |
| HLA B-up | 25316 | tcCAGGAGcTCAGGTCCTcgttcagggc_ | (SEQ ID NO: 102) |
| HLA B-up | 25317 | cgGCGGACACCGCGGCTcagatcaccca_ | (SEQ ID NO: 103) |
| HLA B-up | 15267 | agGTGGATGCCCAGGacgagctttgagg_ | (SEQ ID NO: 104) |

TABLE 2-continued

Zinc finger target sites

| Target | SBS # | Target site | |
|---|---|---|---|
| HLA B-up | 15265 | agGGAGCAGAAGCAgcgcagcagcgcca_ | (SEQ ID NO: 105) |
| HLA B-up | 17454 | ctGGAGGTGGAtGCCCAGgacgagcttt_ | (SEQ ID NO: 106) |
| HLA B-up | 17456 | gaGCAGAAGCAGCGcagcagcgccacct_ | (SEQ ID NO: 107) |
| HLA C-down | 15296 | ccTCAGTTTCATGGGGAttcaagggaac_ | (SEQ ID NO: 108) |
| HLA C-down | 15298 | ccTAGGAGgTCATGGGCAtttgccatgc_ | (SEQ ID NO: 109) |
| HLA C-down | 25588 | tcGCGGCGtcGCTGTCGAAccgcacgaa_ | (SEQ ID NO: 110) |
| HLA C-down | 25589 | ccAAGAGGGGAGCCGCGggagccgtggg_ | (SEQ ID NO: 111) |

Class II

| DBP2-up | 15872 | gaAATAAGGCATACTGGtattactaatg_ | (SEQ ID NO: 112) |
| DBP2-up | 15873 | gaGGAGAGCAGGCCGATtacctgaccca_ | (SEQ ID NO: 113) |
| DRA-down | 15909 | tcTCCCAGGGTgGTTCAGtggcagaatt_ | (SEQ ID NO: 114) |
| DRA-down | 15910 | gcGGGGGAAAGaGAGGAGgagagaagga_ | (SEQ ID NO: 115) |

Regulators

| TAP1 | 28386 | agAAGGCTGTGGGCTCCtcagagaaaat_ | (SEQ ID NO: 116) |
| TAP1 | 28385 | acTCTGGGGTAGATGGAGAGcagtacct_ | (SEQ ID NO: 117) |
| TAP2 | 28394 | ttGCGGATCCGGGAGCAGCTtttctcct_ | (SEQ ID NO: 118) |
| TAP2 | 28393 | ttGATTCGaGACATGGTGTAGgtgaagc_ | (SEQ ID NO: 119) |
| Tapasin | 28406 | ccACAGCCAGAGCCtCAGCAGgagcctg_ | (SEQ ID NO: 120) |
| Tapasin | 28405 | cgCAAGAGGCTGGAGAGGCTgaggactg_ | (SEQ ID NO: 121) |
| Tapasin | 28404 | ctGGATGGGGCTTGGCTGATggtcagca_ | (SEQ ID NO: 122) |
| Tapasin | 28403 | gcCCGCGGGCAGTTcTGCGCGggggtca_ | (SEQ ID NO: 123) |
| CTIIA | 15486 | gcTCCCAGgCAGCGGGCGggaggctgga_ | (SEQ ID NO: 124) |
| CTIIA | 15487 | ctACTCGGGCCaTCGGCGgctgcctcgg_ | (SEQ ID NO: 125) |
| RFX5 | 15506 | ttGATGTCAGGGAAGATctctctgatga_ | (SEQ ID NO: 126) |
| RFX5 | 15507 | gcTCGAAGGCTTGGTGGCCGggccagt_ | (SEQ ID NO: 127) |

Others

| TRAC | 25539 | ttGTTGCTcCAGGCCACAGCActgttgc_ | (SEQ ID NO: 128) |
| TRAC | 25540 | ctGACTTTGCATGTGCAaacgccttcaa_ | (SEQ ID NO: 129) |
| TRBC | 16783 | ccGTAGAACTGGACTTGacagcggaagt_ | (SEQ ID NO: 130) |
| TRBC | 16787 | tcTCGGAGAATGACGAGTGGacccagga_ | (SEQ ID NO: 131) |

In some embodiments, the DNA binding domain is an engineered domain from a TAL effector similar to those derived from the plant pathogens Xanthomonas (see Boch et al, (2009) *Science* 326: 1509-1512 and Moscou and Bogdanove, (2009) *Science* 326: 1501) and Ralstonia (see Heuer et al (2007) *Applied and Environmental Microbiology* 73(13): 4379-4384); U.S. Patent Publication Nos. 20110301073 and 20110145940.

Fusion Proteins

Fusion proteins comprising DNA-binding proteins (e.g., ZFPs or TALEs) as described herein and a heterologous regulatory (functional) domain (or functional fragment thereof) are also provided. Common domains include, e.g., transcription factor domains (activators, repressors, co-activators, co-repressors), silencers, oncogenes (e.g., myc, jun, fos, myb, max, mad, rel, ets, bcl, myb, mos family members etc.); DNA repair enzymes and their associated factors and modifiers; DNA rearrangement enzymes and their associated factors and modifiers; chromatin associated proteins and their modifiers (e.g. kinases, acetylases and deacetylases); and DNA modifying enzymes (e.g., methyltransferases, topoisomerases, helicases, ligases, kinases, phosphatases, polymerases, endonucleases) and their associated factors and modifiers. U.S. Patent Application Publication Nos. 20050064474;

20060188987 and 2007/0218528 for details regarding fusions of DNA-binding domains and nuclease cleavage domains, incorporated by reference in their entireties herein Suitable domains for achieving activation include the HSV VP16 activation domain (see, e.g., Hagmann et al., *J. Virol.* 71, 5952-5962 (1997)) nuclear hormone receptors (see, e.g., Torchia et al., *Curr. Opin. Cell. Biol.* 10:373-383 (1998)); the p65 subunit of nuclear factor kappa B (Bitko & Barik, *J. Virol.* 72:5610-5618 (1998) and Doyle & Hunt, *Neuroreport* 8:2937-2942 (1997)); Liu et al., *Cancer Gene Ther.* 5:3-28 (1998)), or artificial chimeric functional domains such as VP64 (Beerli et al., (1998) *Proc. Natl. Acad. Sci. USA* 95:14623-33), and degron (Molinari et al., (1999) *EMBO J.* 18, 6439-6447). Additional exemplary activation domains include, Oct.1, Oct.-2A, Spl, AP-2, and CTF1 (Seipel et al., *EMBO J.* 11, 4961-4968 (1992) as well as p300, CBP, PCAF, SRC1 PvALF, AtHD2A and ERF-2. See, for example, Robyr et al. (2000) *Mol. Endocrinol.* 14:329-347; Collingwood et al. (1999) *J. Mol. Endocrinol.* 23:255-275; Leo et al. (2000) *Gene* 245:1-11; Manteuffel-Cymborowska (1999) *Acta Biochim. Pol.* 46:77-89; McKenna et al. (1999) *J. Steroid Biochem. Mol. Biol.* 69:3-12; Malik et al. (2000) *Trends Biochem. Sci.* 25:277-283; and Lemon et al. (1999) *Curr. Opin. Genet. Dev.* 9:499-504. Additional exemplary activation domains include, but are not limited to, OsGAI, HALF-1, C1, AP1, ARF-5,-6,-7, and -8, CPRF1, CPRF4, MYC-RP/GP, and TRAB1. See, for example, Ogawa et al. (2000) *Gene* 245:21-29; Okanami et al. (1996) *Genes Cells* 1:87-99; Goff et al. (1991) *Genes Dev.* 5:298-309; Cho et al. (1999) *Plant Mol. Biol.* 40:419-429; Ulmason et al. (1999) *Proc. Natl. Acad. Sci. USA* 96:5844-5849; Sprenger-Haussels et al. (2000) *Plant J.* 22:1-8; Gong et al. (1999) *Plant Mol. Biol.* 41:33-44; and Hobo et al. (1999) *Proc. Natl. Acad. Sci. USA* 96:15,348-15,353.

It will be clear to those of skill in the art that, in the formation of a fusion protein (or a nucleic acid encoding same) between a DNA-binding domain and a functional domain, either an activation domain or a molecule that interacts with an activation domain is suitable as a functional domain. Essentially any molecule capable of recruiting an activating complex and/or activating activity (such as, for example, histone acetylation) to the target gene is useful as an activating domain of a fusion protein. Insulator domains, localization domains, and chromatin remodeling proteins such as ISWI-containing domains and/or methyl binding domain proteins suitable for use as functional domains in fusion molecules are described, for example, in co-owned U.S. Patent Applications 2002/0115215 and 2003/0082552 and in co-owned WO 02/44376.

Exemplary repression domains include, but are not limited to, KRAB A/B, KOX, TGF-beta-inducible early gene (TIEG), v-erbA, SID, MBD2, MBD3, members of the DNMT family (e.g., DNMT1, DNMT3A, DNMT3B), Rb, and MeCP2. See, for example, Bird et al. (1999) *Cell* 99:451-454; Tyler et al. (1999) *Cell* 99:443-446; Knoepfler et al. (1999) *Cell* 99:447-450; and Robertson et al. (2000) *Nature Genet.* 25:338-342. Additional exemplary repression domains include, but are not limited to, ROM2 and AtHD2A. See, for example, Chem et al. (1996) *Plant Cell* 8:305-321; and Wu et al. (2000) *Plant J.* 22:19-27.

Fusion molecules are constructed by methods of cloning and biochemical conjugation that are well known to those of skill in the art. Fusion molecules comprise a DNA-binding domain and a functional domain (e.g., a transcriptional activation or repression domain). Fusion molecules also optionally comprise nuclear localization signals (such as, for example, that from the SV40 medium T-antigen) and epitope tags (such as, for example, FLAG and hemagglutinin). Fusion proteins (and nucleic acids encoding them) are designed such that the translational reading frame is preserved among the components of the fusion.

Fusions between a polypeptide component of a functional domain (or a functional fragment thereof) on the one hand, and a non-protein DNA-binding domain (e.g., antibiotic, intercalator, minor groove binder, nucleic acid) on the other, are constructed by methods of biochemical conjugation known to those of skill in the art. See, for example, the Pierce Chemical Company (Rockford, IL) Catalogue. Methods and compositions for making fusions between a minor groove binder and a polypeptide have been described. Mapp et al. (2000) *Proc. Natl. Acad. Sci. USA* 97:3930-3935.

In certain embodiments, the target site bound by the zinc finger protein is present in an accessible region of cellular chromatin. Accessible regions can be determined as described, for example, in co-owned International Publication WO 01/83732. If the target site is not present in an accessible region of cellular chromatin, one or more accessible regions can be generated as described in co-owned WO 01/83793. In additional embodiments, the DNA-binding domain of a fusion molecule is capable of binding to cellular chromatin regardless of whether its target site is in an accessible region or not. For example, such DNA-binding domains are capable of binding to linker DNA and/or nucleosomal DNA. Examples of this type of "pioneer" DNA binding domain are found in certain steroid receptor and in hepatocyte nuclear factor 3 (HNF3). Cordingley et al. (1987) *Cell* 48:261-270; Pina et al. (1990) *Cell* 60:719-731; and Cirillo et al. (1998) *EMBO J.* 17:244-254.

The fusion molecule may be formulated with a pharmaceutically acceptable carrier, as is known to those of skill in the art. See, for example, Remington's Pharmaceutical Sciences, 17th ed., 1985; and co-owned WO 00/42219.

The functional component/domain of a fusion molecule can be selected from any of a variety of different components capable of influencing transcription of a gene once the fusion molecule binds to a target sequence via its DNA binding domain. Hence, the functional component can include, but is not limited to, various transcription factor domains, such as activators, repressors, co-activators, co-repressors, and silencers.

Additional exemplary functional domains are disclosed, for example, in co-owned U.S. Pat. No. 6,534,261 and U.S. Patent Application Publication No. 2002/0160940.

Functional domains that are regulated by exogenous small molecules or ligands may also be selected. For example, RheoSwitch® technology may be employed wherein a functional domain only assumes its active conformation in the presence of the external RheoChem™ ligand (see for example US 20090136465). Thus, the ZFP may be operably linked to the regulatable functional domain wherein the resultant activity of the ZFP-TF is controlled by the external ligand.

Nucleases

In certain embodiments, the fusion protein comprises a DNA-binding binding domain and cleavage (nuclease) domain. As such, gene modification can be achieved using a nuclease, for example an engineered nuclease. Engineered nuclease technology is based on the engineering of naturally occurring DNA-binding proteins. For example, engineering of homing endonucleases with tailored DNA-binding specificities has been described. Chames et al. (2005) *Nucleic Acids Res* 33(20):e178; Arnould et al. (2006) *J. Mol. Biol.* 355:443-458. In addition, engineering of ZFPs has also been described. See, e.g., U.S. Pat. Nos. 6,534,261; 6,607,882; 6,824,978; 6,979,539; 6,933,113; 7,163,824; and 7,013,219.

In addition, ZFPs and/or TALEs have been fused to nuclease domains to create ZFNs and TALENs—a functional entity that is able to recognize its intended nucleic acid target through its engineered (ZFP or TALE) DNA binding domain and cause the DNA to be cut near the DNA binding site via the nuclease activity. See, e.g., Kim et al. (1996) *Proc Nat'l Acad Sci USA* 93(3):1156-1160. More recently, such nucleases have been used for genome modification in a variety of organisms. See, for example, United States Patent Publications 20030232410; 20050208489; 20050026157; 20050064474; 20060188987; 20060063231; and International Publication WO 07/014275.

Thus, the methods and compositions described herein are broadly applicable and may involve any nuclease of interest. Non-limiting examples of nucleases include meganucleases, TALENs and zinc finger nucleases. The nuclease may comprise heterologous DNA-binding and cleavage domains (e.g., zinc finger nucleases; meganuclease DNA-binding domains with heterologous cleavage domains) or, alternatively, the DNA-binding domain of a naturally-occurring nuclease may be altered to bind to a selected target site (e.g., a meganuclease that has been engineered to bind to site different than the cognate binding site).

In certain embodiments, the nuclease is a meganuclease (homing endonuclease). Naturally-occurring meganucleases recognize 15-40 base-pair cleavage sites and are commonly grouped into four families: the LAGLIDADG (SEQ ID NO: 141) family, the GIY-YIG family, the His-Cyst box family and the HNH family. Exemplary homing endonucleases include I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII. Their recognition sequences are known. See also U.S. Pat. Nos. 5,420,032; 6,833,252; Belfort et al. (1997) *Nucleic Acids Res.* 25:3379-3388; Dujon et al. (1989) *Gene* 82:115-118; Perler et al. (1994) *Nucleic Acids Res.* 22, 1125-1127; Jasin (1996) *Trends Genet.* 12:224-228; Gimble et al. (1996) *J. Mol. Biol.* 263:163-180; Argast et al. (1998) *J. Mol. Biol.* 280:345-353 and the New England Biolabs catalogue.

DNA-binding domains from naturally-occurring meganucleases, primarily from the LAGLIDADG (SEQ ID NO: 141) family, have been used to promote site-specific genome modification in plants, yeast, Drosophila, mammalian cells and mice, but this approach has been limited to the modification of either homologous genes that conserve the meganuclease recognition sequence (Monet et al. (1999), *Biochem. Biophysics. Res. Common.* 255: 88-93) or to pre-engineered genomes into which a recognition sequence has been introduced (Route et al. (1994), *Mol. Cell. Biol.* 14: 8096-106; Chilton et al. (2003), *Plant Physiology.* 133: 956-65; Puchta et al. (1996), *Proc. Natl. Acad. Sci. USA* 93: 5055-60; Rong et al. (2002), *Genes Dev.* 16: 1568-81; Gouble et al. (2006), *J. Gene Med.* 8(5):616-622). Accordingly, attempts have been made to engineer meganucleases to exhibit novel binding specificity at medically or biotechnologically relevant sites (Porteus et al. (2005), *Nat. Biotechnol.* 23: 967-73; Sussman et al. (2004), *J. Mol. Biol.* 342: 31-41; Epinat et al. (2003), *Nucleic Acids Res.* 31: 2952-62; Chevalier et al. (2002) *Molec. Cell* 10:895-905; Epinat et al. (2003) *Nucleic Acids Res.* 31:2952-2962; Ashworth et al. (2006) *Nature* 441:656-659; Paques et al. (2007) *Current Gene Therapy* 7:49-66; U.S. Patent Publication Nos. 20070117128; 20060206949; 20060153826; 20060078552; and 20040002092). In addition, naturally-occurring or engineered DNA- binding domains from meganucleases have also been operably linked with a cleavage domain from a heterologous nuclease (e.g., FokI).

In other embodiments, the nuclease is a zinc finger nuclease (ZFN) or TALE DNA binding domain-nuclease fusion (TALEN). ZFNs and TALENs comprise a DNA binding domain (zinc finger protein or TALE DNA binding domain) that has been engineered to bind to a target site in a gene of choice and cleavage domain or a cleavage half-domain As described in detail above, zinc finger binding domains and TALE DNA binding domains can be engineered to bind to a sequence of choice. See, for example, Beerli et al. (2002) *Nature Biotechnol.* 20:135-141; Pabo et al. (2001) *Ann. Rev. Biochem.* 70:313-340; Isalan et al. (2001) *Nature Biotechnol.* 19:656-660; Segal et al. (2001) *Curr. Opin. Biotechnol.* 12:632-637; Choo et al. (2000) *Curr. Opin. Struct. Biol.* 10:411-416. An engineered zinc finger binding domain or TALE protein can have a novel binding specificity, compared to a naturally-occurring protein. Engineering methods include, but are not limited to, rational design and various types of selection. Rational design includes, for example, using databases comprising triplet (or quadruplet) nucleotide sequences and individual zinc finger or TALE amino acid sequences, in which each triplet or quadruplet nucleotide sequence is associated with one or more amino acid sequences of zinc fingers or TALE repeat units which bind the particular triplet or quadruplet sequence. See, for example, co-owned U.S. Pat. Nos. 6,453,242 and 6,534,261, incorporated by reference herein in their entireties.

Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237. In addition, enhancement of binding specificity for zinc finger binding domains has been described, for example, in co-owned WO 02/077227.

Selection of target sites; and methods for design and construction of fusion proteins (and polynucleotides encoding same) are known to those of skill in the art and described in detail in U.S. Patent Application Publication Nos. 20050064474 and 20060188987, incorporated by reference in their entireties herein.

In addition, as disclosed in these and other references, zinc finger domains, TALEs and/or multi-fingered zinc finger proteins may be linked together using any suitable linker sequences, including for example, linkers of 5 or more amino acids in length. (e.g., TGEKP (SEQ ID NO:131), TGGQRP (SEQ ID NO:132), TGQKP (SEQ ID NO:133), and/or TGSQKP (SEQ ID NO:134)). See, e.g., U.S. Pat. Nos. 6,479,626; 6,903,185; and 7,153,949 for exemplary linker sequences 6 or more amino acids in length. The proteins described herein may include any combination of suitable linkers between the individual zinc fingers of the protein. See, also, U.S. Patent Publication No. 20110287512.

Nucleases such as ZFNs, TALENs and/or meganucleases also comprise a nuclease (cleavage domain, cleavage half-domain). As noted above, the cleavage domain may be heterologous to the DNA-binding domain, for example a zinc finger DNA-binding domain and a cleavage domain from a nuclease or a meganuclease DNA-binding domain and cleavage domain from a different nuclease. Heterologous cleavage domains can be obtained from any endonuclease or exonuclease. Exemplary endonucleases from which a cleavage domain can be derived include, but are not limited to, restriction endonucleases and homing endonucleases. See, for example, 2002-2003 Catalogue, New England Biolabs, Beverly, Mass.; and Belfort et al. (1997) *Nucleic Acids Res.* 25:3379-3388. Additional enzymes which cleave DNA are known (e.g., S1 Nuclease; mung bean nuclease; pancreatic DNase I; micrococcal nuclease; yeast HO endonuclease; see also Linn et al. (eds.) *Nucleases*, Cold Spring Harbor Laboratory Press,1993). One or more of these enzymes (or functional fragments thereof) can be used as a source of cleavage domains and cleavage half-domains.

Similarly, a cleavage half-domain can be derived from any nuclease or portion thereof, as set forth above, that requires dimerization for cleavage activity. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However any integral number of nucleotides or nucleotide pairs can intervene between two target sites (e.g., from 2 to 50 nucleotide pairs or more). In general, the site of cleavage lies between the target sites.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme Fok I catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) *Proc. Natl. Acad. Sci. USA* 89:4275-4279; Li et al. (1993) *Proc. Natl. Acad. Sci. USA* 90:2764-2768; Kim et al. (1994a) *Proc. Natl. Acad. Sci. USA* 91:883-887; Kim et al. (1994b) *J. Biol. Chem.* 269:31,978-31,982. Thus, in one embodiment, fusion proteins comprise the cleavage domain (or cleavage half-domain) from at least one Type IIS restriction enzyme and one or more zinc finger binding domains, which may or may not be engineered.

An exemplary Type IIS restriction enzyme, whose cleavage domain is separable from the binding domain, is Fok I. This particular enzyme is active as a dimer. Bitinaite et al. (1998) *Proc. Natl. Acad. Sci. USA* 95: 10,570-10,575. Accordingly, for the purposes of the present disclosure, the portion of the Fok I enzyme used in the disclosed fusion proteins is considered a cleavage half-domain. Thus, for targeted double-stranded cleavage and/or targeted replacement of cellular sequences using zinc finger-Fok I fusions, two fusion proteins, each comprising a FokI cleavage half-domain, can be used to reconstitute a catalytically active cleavage domain. Alternatively, a single polypeptide molecule containing a zinc finger binding domain and two Fok I cleavage half-domains can also be used. Parameters for targeted cleavage and targeted sequence alteration using zinc finger-Fok I fusions are provided elsewhere in this disclosure.

A cleavage domain or cleavage half-domain can be any portion of a protein that retains cleavage activity, or that retains the ability to multimerize (e.g., dimerize) to form a functional cleavage domain.

Exemplary Type IIS restriction enzymes are described in International Publication WO 07/014275, incorporated herein in its entirety. Additional restriction enzymes also contain separable binding and cleavage domains, and these are contemplated by the present disclosure. See, for example, Roberts et al. (2003) *Nucleic Acids Res.* 31:418-420.

In certain embodiments, the cleavage domain comprises one or more engineered cleavage half-domain (also referred to as dimerization domain mutants) that minimize or prevent homodimerization, as described, for example, in U.S. Patent Publication Nos. 20050064474, 20060188987 and 20080131962, the disclosures of all of which are incorporated by reference in their entireties herein. Amino acid residues at positions 446, 447, 479, 483, 484, 486, 487, 490, 491, 496, 498, 499, 500, 531, 534, 537, and 538 of Fok I are all targets for influencing dimerization of the Fok I cleavage half-domains.

Exemplary engineered cleavage half-domains of Fok I that form obligate heterodimers include a pair in which a first cleavage half-domain includes mutations at amino acid residues at positions 490 and 538 of Fok I and a second cleavage half-domain includes mutations at amino acid residues 486 and 499.

Thus, in one embodiment, a mutation at 490 replaces Glu (E) with Lys (K); the mutation at 538 replaces Iso (I) with Lys (K); the mutation at 486 replaced Gln (Q) with Glu (E); and the mutation at position 499 replaces Iso (I) with Lys (K). Specifically, the engineered cleavage half-domains described herein were prepared by mutating positions 490 (E→K) and 538 (I→K) in one cleavage half-domain to produce an engineered cleavage half-domain designated "E490K:I538K" and by mutating positions 486 (Q→E) and 499 (I→L) in another cleavage half-domain to produce an engineered cleavage half-domain designated "Q486E:I499L". The engineered cleavage half-domains described herein are obligate heterodimer mutants in which aberrant cleavage is minimized or abolished. See, e.g., U.S. Patent Publication No. 2008/0131962, the disclosure of which is incorporated by reference in its entirety for all purposes. In certain embodiments, the engineered cleavage half-domain comprises mutations at positions 486, 499 and 496 (numbered relative to wild-type FokI), for instance mutations that replace the wild type Gln (Q) residue at position 486 with a Glu (E) residue, the wild type Iso (I) residue at position 499 with a Leu (L) residue and the wild-type Asn (N) residue at position 496 with an Asp (D) or Glu (E) residue (also referred to as a "ELD" and "ELE" domains, respectively). In other embodiments, the engineered cleavage half-domain comprises mutations at positions 490, 538 and 537 (numbered relative to wild-type FokI), for instance mutations that replace the wild type Glu (E) residue at position 490 with a Lys (K) residue, the wild type Iso (I) residue at position 538 with a Lys (K) residue, and the wild-type His (H) residue at position 537 with a Lys (K) residue or a Arg (R) residue (also referred to as "KKK" and "KKR" domains, respectively). In other embodiments, the engineered cleavage half-domain comprises mutations at positions 490 and 537 (numbered relative to wild-type FokI), for instance mutations that replace the wild type Glu (E) residue at position 490 with a Lys (K) residue and the wild-type His (H) residue at position 537 with a Lys (K) residue or a Arg (R) residue (also referred to as "KIK" and "KIR" domains, respectively). (See U.S. Patent Publication No. 20110201055).

Engineered cleavage half-domains described herein can be prepared using any suitable method, for example, by site-directed mutagenesis of wild-type cleavage half-domains (Fok I) as described in U.S. Patent Publication Nos. 20050064474 and 20080131962.

Alternatively, nucleases may be assembled in vivo at the nucleic acid target site using so-called "split-enzyme" technology (see e.g. U.S. Patent Publication No. 20090068164). Components of such split enzymes may be expressed either on separate expression constructs, or can be linked in one open reading frame where the individual components are separated, for example, by a self-cleaving 2A peptide or IRES sequence. Components may be individual zinc finger binding domains or domains of a meganuclease nucleic acid binding domain.

Nucleases (e.g., ZFNs and/or TALENs) can be screened for activity prior to use, for example in a yeast-based chromosomal system as described in WO 2009/042163 and U.S. Patent Publication No. 20090068164. Nuclease expression constructs can be readily designed using methods known in the art. See, e.g., United States Patent Publications 20030232410; 20050208489; 20050026157; 20050064474; 20060188987; 20060063231; and International Publication WO 07/014275. Expression of the nuclease may be under the control of a constitutive promoter or an inducible promoter, for example the galactokinase promoter which is activated (de-repressed) in the presence of raffinose and/or galactose and repressed in presence of glucose.

Delivery

The proteins (e.g., ZFPs, TALEs, ZFNs and/or TALENs), polynucleotides encoding same and compositions comprising the proteins and/or polynucleotides described herein may be delivered to a target cell by any suitable means, including, for example, by injection of the protein or mRNA. Suitable cells include but not limited to eukaryotic and prokaryotic cells and/or cell lines. Non-limiting examples of such cells or cell lines generated from such cells include T-cells, COS, CHO (e.g., CHO—S, CHO—K1, CHO-DG44, CHO-DUXB11, CHO-DUKX, CHOK1SV), VERO, MDCK, WI38, V79, B14AF28-G3, BHK, HaK, NSO, SP2/0-Ag14, HeLa, HEK293 (e.g., HEK293-F, HEK293-H, HEK293-T), and perC6 cells as well as insect cells such as *Spodoptera fugiperda* (Sf), or fungal cells such as *Saccharomyces, Pichia* and *Schizosaccharomyces*. In certain embodiments, the cell line is a CHO—K1, MDCK or HEK293 cell line. Suitable cells also include stem cells such as, by way of example, embryonic stem cells, induced pluripotent stem cells (iPS cells), hematopoietic stem cells, neuronal stem cells and mesenchymal stem cells.

Methods of delivering proteins comprising DNA-binding domains as described herein are described, for example, in U.S. Pat. Nos. 6,453,242; 6,503,717; 6,534,261; 6,599,692; 6,607,882; 6,689,558; 6,824,978; 6,933,113; 6,979,539; 7,013,219; and 7,163,824, the disclosures of all of which are incorporated by reference herein in their entireties.

DNA binding domains and fusion proteins comprising these DNA binding domains as described herein may also be delivered using vectors containing sequences encoding one or more of the DNA-binding protein(s). Additionally, donor nucleic acids also may be delivered via these vectors. Any vector systems may be used including, but not limited to, plasmid vectors, retroviral vectors, lentiviral vectors, adenovirus vectors, poxvirus vectors; herpesvirus vectors and adeno-associated virus vectors, etc. See, also, U.S. Pat. Nos. 6,534,261; 6,607,882; 6,824,978; 6,933,113; 6,979,539; 7,013,219; and 7,163,824, incorporated by reference herein in their entireties. Furthermore, it will be apparent that any of these vectors may comprise one or more DNA-binding protein-encoding sequences and/or donor nucleic acids as appropriate. Thus, when one or more DNA-binding proteins as described herein are introduced into the cell, and donor DNAs as appropriate, they may be carried on the same vector or on different vectors. When multiple vectors are used, each vector may comprise a sequence encoding one or multiple DNA-binding proteins and donor nucleic acids as desired.

Conventional viral and non-viral based gene transfer methods can be used to introduce nucleic acids encoding engineered DNA-binding proteins in cells (e.g., mammalian cells) and target tissues and to co-introduce donors as desired. Such methods can also be used to administer nucleic acids encoding DNA-binding proteins to cells in vitro. In certain embodiments, nucleic acids encoding DNA-binding proteins s are administered for in vivo or ex vivo gene therapy uses. Non-viral vector delivery systems include DNA plasmids, naked nucleic acid, and nucleic acid complexed with a delivery vehicle such as a liposome or poloxamer. Viral vector delivery systems include DNA and RNA viruses, which have either episomal or integrated genomes after delivery to the cell. For a review of gene therapy procedures, see Anderson, *Science* 256:808-813 (1992); Nabel & Felgner, *TIBTECH* 11:211-217 (1993); Mitani & Caskey, *TIBTECH* 11:162-166 (1993); Dillon, *TIBTECH* 11:167-175 (1993); Miller, *Nature* 357:455-460 (1992); Van Brunt, *Biotechnology* 6(10):1149-1154 (1988); Vigne, *Restorative Neurology and Neuroscience* 8:35-36 (1995); Kremer & Perricaudet, *British Medical Bulletin* 51(1):31-44 (1995); Haddada et al., in *Current Topics in Microbiology and Immunology* Doerfler and Böhm (eds.) (1995); and Yu et al., *Gene Therapy* 1:13-26 (1994).

Methods of non-viral delivery of nucleic acids include electroporation, lipofection, microinjection, biolistics, virosomes, liposomes, immunoliposomes, polycation or lipid:nucleic acid conjugates, naked DNA, artificial virions, and agent-emjamced enhanced uptake of DNA. Sonoporation using, e.g., the Sonitron 2000 system (Rich-Mar) can also be used for delivery of nucleic acids.

Additional exemplary nucleic acid delivery systems include those provided by Amaxa Biosystems (Cologne, Germany), Maxcyte, Inc. (Rockville, Md.), BTX Molecular Delivery Systems (Holliston, Mass.) and Copernicus Therapeutics Inc, (see for example U.S. Pat. No. 6,008,336). Lipofection is described in e.g., U.S. Pat. No. 5,049,386, U.S. Pat. No. 4,946,787; and U.S. Pat. No. 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424, WO 91/16024. Delivery can be to cells (ex vivo administration) or target tissues (in vivo administration).

The preparation of lipid:nucleic acid complexes, including targeted liposomes such as immunolipid complexes, is well known to one of skill in the art (see, e.g., Crystal, *Science* 270:404-410 (1995); Blaese et al., *Cancer Gene Ther.* 2:291-297 (1995); Behr et al., *Bioconjugate Chem.* 5:382-389 (1994); Remy et al., *Bioconjugate Chem.* 5:647-654 (1994); Gao et al., *Gene Therapy* 2:710-722 (1995); Ahmad et al., *Cancer Res.* 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

Additional methods of delivery include the use of packaging the nucleic acids to be delivered into EnGeneIC delivery vehicles (EDVs). These EDVs are specifically delivered to target tissues using bispecific antibodies where one arm of the antibody has specificity for the target tissue and the other has specificity for the EDV. The antibody brings the EDVs to the target cell surface and then the EDV is brought into the cell by endocytosis. Once in the cell, the contents are released (see MacDiarmid et al (2009) *Nature Biotechnology* vol 27(7) p. 643).

The use of RNA or DNA viral based systems for the delivery of nucleic acids encoding engineered DNA-binding proteins and donors as desired takes advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of DNA-binding proteins and donors include, but are not limited to, retroviral, lentivirus, adenoviral, adeno-associated, vaccinia and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system depends on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immunodeficiency virus (SIV), human immunodeficiency virus (HIV), and combinations thereof (see, e.g., Buchscher et al., *J. Virol.* 66:2731-2739 (1992); Johann et al., *J. Virol.* 66:1635-1640 (1992); Sommerfelt et al., *Virol.* 176:58-59 (1990); Wilson et al., *J. Virol.* 63:2374-2378 (1989); Miller et al., *J. Virol.* 65:2220-2224 (1991); PCT/US94/05700).

In applications in which transient expression is preferred, adenoviral based systems can be used. Adenoviral based vectors are capable of very high transduction efficiency in many cell types and do not require cell division. With such vectors, high titer and high levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al., *Virology* 160:38-47 (1987); U.S. Pat. No. 4,797,368; WO 93/24641; Kotin, *Human Gene Therapy* 5:793-801 (1994); Muzyczka, *J. Clin. Invest.* 94:1351 (1994). Construction of recombinant AAV vectors are described in a number of publications, including U.S. Pat. No. 5,173,414; Tratschin et al., *Mol. Cell. Biol.* 5:3251-3260 (1985); Tratschin, et al., *Mol. Cell. Biol.* 4:2072-2081 (1984); Hermonat & Muzyczka, *PNAS* 81:6466-6470 (1984); and Samulski et al., *J. Virol.* 63:03822-3828 (1989).

At least six viral vector approaches are currently available for gene transfer in clinical trials, which utilize approaches that involve complementation of defective vectors by genes inserted into helper cell lines to generate the transducing agent.

pLASN and MFG-S are examples of retroviral vectors that have been used in clinical trials (Dunbar et al., *Blood* 85:3048-305 (1995); Kohn et al., *Nat. Med.* 1:1017-102 (1995); Malech et al., *PNAS* 94:22 12133-12138 (1997)). PA317/pLASN was the first therapeutic vector used in a gene therapy trial. (Blaese et al., *Science* 270:475-480 (1995)). Transduction efficiencies of 50% or greater have been observed for MFG-S packaged vectors. (Ellem et al., *Immunol Immunother.* 44(1):10-20 (1997); Dranoff et al., *Hum. Gene Ther.* 1:111-2 (1997).

Recombinant adeno-associated virus vectors (rAAV) are a promising alternative gene delivery systems based on the defective and nonpathogenic parvovirus adeno-associated type 2 virus. All vectors are derived from a plasmid that retains only the AAV 145 by inverted terminal repeats flanking the transgene expression cassette. Efficient gene transfer and stable transgene delivery due to integration into the genomes of the transduced cell are key features for this vector system. (Wagner et al., *Lancet* 351:9117 1702-3 (1998), Kearns et al., *Gene Ther.* 9:748-55 (1996)). Other AAV serotypes, including AAV1, AAV3, AAV4, AAV5, AAV6, AAV8, AAV9 and AAV10 can also be used in accordance with the present invention.

Replication-deficient recombinant adenoviral vectors (Ad) can be produced at high titer and readily infect a number of different cell types. Most adenovirus vectors are engineered such that a transgene replaces the Ad E1a, E1b, and/or E3 genes; subsequently the replication defective vector is propagated in human 293 cells that supply deleted gene function in trans. Ad vectors can transduce multiple types of tissues in vivo, including nondividing, differentiated cells such as those found in liver, kidney and muscle. Conventional Ad vectors have a large carrying capacity. An example of the use of an Ad vector in a clinical trial involved polynucleotide therapy for antitumor immunization with intramuscular injection (Sterman et al., *Hum. Gene Ther.* 7:1083-9 (1998)). Additional examples of the use of adenovirus vectors for gene transfer in clinical trials include Rosenecker et al., *Infection* 24:1 5-10 (1996); Sterman et al., *Hum. Gene Ther.* 9:7 1083-1089 (1998); Welsh et al., *Hum. Gene Ther.* 2:205-18 (1995); Alvarez et al., *Hum. Gene Ther.* 5:597-613 (1997); Topf et al., *Gene Ther.* 5:507-513 (1998); Sterman et al., *Hum. Gene Ther.* 7:1083-1089 (1998).

Packaging cells are used to form virus particles that are capable of infecting a host cell. Such cells include 293 cells, which package adenovirus, and ψ2 cells or PA317 cells, which package retrovirus. Viral vectors used in gene therapy are usually generated by a producer cell line that packages a nucleic acid vector into a viral particle. The vectors typically contain the minimal viral sequences required for packaging and subsequent integration into a host (if applicable), other viral sequences being replaced by an expression cassette encoding the protein to be expressed. The missing viral functions are supplied in trans by the packaging cell line. For example, AAV vectors used in gene therapy typically only possess inverted terminal repeat (ITR) sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In many gene therapy applications, it is desirable that the gene therapy vector be delivered with a high degree of specificity to a particular tissue type. Accordingly, a viral vector can be modified to have specificity for a given cell type by expressing a ligand as a fusion protein with a viral coat protein on the outer surface of the virus. The ligand is chosen to have affinity for a receptor known to be present on the cell type of interest. For example, Han et al., *Proc. Natl. Acad. Sci. USA* 92:9747-9751 (1995), reported that Moloney murine leukemia virus can be modified to express human heregulin fused to gp70, and the recombinant virus infects certain human breast cancer cells expressing human epidermal growth factor receptor. This principle can be extended to other virus-target cell pairs, in which the target cell expresses a receptor and the virus expresses a fusion protein comprising a ligand for the cell-surface receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences which favor uptake by specific target cells.

Gene therapy vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by re-implantation of the cells into a patient, usually after selection for cells which have incorporated the vector.

Ex vivo cell transfection for diagnostics, research, transplant or for gene therapy (e.g., via re-infusion of the transfected cells into the host organism) is well known to those of skill in the art. In a preferred embodiment, cells are isolated from the subject organism, transfected with a DNA-binding proteins nucleic acid (gene or cDNA), and re-infused back into the subject organism (e.g., patient). Various cell types suitable for ex vivo transfection are well known to those of skill in the art (see, e.g., Freshney et al., *Culture of Animal Cells, A Manual of Basic Technique* (3rd ed. 1994)) and the references cited therein for a discussion of how to isolate and culture cells from patients).

In one embodiment, stem cells are used in ex vivo procedures for cell transfection and gene therapy. The advantage to using stem cells is that they can be differentiated into other cell types in vitro, or can be introduced into a mammal (such as the donor of the cells) where they will engraft in the bone marrow. Methods for differentiating CD34+ cells in vitro into clinically important immune cell types using cytokines such a GM-CSF, IFN-γ and TNF-α are known (see Inaba et al., *J. Exp. Med.* 176:1693-1702 (1992)).

Stem cells are isolated for transduction and differentiation using known methods. For example, stem cells are isolated from bone marrow cells by panning the bone marrow cells with antibodies which bind unwanted cells, such as CD4+ and CD8+ (T cells), CD45+ (panB cells), GR-1 (granulocytes), and Tad (differentiated antigen presenting cells) (see Inaba et al., *J. Exp. Med.* 176:1693-1702 (1992)).

Stem cells that have been modified may also be used in some embodiments. For example, neuronal stem cells that have been made resistant to apoptosis may be used as therapeutic compositions where the stem cells also contain the ZFP TFs of the invention. Resistance to apoptosis may come about, for example, by knocking out BAX and/or BAK using BAX- or BAK-specific ZFNs (see, U.S. patent application Ser. No. 12/456,043) in the stem cells, or those that are disrupted in a caspase, again using caspase-6 specific ZFNs for example. These cells can be transfected with the ZFP TFs that are known to regulate HLA.

Vectors (e.g., retroviruses, adenoviruses, liposomes, etc.) containing therapeutic DNA-binding proteins (or nucleic acids encoding these proteins) can also be administered directly to an organism for transduction of cells in vivo. Alternatively, naked DNA can be administered. Administration is by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another route.

Methods for introduction of DNA into hematopoietic stem cells are disclosed, for example, in U.S. Pat. No. 5,928,638. Vectors useful for introduction of transgenes into hematopoietic stem cells, e.g., CD34+ cells, include adenovirus Type 35.

Vectors suitable for introduction of transgenes into immune cells (e.g., T-cells) include non-integrating lentivirus vectors. See, for example, Ory et al. (1996) *Proc. Natl. Acad. Sci. USA* 93:11382-11388; Dull et al. (1998) *J. Virol.* 72:8463-8471; Zuffery et al. (1998) *J. Virol.* 72:9873-9880; Follenzi et al. (2000) *Nature Genetics* 25:217-222.

Pharmaceutically acceptable carriers are determined in part by the particular composition being administered, as well as by the particular method used to administer the composition. Accordingly, there is a wide variety of suitable formulations of pharmaceutical compositions available, as described below (see, e.g., *Remington's Pharmaceutical Sciences*, 17th ed., 1989).

As noted above, the disclosed methods and compositions can be used in any type of cell including, but not limited to, prokaryotic cells, fungal cells, Archaeal cells, plant cells, insect cells, animal cells, vertebrate cells, mammalian cells and human cells, including T-cells and stem cells of any type. Suitable cell lines for protein expression are known to those of skill in the art and include, but are not limited to COS, CHO (e.g., CHO—S, CHO—K1, CHO-DG44, CHO-DUXB11), VERO, MDCK, WI38, V79, B14AF28-G3, BHK, HaK, NS0, SP2/0-Ag14, HeLa, HEK293 (e.g., HEK293-F, HEK293-H, HEK293-T), perC6, insect cells such as *Spodoptera fugiperda* (Sf), and fungal cells such as *Saccharomyces, Pichia* and *Schizosaccharomyces*. Progeny, variants and derivatives of these cell lines can also be used.

Applications

The disclosed compositions and methods can be used for any application in which it is desired to modulate HLA genes and/or HLA regulators. In particular, these methods and compositions can be used where modulation or modification of a HLA allele is desired, including but not limited to, therapeutic and research applications.

Diseases and conditions which are tied to HLA include Addison's disease, ankylosing spondylitis, Behçet's disease, Buerger's disease, celiac disease, chronic active hepatitis, Graves' disease, juvenile rheumatoid arthritis, psoriasis, psoriatic arthritis, rheumatoid arthritis, Sjögren syndrome, and lupus erythematosus, among others. In addition, modification of a HLA gene may be useful in conjunction with other genetic modifications of a cell of interest. For example, modification of a target cell such as a CTL with a chimeric antigen receptor to change the CTL's specificity may be combined with HLA modification ex vivo in order to develop a cell therapeutic that may be used in most any patient in need thereof.

In addition, the materials and methods of the invention can be used in the treatment, prevention or amelioration of graft-versus-host-disease. Graft-versus-host disease (GVHD) is a common complication when allogenic T-cells (e.g., bone marrow and/or blood transfusion) are administered to a patient. The functional immune cells in the infused material recognize the recipient as "foreign" and mount an immunologic attack. By modulating HLA and/or TCR expression in allogenic T cells, "off the shelf" T cells (e.g., CD19-specific T-cells) can be administered on demand as "drugs" because the risk of GVHD is reduced or eliminated.

Methods and compositions also include stem cell compositions wherein a copy of a HLA allele within the stem cells has been modified using a HLA-specific or HLA regulator specific ZFN. For example, HLA modified hematopoietic stem cells can be introduced into a patient following bone marrow ablation. These altered HSC would allow the re-colonization of the patient without loss of the graft due to rejection. The introduced cells may also have other alterations to help during subsequent therapy (e.g., chemotherapy resistance) to treat the underlying disease.

The methods and compositions of the invention are also useful for the development of HLA modified platelets, for example for use as therapeutics. Thus, HLA modified platelets may be used to treat thrombocytopenic disorders such as idiopathic thrombocytopenic purpura, thrombotic thrombocytopenic purpura and drug-induced thrombocytopenic purpura (e.g. heparin-induced thrombocytopenia). Other platelet disorders that may be treated with the HLA modified platelets of the invention include Gaucher's disease, aplastic anemia, Onyalai, fetomaternal alloimmune thrombocytopenia, HELLP syndrome, cancer and side effects from some chemotherapeutic agents. The HLA modified platelets also have use in as an "off the shelf" therapy in emergency room situations with trauma patients.

The methods and compositions of the invention can be used in xenotransplantation. Specifically, by way of example only, pig organs can be used for transplantation into humans wherein the porcine MHC genes have been deleted and/or replaced with human HLA genes. Strains of pigs can be developed (from pig embryos that have had HLA targeting ZFNs encoded by mRNAs injected into them such that the endogenous MHC genes are disrupted, or from somatic cell nuclear transfer into pig embryos using nuclei of cells that have been successfully had their HLA genes targeted) that contain these useful genetic mutations, and these animals may be grown for eventual organ harvest. This will prevent rejection of these organs in humans and increase the chances for successful transplantation.

The methods and compositions of the invention are also useful for the design and implementation of in vitro and in vivo models, for example, animal models of HLA or other disorders, which allows for the study of these disorders.

EXAMPLES

Example 1

Design, Construction and General Characterization of Zinc Finger Protein Nucleases (ZFN)

Zinc finger proteins were designed and incorporated into plasmids or adenoviral vectors essentially as described in Urnov et al. (2005) *Nature* 435(7042):646-651, Perez et al (2008) *Nature Biotechnology* 26(7):808-816, and as described in U.S. Pat. No. 6,534,261. In addition, see U.S. Patent Publication 20110158957 for ZFNs targeted to TRAC and TRBC. Table 1 shows the recognition helices within the DNA binding domain of exemplary ZFPs while Table 2 shows the target sites for these ZFPs. Nucleotides in the target site that are contacted by the ZFP recognition helices are indicated in uppercase letters; non-contacted nucleotides indicated in lowercase.

Example 2

ZFNs Specific for HLA Class I Genes

The HLA complexes often contain several family members co-localized within the same general area of the genome. FIG. 1 presents a schematic of the arrangement of the major genes in the HLA class I and class I loci found on chromosome 6.

ZFNs directed against the HLA A locus

Figure 2:
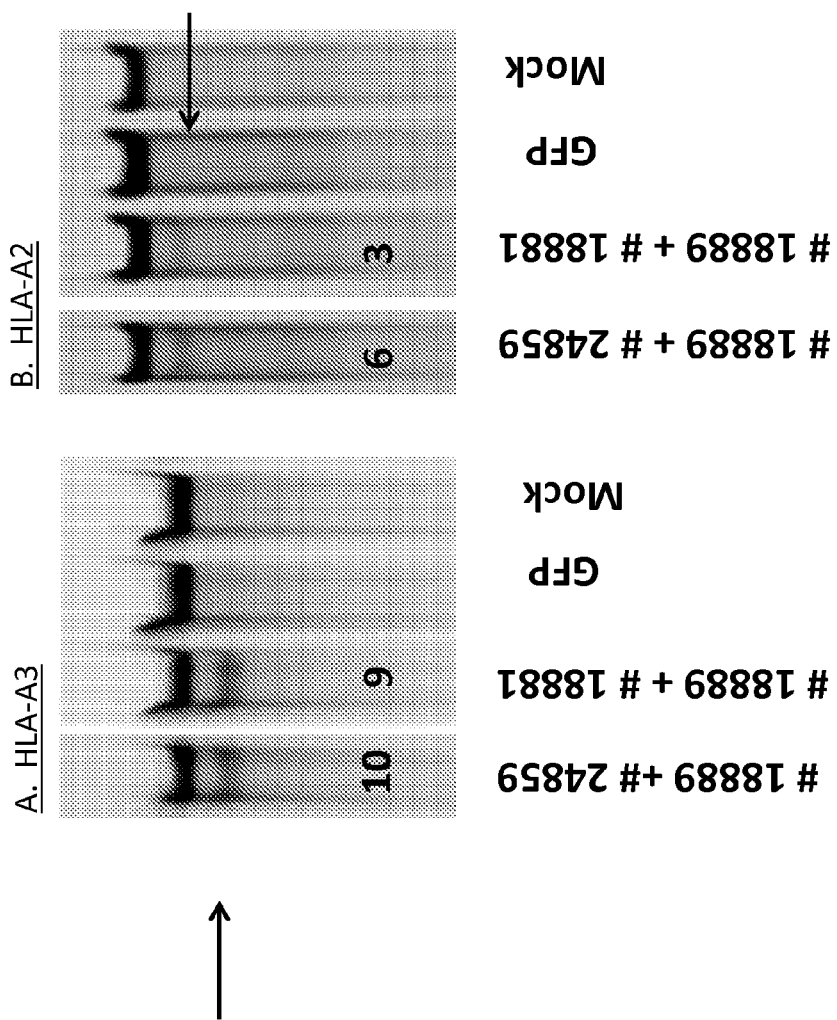
FIG. 2, panels A and B, depicts gels displaying the results of Cel-I mismatch assays (Surveyor™, Transgenomics) for ZFNs targeting HLA A3 (FIG. 2A) and HLA A2 (FIG. 2B). The assay analyzes the percent mismatch with an amplified genomic DNA fragment, and thus allows quantitation of the amount of alterations (%) in the DNA sequence that occurred after NHEJ repair of the ZFN generated DSB. Both gels display the results for a mock transfection, transfection with a GFP encoding plasmid, and transfection with plasmids encoding the ZFN pairs indicated beneath the lanes of each gel into HEK293 cells. The percent gene modification is indicated at the bottom of the lanes.

ZFN pairs were made to target the HLA A locus, with some made specifically against the A2 allele while others were made to target the A3 locus or both. For the A2 and A3 alleles, two pairs were tested such that ZFN 18889 was paired with 18881, and 18889 was also paired with 24859. When the successful pairing of the ZFNs creates a DSB at the desired location, the site is often repaired using non-homologous end joining (NHEJ). This process frequently results in the insertion or deletion of a small number of nucleotides at the site of the mended junction, and so when the DNA around the junction is amplified by PCR, and then subjected to a Cel-I mismatch assay as described, for example, in U.S. Patent Publication Nos. 20080015164; 20080131962 and 20080159996, (Surveyor™, Transgenomic), using the products amplified with respective primers, the frequency of these insertions or deletions (collectively "indels") can be calculated when the products of the assay are subjected to gel electrophoresis. Thus, the A2/A3 specific pairs were examined for activity against their targets using the Cel-I assay. Cells as indicated were transfected with GFP control or each of the pairs of ZFNs. DNA was prepared from the cells one day post transfection, and the results are shown in FIG. 2. Arrows indicate cleavage was found only in samples containing ZFN pairs, but was not found in the control samples wherein cells were transfected with ZFNs specific for GFP. The percent gene modification is shown at the bottom of each lane.

The 18889/18881 pair gave approximately 3% gene modification while the 18889/24859 pair gave approximately 6% NHEJ against the HLA A2 gene when plasmids encoding the ZFNs were transfected into HEK293 cells. For the A3 allele, the 18889/18881 pair gave 9% and the 18889/24859 pair gave 10% NHEJ activity. Since these pairs are capable of cutting both the A2 and A3 alleles, it is possible to create a A2/A3 double knock-out cell line.

The presence of the HLA A marker on the cell surface was analyzed by standard FACS analysis. Briefly, A2, A3 or A2,A3 disrupted HEK293 cells were stained. HLA-A2 staining was done by anti-HLA-A2 PE (BD BioSciences, clone BB7.2). Mouse IgG2bk PE (BD BioSciences) was used for isotype control. For HLA-A3 we first stained these cells with biotinylated anti-HLA-A3 Ab (Abcam, clone 4i53) and then SA-PE (BD). The negative controls in each experiment were: HLA-A2-igG2bK PE, HLA-A3-SA-PE staining without HLA-A3 Ab.

In these experiments, a positive control was performed using the isotype control antibody described above where the results are seen in the figures as a black line that is constant in all samples. The cultures were then either stimulated for HLA expression by addition of IFN gamma (600 IU/mL)+TNF (10 mg/mL) for 48 hours, or used without stimulation.

Figure 3:
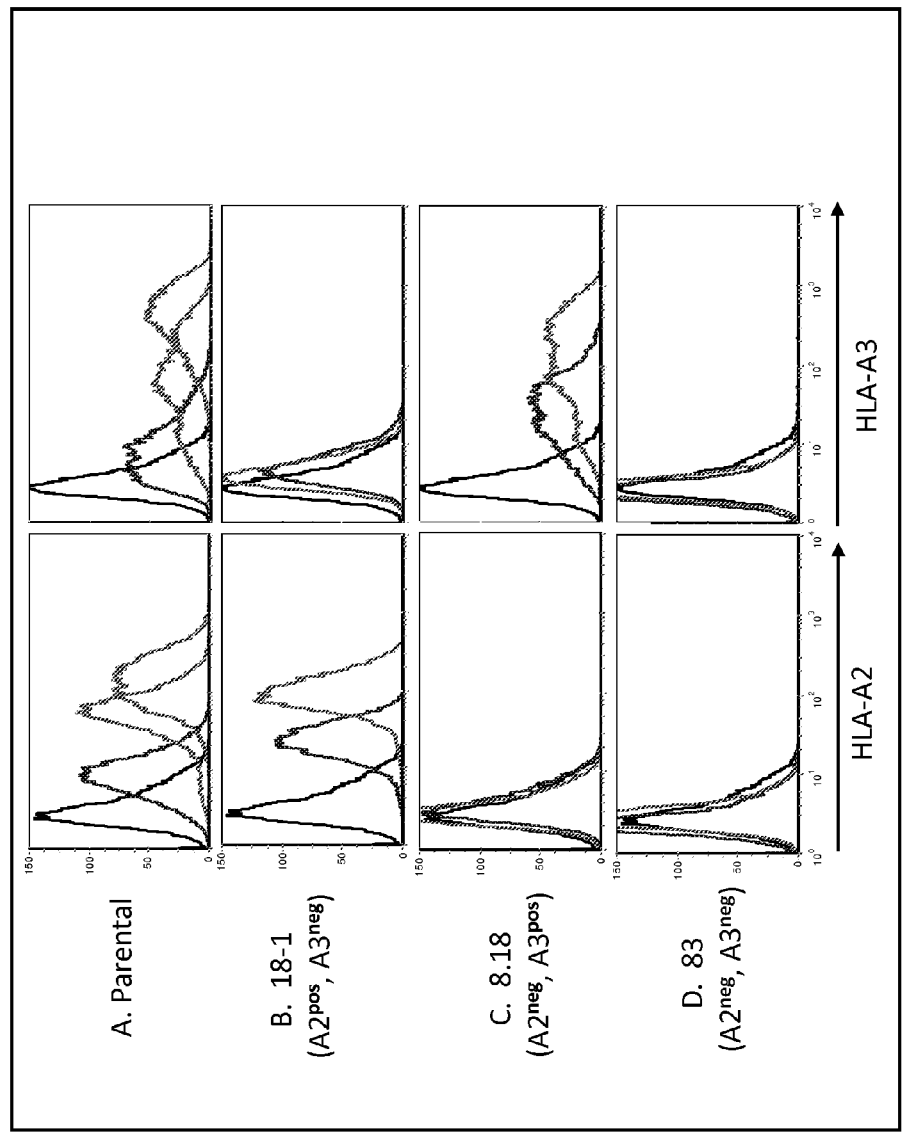
FIG. 3, panels A to D, depict the results of a FACS analysis of HEK293 cells in which either HLA A2, HLA A3 or both HLA A2 and A3 have been disrupted following specific ZFN treatment.

As shown in FIG. 3, the lines closest to the isotype control peak are the samples lacking stimulation, while the shifted peaks are those in the presence of the IFNγ and TNF (see Figure legend). The set of figures on the left hand column are all probed with the anti-HLA A2 antibody, while those on the right hand column were probed with the anti-HLA A3 antibody. As shown, the HLA markers as indicated are no longer detectable when the corresponding HLA genes have been functionally disrupted.

Next, the HLA A knock out HEK293 cell lines were analyzed to see if they could be lysed by HLA-A restricted CTL cell lines. The methodology for these experiments was as follows. Target cells were labeled with 0.1 mCi of $^{51}$Cr for 2 hours. After washing with ice-cold RPMI1640 supplemented with 10% FBS thrice, labeled cells were diluted and distributed at $1 \times 10^3$ target cells/100 µl per well in 96-well, v-bottomed plates. After 30 minutes incubation at room temperature with 10-fold serial dilutions of the peptides, CTL were added at indicated effector target ratio. After 4 hr incubation at 37° C., 5% CO2 incubator, 50 µl of supernatants were collected and count on TopCount (Perkin Elmer). All assays were performed in triplicate. Parental HEK293 cell lines and HLA knocked down HEK293 clones were treated with 600 IU/mL of interferon-γ (IFN-γ; R&D systems®) and 10 ng/mL of tissue necrosis factor-α (TNF-α; R&D systems®) for 48 hours before assay. The percent specific lysis was calculated as follows: ((experimental cpm−spontaneous cpm)/(maximum cpm−spontaneous cpm))×100. In these examples, the peptide antigen target was added in for display by any functioning HLA class I complexes, and in the presence of a functioning HLA A-peptide complex, the CTL clones are able to attack the cells and cause lysis.

Figure 4:
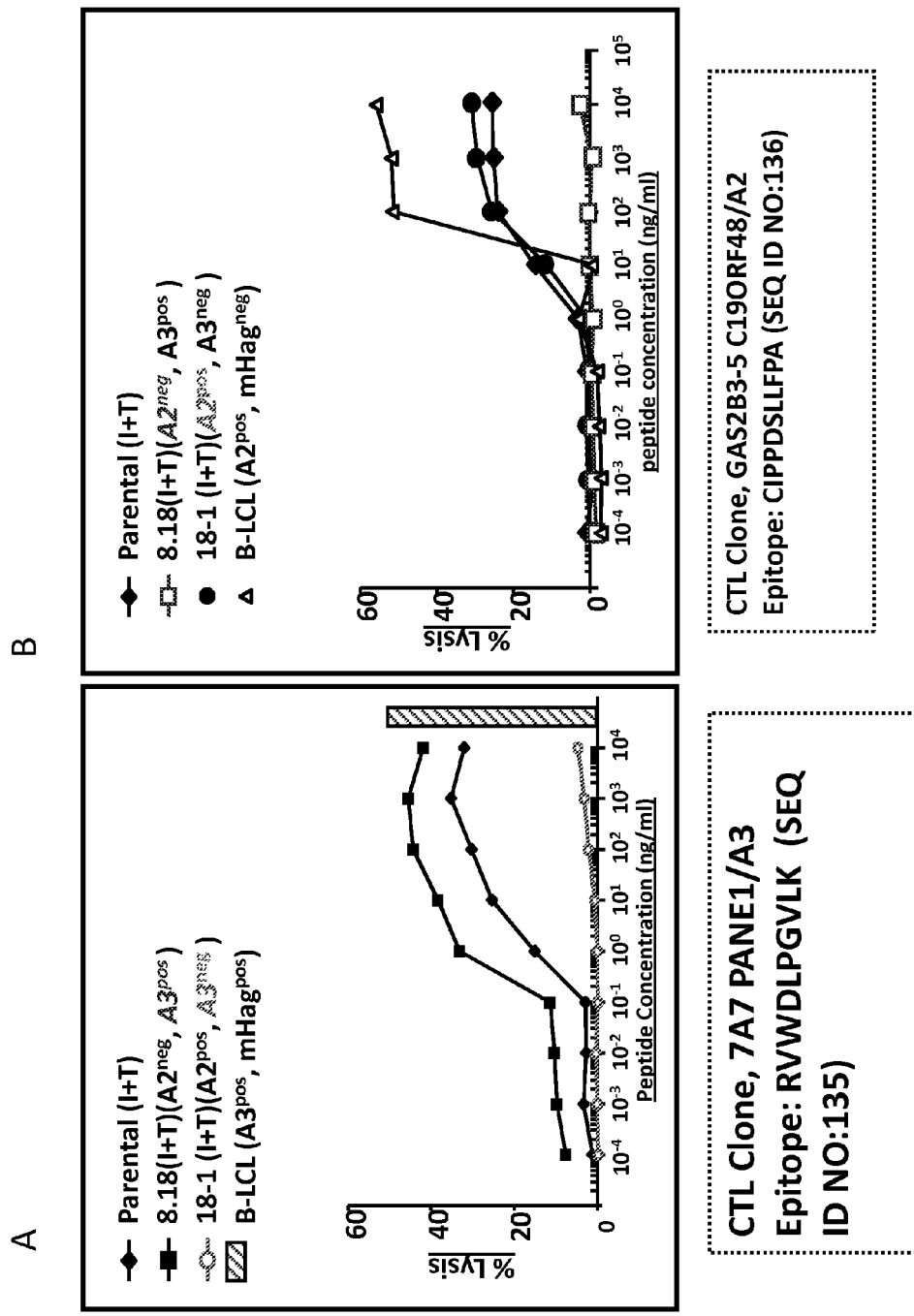
FIG. 4, panels A and B, are graphs depicting the analysis of cell lysis of the HLA-A knock-out HEK293 clones, 18-1, 8.18 and B cell clones (described above for FIG. 3) by specific CTLs targeting HLA A2 or HLA A3, respectively. In this experiment, CTLs restricted to either HLA A2 or HLA A3 were used in combination with the specific peptide epitope (SEQ ID NO:135 and SEQ ID NO:136) that, when displayed on the HLA complex, stimulates CTL action.

As shown in FIG. 4, the HEK293 clones lacking the A2 or the A3 HLA makers were resistant to lysis induced by either the 7A7 PANE1/A3 CTL clone (panel A) or the GAS2B3-5 C19ORF48/A2 CTL clone (panel B) in the presence of their cognate peptide antigens.

ZFN mediated HLA k.o. was repeated in primary T cells. mRNAs encoding the 18889 (containing the KKR FokI variation) and 24859 (containing the ELD FokI variation) ZFNs were nucleofected into primary T cells of a homozygous HLA A2 genotype as follows. $5 \times 10^6$ primary T cells (isolated by standard methods) were nucleofected using an Amaxa Nucleofector® system (program T20) with the ZFN encoding mRNAs using 2.5-10 µg each mRNA per reaction in 100 µL of buffer as supplied by the manufacturer (Lonza). These cells were then analyzed by FACs analysis to determine if the HLA A2 markers were present on the cell surface by standard methodology.

Figure 5:
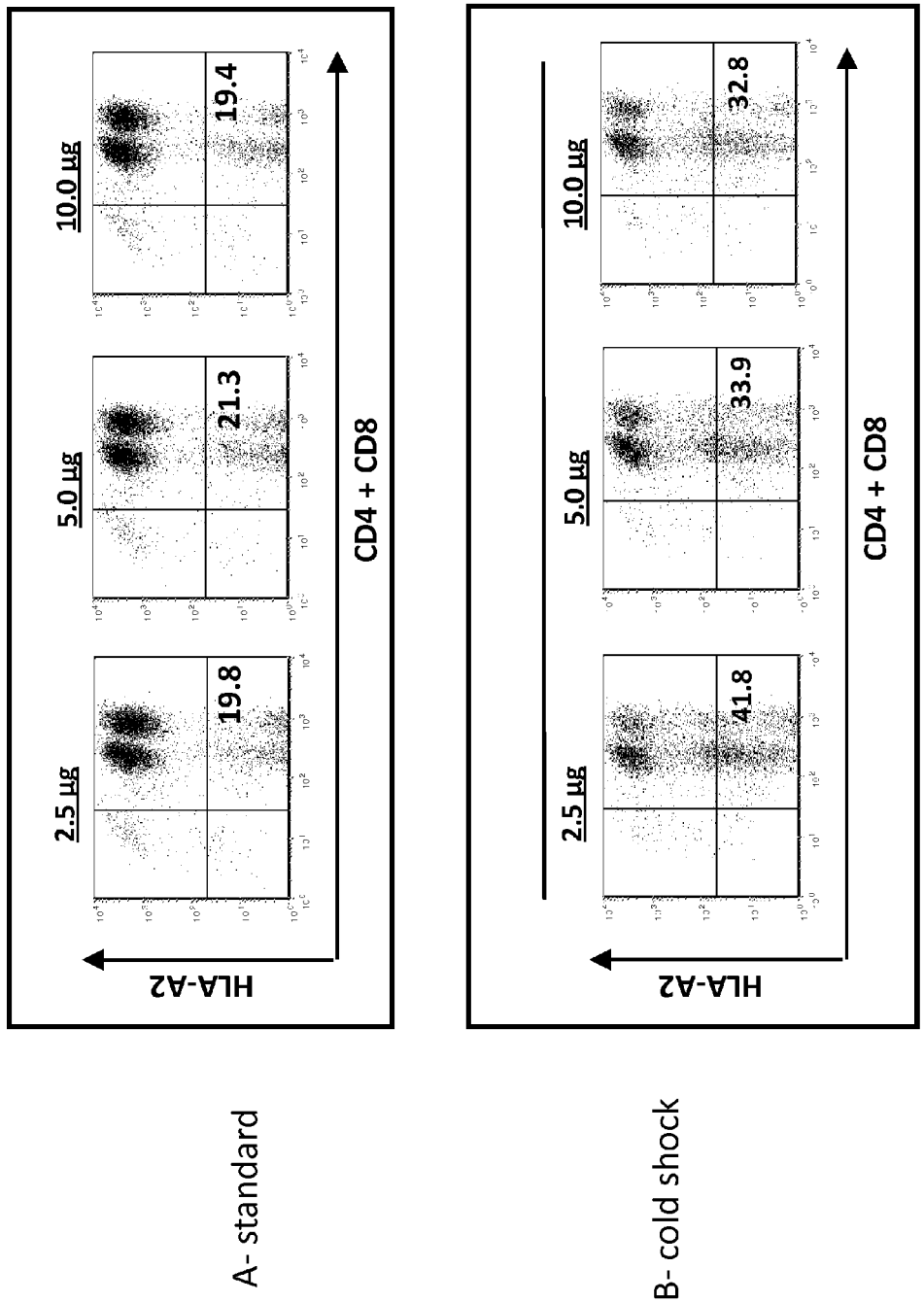
FIG. 5, panels A and B, depict the results of a FACS analysis of HLA A2 staining. In this experiment, primary T-cells were nucleofected with varying amounts of mRNAs (2.5 µg shown in left panels, 5.0 µg shown in middle panels and 10 µg shown in right panels) encoding the HLA A2 specific ZFNs.

As shown in FIG. 5, the percent of cells lacking HLA-A expression ranged from approximately 19-42% following this treatment. FIG. 5A shows the percent of cells lacking HLA-A2 under standard treatment conditions, while FIG. 5B shows the percent of cells lacking HLA-A2 using the "transient cold shock" treatment conditions (see co-owned U.S. Patent Publication No. 2011012989).

Figure 6:
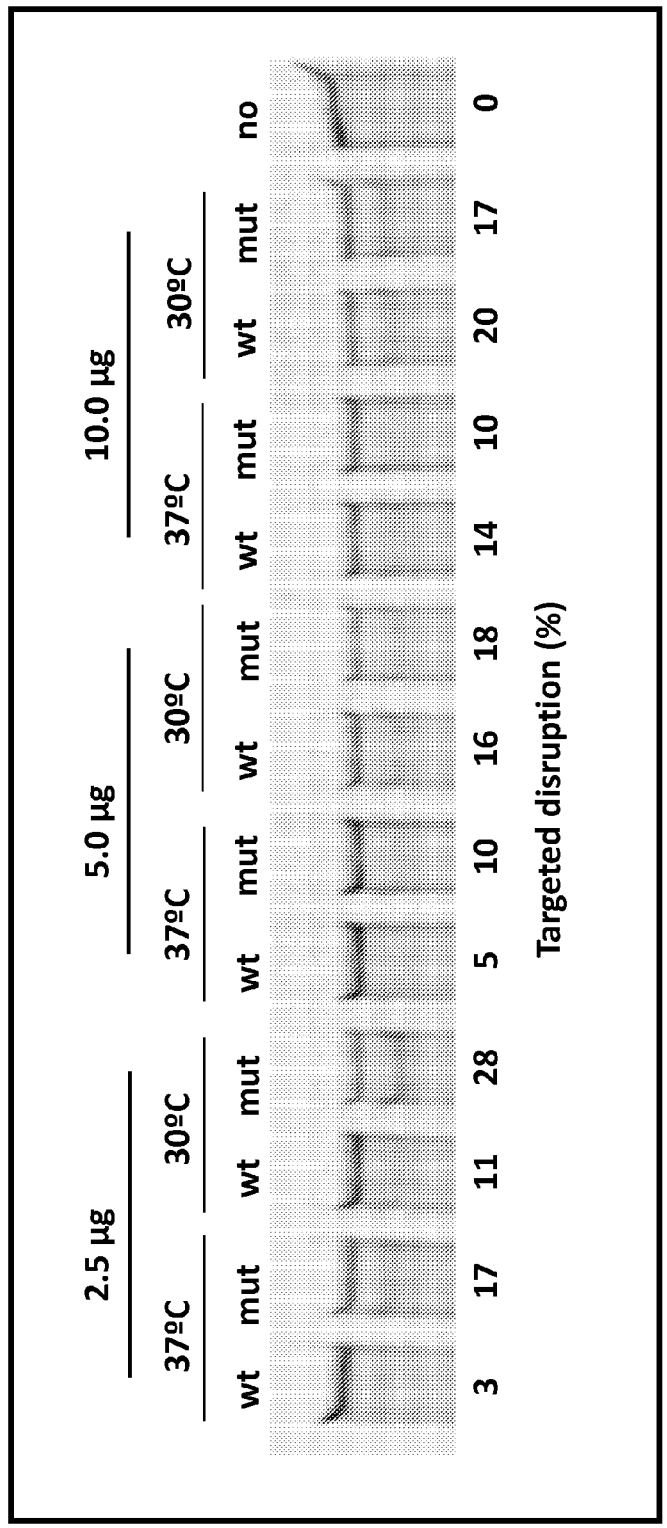
FIG. 6 depicts a gel displaying the results of a Cel-I mismatch analysis for the primary T cells analyzed in FIG. 5. The lanes depict the results using ZFN pairs with wild type Fok I catalytic domain ("wt") and ZFN pairs with an "ELD/KKR" heterodimeric domains ("mut") at the indicated ZFN concentrations (2.5 µg shown in left panels, 5.0 µg shown in middle panels and 10 µg shown in right panels). The percent gene modification detected by this assay ("Targeted disruption (%)") is shown in the bottom of each lane and the results are consistent with the FACS analysis.

In addition, we verified that the loss of HLA A2 expression was caused by ZFN mediated modification of the HLA A2 gene by Cel I analysis as described previously. FIG. 6 shows the Cel I data where the determined percent NHEJ activity at the ZFN target site ranged from 3-28%. In this figure, "wt" refers to a wild type FokI domain, while "mut" refers to the EL/KK FokI mutant pair described above. These data demonstrate that the methods and compositions of the invention can be used to delete HLA A expression and create HLA A null cell lines and primary T cells.

HLA A knock out cells can be enriched to increase the percent HLA A null cells present. A ZFN treated population of T cells, where some low percent of the cells were HLA A null were treated with anti-HLA A2 antibodies tagged with phycoerythrin (PE) (BD BioSciences clone 7.2). Next, beads tagged with an anti-PE antibodies (Miltenyi) were used to bind and thus separate the cells expressing HLA A2 from the HLA A2 null cells according to the manufacturer's directions. Using this technique, the cell populations went from a range of 5.1-34% HLA Asnull cells as assayed by FACs analysis to a range of 92-95% HLA A2 null.

ZFNs directed to the HLA B and C loci

ZFNs were constructed to target the HLA B and C loci and tested using the Cel I assay as described above.

As shown in FIG. 7, these ZFN were successfully able to induce gene modification within both of these genes (HLA C knock out is shown in panel A using ZFNs 25588/25589 while the HLA B knock out in panel B was made using the ZFN pair 25316/25317). These targets are located within the gene sequences, so can be used to create HLA B and HLA C knock out clones.

Large deletions of MHC Class I Complex

ZFNs were also designed to allow for a large deletion with the HLA class I locus which simultaneously deletes the HLA B and HLA C genes. These sets of ZFNs were designed to cut upstream of the HLA B gene (HLA B-up) and downstream of the HLA C gene (HLA C-down). These ZFN pairs were tested individually using the Cel I assay as described above to see the degree of cutting as assayed by NHEJ activity.

FIG. 8A shows the HLA C-down results for pair 15296/15298 for both wt FokI domains (wt) and the EL/KK Fok I domain (mut). FIG. 8B shows a similar set of data for the HLA B-up pairs 15267/15265 and 17454/17456 in K562 cells. Percent gene modification is indicated at the bottom of the lanes ("% NHEJ"). These ZFNs were then used to test if the HLA B and HLA C genes could be deleted by a combination of these two sets of ZFNs. FIG. 9 shows a diagram of the assay used (panel A), and also shows the results of the PCR (panel B). K562 cells were transfected with the two sets of ZFNs and DNA isolated from the cells 3 or 10 days after transfection as indicated.

PCR was performed using primers flanking the region between the HLA-B and HLA-C as illustrated in FIG. 9A. Because of the large amount of DNA to be deleted by a successful double deletion (approximately 100 Kb), the PCR reaction is only successful when the deletion has been made. FIG. 9B shows a gel with a PCR reaction following treatment with the two ZFN pairs. The left side of the gel shows a dilution series of a plasmid used for rough quantitation of the amount of deletion PCR product present on the right side of the gel. In this figure, "wt" refers to a wild type FokI domain, while "mut" refers to the EL/KK FokI mutant pair. The results show that approximately 5% of the DNA present contained the deletion.

Clones derived from this experiment were subjected to FACs analysis to observe the expression of the class I complex overall, and specifically the HLA B and C genes in particular. This was done as described above using an anti-class I antibody to analyze class I expression, and an anti-HLA BC antibody to analyze HLA BC. The results showed that in the parental K562 cell line, 9.02% of the cells expressed the class I complex in general, and 15.98% of the cells expressed HLA B and C. In one knock out line, the class I expression level was 3.88% and HLA BC expression was 7.82%. It is likely that this line does not contain a knock out

Example 3

ZFNs Specific for HLA Class I Regulator Genes

In addition to examining the action of ZFNs specific for class I HLA genes, we also looked at the effects of ZFNs directed to potential class I regulators, namely TAP1, TAP2 and tapasin. ZFNs were made against these gene targets, and their design details are shown in Tables 1 and 2.

Figure 10:
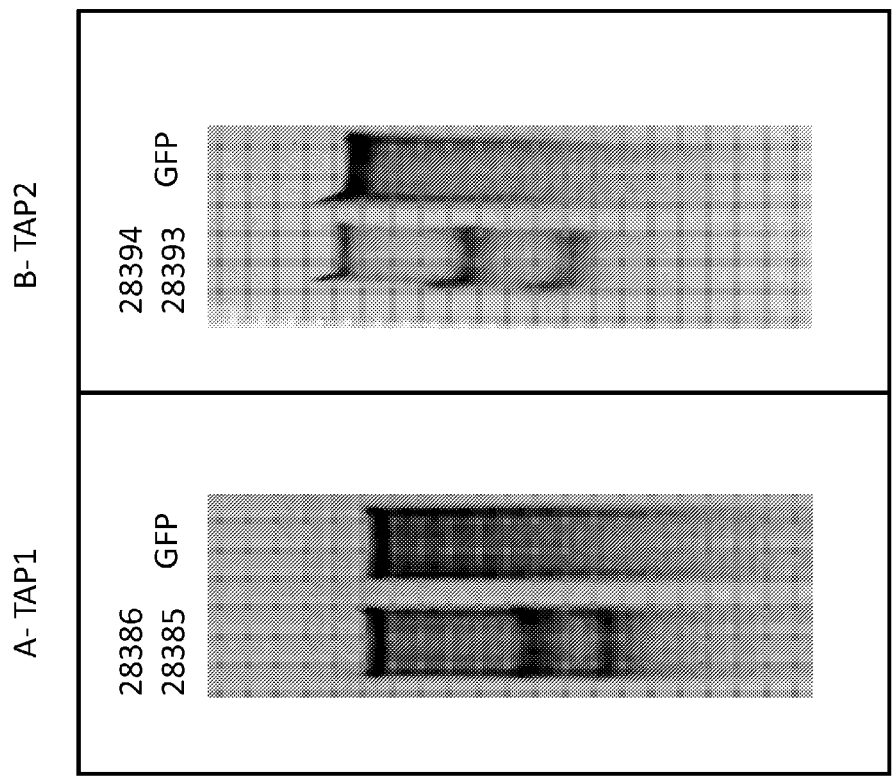
FIG. 10, panels A and B, depict gels displaying the results of cleavage using ZFNs targeting HLA regulatory genes in HEK293 cells.
Figure 11:
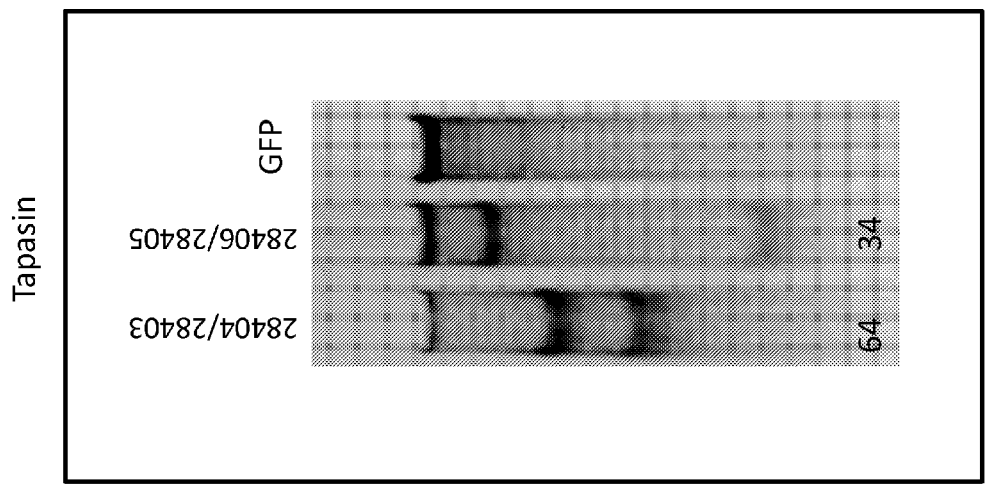
FIG. 11 depicts a gel displaying the results of a Cel-I mismatch assay using ZFNs (ZFN numbers are indicated above lanes 1 and 2) targeting the Tapasin gene in HEK293 cells. The percent gene modification is indicated at the bottom of each lane. These data reveal that this ZFN pair is active against this target.

The ZFNs were transfected into HEK293 cells and tested for gene modification activity by the Cel-I assay as described above As shown in FIGS. 10 and 11, ZFN pairs modified their targets. FIG. 10 A shows the results of the ZFNs specific for TAP1 (pair 28386/28385) where the data indicates an approximate 39% gene modification activity. FIG. 10B shows that the ZFN pair 28394/28393 modifies Tap2 with about 49% efficiency. FIG. 11 shows similar results for ZFNs specific for the Tapasin gene (pair 28406/28405 and pair 28404/28403), where the data indicates an approximate 34 and 64% gene modification activity, respectively.

Example 4

ZFNs Specific for HLA Class II Genes

Figure 12:
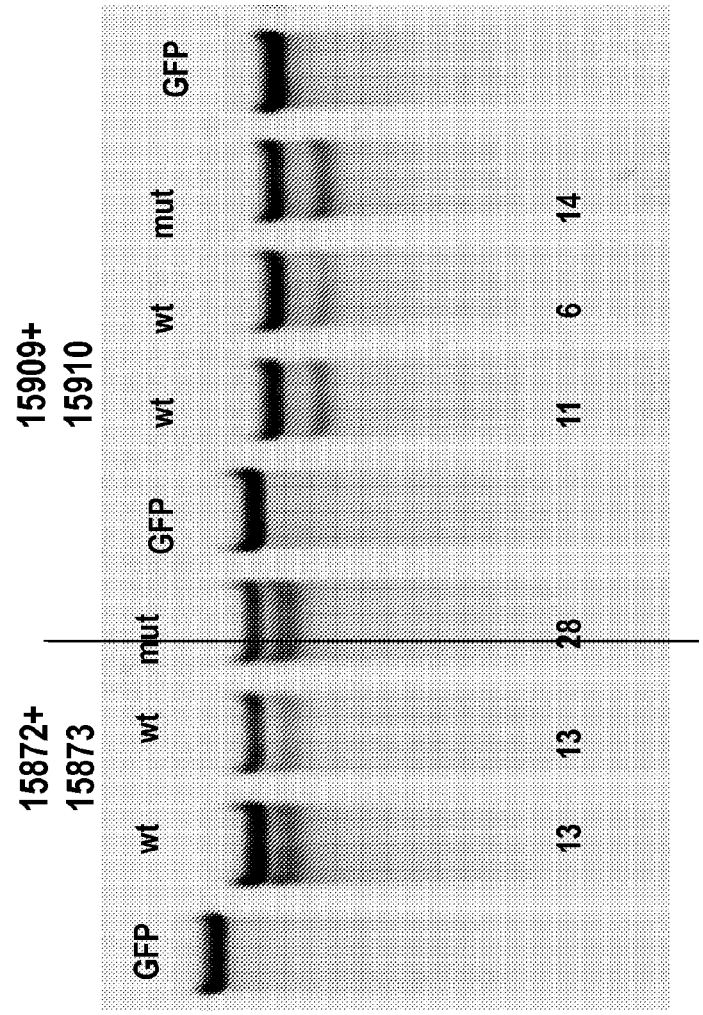
FIG. 12 depicts a gel displaying the results of a Cel-I mismatch assay using ZFNs targeting either a target location upstream of the DBP2 gene (DBP2up) or downstream of the DRA gene (DRAdown) in K562 cells. The transfections used the indicated ZFNs that contained either wild type FokI catalytic domains ("wt") or the EL/KK heterodimeric FokI catalytic domain ("mut"). The percent gene modification as measured by this assay is indicated at the bottom of each lane. The "wt" lanes show duplicate transfections performed on two different transfection dates.

As described above in Example 2 for the class I genes, large deletions were also made in the class II gene cluster. Two ZFN pairs were identified that cleave the target DNA upstream of the DBP2 gene (15872 and 15873) and downstream of the DRA gene (15909 and 15910), respectively. Each pair was analyzed by Cel I analysis in K562 cells as described above. The Cel I analysis displayed in FIG. 12 shows that for the 15872/15873 pair, 13% NHEJ was found using the ZFN versions containing the wild type (wt) FokI domains, while when the pair was made with the EL/KK FokI pair (mut) as described previously, the NHEJ activity was found to be approximately 28%. For the 15909/15910 pair, 6 and 11% NHEJ activity was found using the ZFN versions containing the wild type (wt) FokI domains, while 14% NHEJ activity was observed with the EL/KK FokI domain pair (mut).

Figure 13:
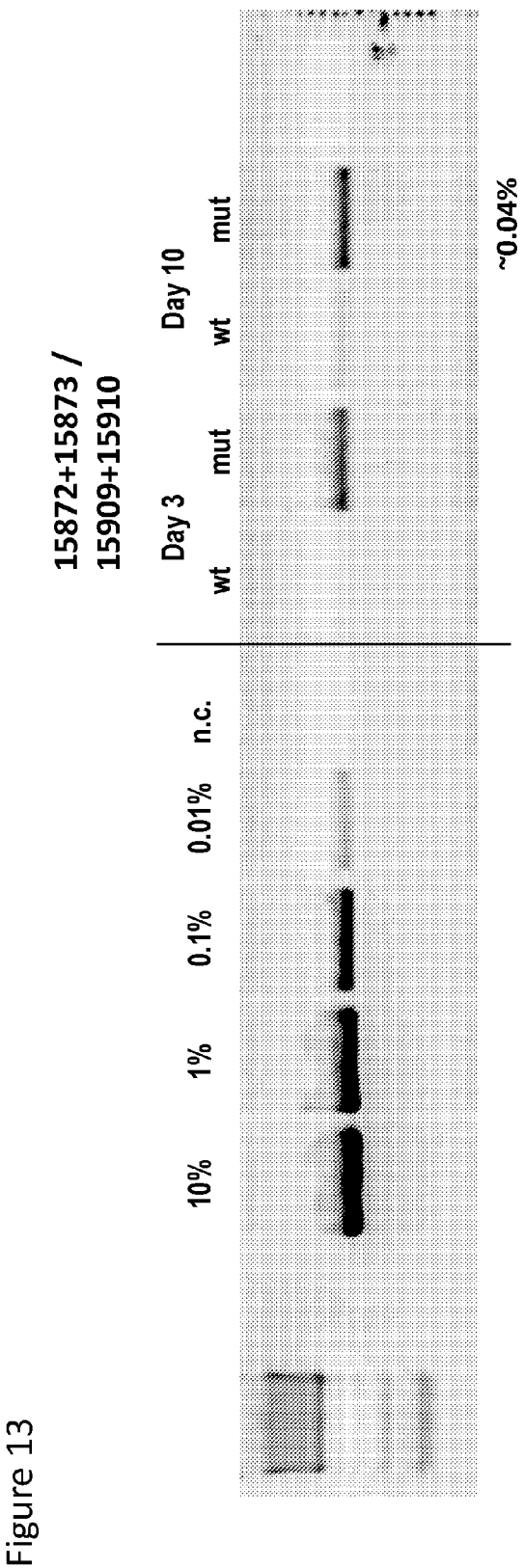
FIG. 13 depicts a gel displaying the results of a deletion PCR similar to that performed in FIG. 9. As described for FIG. 9, the lanes on the left side of the gel contain a dilution series of subcloned PCR product for use in quantitation of the frequency of alleles containing the deletion. The deletion PCR was performed on DNA isolated from cells at day 3 or day 10 after the transfection, and the ZFNs used contained either wild type Fok I catalytic domains ("wt") or the EL/KK heterodimer FokI catalytic domains ("mut"). The results indicate that approximately 0.04% of the alleles contained the large deletion.

The two ZFN pairs were used together to delete the section of DNA between DBP2 and DRA and then a PCR with primers flanking the deletion was performed as described above in Example 2. The PCR products were analyzed and compared with a dilution series to estimate the percent of deletion present. As shown in FIG. 13, approximately 0.04% of the alleles present showed evidence of the deletion.

Figure 14:
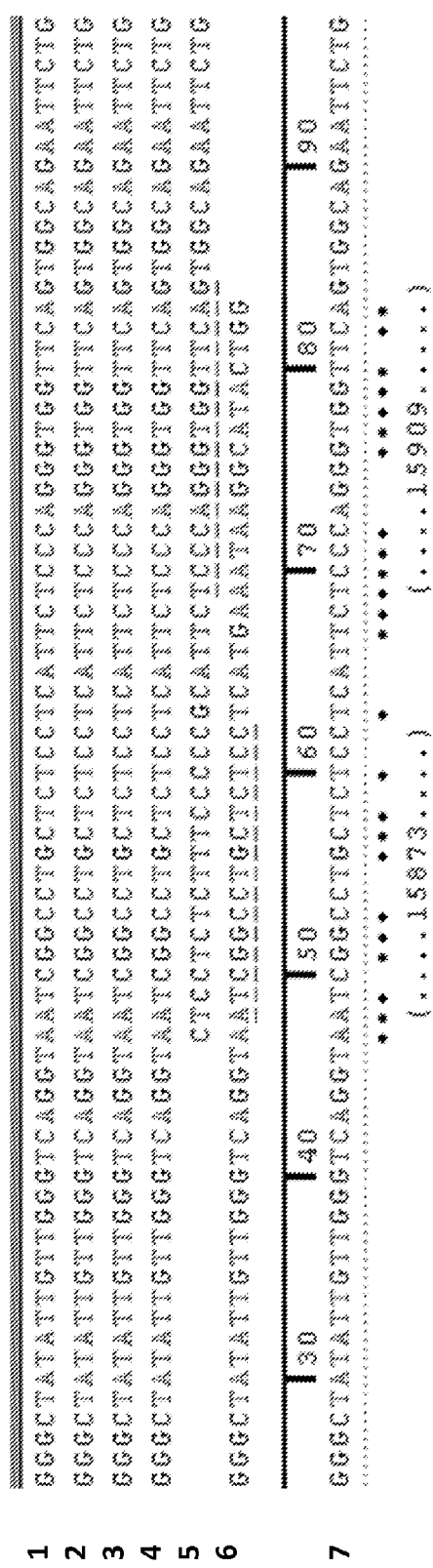
FIG. 14 depicts sequencing results obtained by sequencing the deletion PCR product shown in FIG. 13. Lines 1-4 (SEQ ID NO:137) are individual nucleic acids from the PCR, while line 5 (SEQ ID NO:138) displays the genomic sequence surrounding the 15909 ZFN target site and sequence downstream thereof. Line 6 (SEQ ID NO:139) depicts the genomic sequence surrounding the 15873 target site and sequence upstream thereof. Line 7 (SEQ ID NO:137)shows the consensus sequence from lines 1-4. These results indicate that following cleavage with the DBP2 up and DRA down ZFNs, a large deletion has been generated by rejoining of the ends such that the resultant DNAs contain the distal target site of each ZFN pair.

The junction across the joined sections was sequenced and results are shown in FIG. 14. Line 6 shows the genomic reference sequence at the target site of ZFN 15873 upstream of DBP2 (with the ZFN binding site itself underlined). Line 5 shows the genomic reference sequence around the binding site of ZFN 15909 downstream of DRA (with the ZFN binding site itself underlined). Lines 1-4 show the sequence of 4 separate subclones of the PCR product as described above and demonstrate that both target sequences are present indicating that the two ends have joined at the ZFN cleavage sites following the deletion. Line 7 shows the consensus of the deletion products.

These results indicate that large deletions (approximately 700 Kb) can be made to delete portions of the HLA class II complex.

Example 5

ZFNs Specific for HLA Class II Regulator Genes

As described previously, the class II complex appears to be regulated by a master regulatory molecule CIITA. Thus, if the CIITA gene were disrupted or manipulated, it might be possible to disrupt or alter HLA class II expression as a whole. Thus, ZFN pairs were made to target the CIITA gene. Additionally, the RFX5 gene product appears to be part of the class II enhanceo some, and so disruption of this gene may also disrupt or alter HLA class II expression. Accordingly, ZFN pairs targeting this gene were made and tested as well. Both sets of ZFNs were tested using the Cel I assay as described above in K562 cells.

Figure 15:
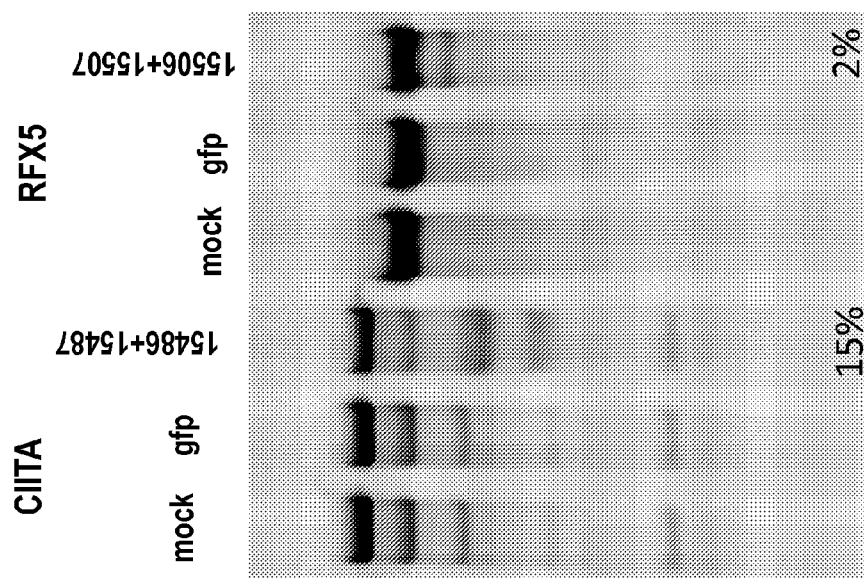
FIG. 15 depicts a gel displaying the results following a Cel-I mismatch assay as described above. ZFNs targeting either the HLA class II regulator genes CIITA or RFX5 were used in K562 cells, and the percent gene modification is indicated at the bottom of the lanes. Control lanes contain the results of experiments done either with no added ZFNs ("mock") or transfected with a GFP encoding plasmid ("gfp") are also shown.

As shown in FIG. 15, Cel I mismatch assay results show that the CIITA targeted ZFN pair (15486/15487) was able to cause gene modification in approximately 15% of the alleles, while the RFX5 targeted ZFN pair (15506/15507) caused gene modification in about 2% of the alleles. Control reactions include a mock transfection with no added DNA and a transfection using a GFP expression plasmid.

Next, the CIITA targeted ZFN pairs were tested by transfecting into RAJI cells. These cells are a lymphoblastoid cell line that is known to express HLA class II.

Figure 16:
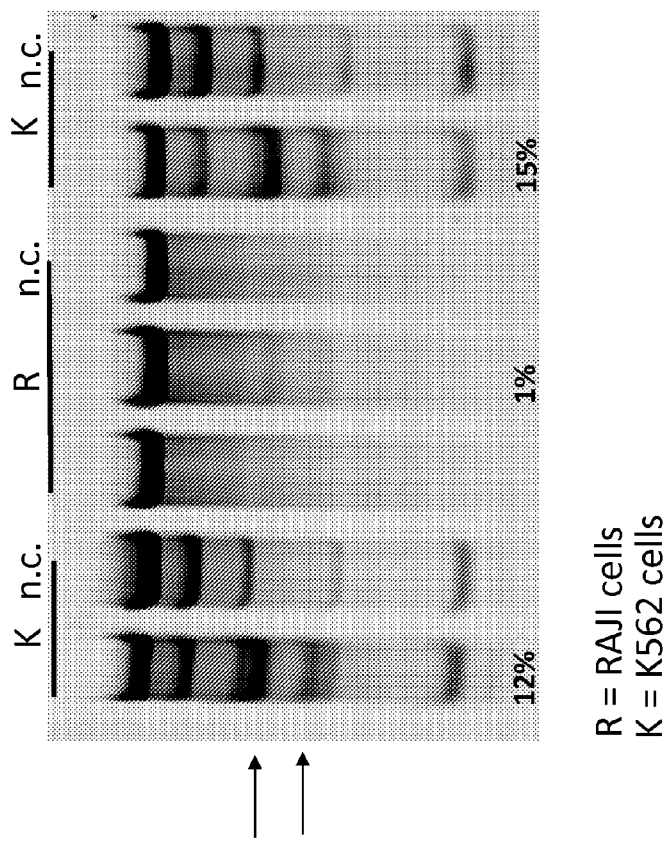
FIG. 16 depicts a gel displaying the results following a Cel-I mismatch assay as described above. The CIITA targeting ZFNs were used in either K562 cells ("K") or RAJI cells ("R"). The percent gene modification as detected by this assay is shown at the bottom of the lanes, and the arrows show the bands indicative of modification activity. These results demonstrate that the CIITA targeting ZFNs can work in RAJI cells as well as K562 cells. "n.c." indicates the negative control done without any ZFN encoding DNA during the transfection.

The gel depicted in FIG. 16 shows a comparison of the Cel I activity in K562 cells alongside RAJI cells. 'K' depicts the results in K562 cells and 'R' depicts the results in RAJI cells. 'n.c.' depicts the negative control in cells without any added ZFN DNA during transfection. The results demonstrate that in K562 cells, there was approximately 12-15% gene modification activity observed and in RAJI cells, approximately 1% probably reflecting the poorer transfection efficiency in RAJI cells.

Example 6

Use of HLA Knock Out Cells in Combination with Another Genetic Modification

The CD19 marker is a cell surface marker that is expressed on 95% of all B-cell malignancies. It is not expressed on hematopoietic stem cells, or on normal tissues outside the B lineage; and is lost upon differentiation of B cells to mature plasma cells. Thus, CD19 represents an attractive target for targeted immunotherapy for treatment of B cell lymphomas and B-ALL cells. T-cells containing a chimeric antigen receptor (CAR) specific for CD19 have been created (see Davies et al (2010) *Cancer Res* 70(10):3915-24) through transposon aided genomic insertion. Deletion of the HLA markers could allow such a cell therapy product to be used for a number of patients rather than just those with the matching HLA haplotype. Thus, the CAR-19 modified T cells were treated with the HLA A specific ZFNs as described above in Example 2. The cells were then analyzed by FACS analysis as described above.

Figure 17:
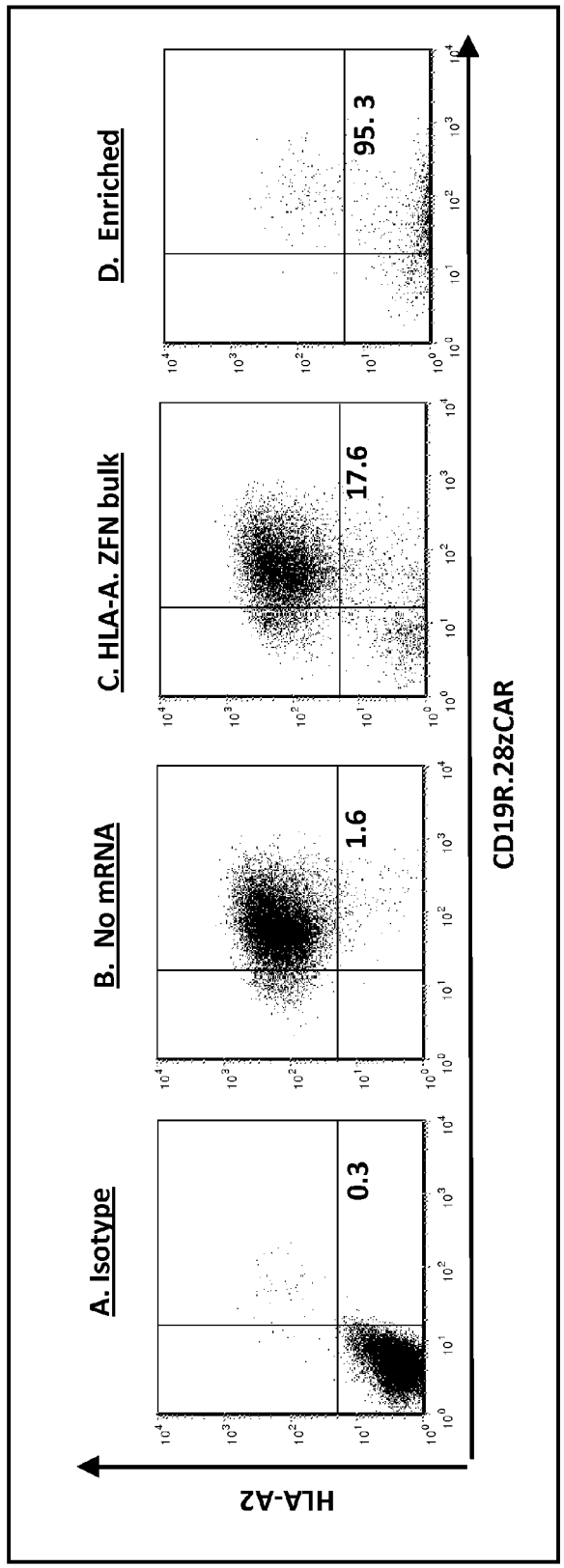
FIG. 17, panels A to D, depict the results of a FACS analysis done on T cells that had been previously been made transgenic for a chimeric antigen receptor that targets CD19 (CD19CAR). These CD19CAR modified T cells were nucleofected with mRNAs encoding ZFNs that target the HLA A2 gene and HLA-A2 negative cells were enriched by negative bead sorting with an HLA-A2 antibody and a FACS assay was performed using a HLA A2 specific antibody. The results indicate that the HLA A2 knock out cells were be enriched such that the population contained 95.3% HLA A2 knock outs.

As shown in FIG. 17, analyzing the cells using a negative (isotype) control antibody (mouse anti-IgG2 (BD BioSciences)) showed a 0.3% negative (non-specific binding) signal for HLA-A2 (as described above) expression. When mock transfected cells were analyzed with the HLA-A2 antibody (no mRNA), 1.6% of the cells did not expressing HLA-A2. A bulk population of T cells treated with ZFNs showed that 17.6% of the cells were HLA A2 null, but following enrichment for HLA A2 non-expressers as described above in Example 2, 95.3% of the cells were HLA A2 null (compare "Enriched" with "HLA-A.ZFN bulk") in FIG. 17.

Figure 18:
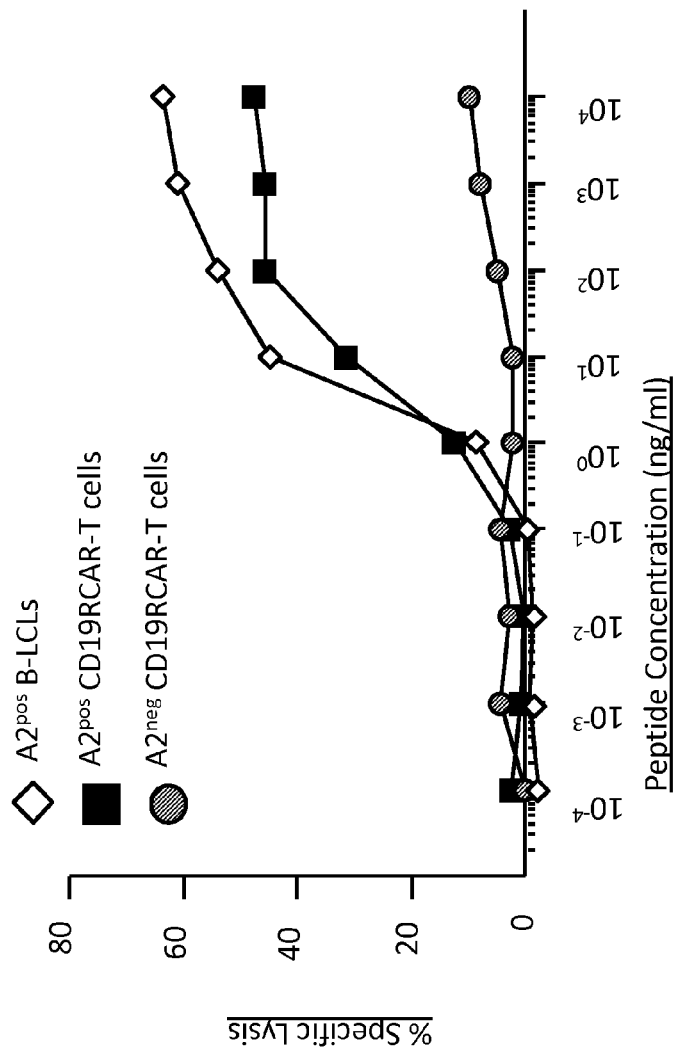
FIG. 18 is a graph depicting the results of a lysis assay with HLA A2-specific CD19CAR containing T cells which had either been treated with the HLA A2-specific ZFNs (A2neg CD19RCAR-T cells) and enriched using the HLA-A2 specific antibody, or had been mock transfected (A2posCD19RCAR-T cells). Cells were incubated with increasing amounts of the specific peptide epitope. As a positive control, A2pos B cells were used. The results indicate that the cells lacking the HLA A2 gene product are resistant to HLA A2-specific CTL induced lysis.

The HLA A2 null T cells were then treated with HLA A2-specific CTLs. As is shown in FIG. 18, the cells that were HLA A2 null were resistant to lysis by the CTLs. These experiments were carried out as described previously. The CTLs used were the GAS2B3-5 C19ORF48/A2 cells (CIPP-DSLLFPA (SEQ ID NO: 136) epitope) described previously (see Example 2) and are specific for HLA A2.

These data demonstrate that ZFP mediated HLA knockouts can be made in cells that carry another useful genetic modification and thus allow a wider use of these therapeutics.

Example 7

TCR Knock Out

Use of the CAR-19 modified T cells as described above in Example 6 could be potentially hampered in an allogenic setting due to endogenous TCRαβ expression. Thus, ZFN reagents designed to disrupt either the TCRα or the TCRβ constant chains were tested in primary T cells. The ZFN pair 25539/25540 was used for the TCRα knockout and the ZFN pair 16783/16787 was used for the TCRβ knockout. In these experiments, 1 million primary T cells were subjected to nucleofection with the Amaxa system using the ZFN encoding mRNAs as described above. Cells were then subjected to both FACs and Cel I analyses.

Figure 19:
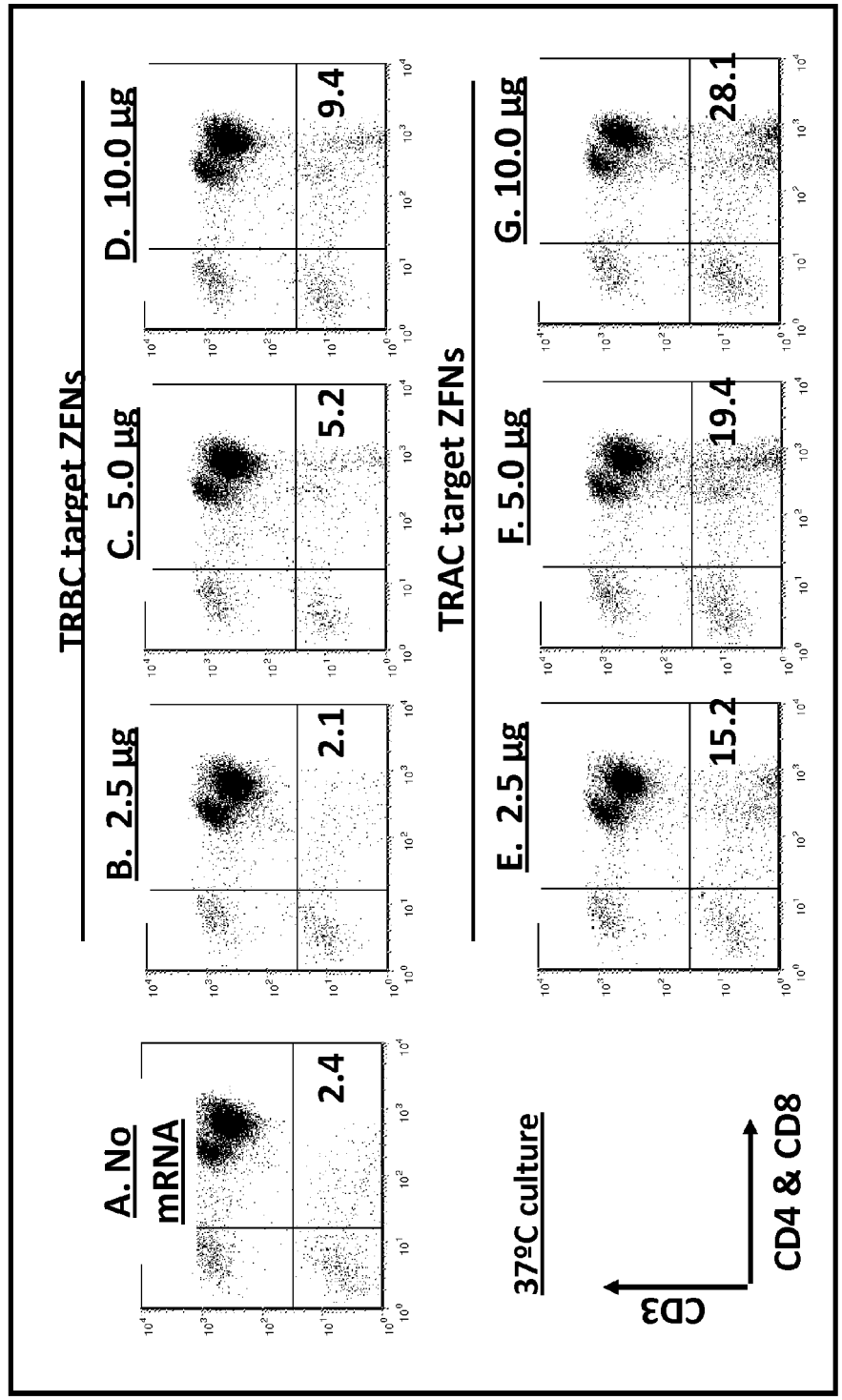
FIG. 19, panels A to G, depict the results from several FACS analyses. mRNAs encoding ZFNs specific for either TCRβ ("TRBC," FIG. 19A to FIG. 19D) or TCRα ("TRAC," FIG. 19E to FIG. 19G) were used in a range from 2.5µg to 10µg as indicated above the FACS. The assay is designed to score CD3 on the cell surface, a complex that is dependent on the presence of the TCR. The results demonstrate that the TCRβ specific ZFNs can cause approximately 9% of the cells in the population to lose the CD3 marker while the TCRa specific ZFNs can cause approximately 28% of cells to lose the CD3 marker.

As shown in FIG. 19, cells lacking CD3 expression increase from 2.4%, without any nucleofected TCR ZFN mRNAs, to 9.4% in the presence of 10 μg TCRβ-specific ZFN mRNA. In the presence of 10 μg TCRα-specific ZNF mRNA, the percent of CD3 negative cells increases to 28.1%. The FACs data is presented with the TRCβ data is shown across the top ("TRBC target ZFNs") and the TCRα data is across the bottom ("TRAC target ZFNs"). Lack of expression of either the TCRα or the TCRβ chains is assayed by the presence of the CD3 complex, in which a functioning TCR is required for stable presentation on the cell surface.

Figure 20:
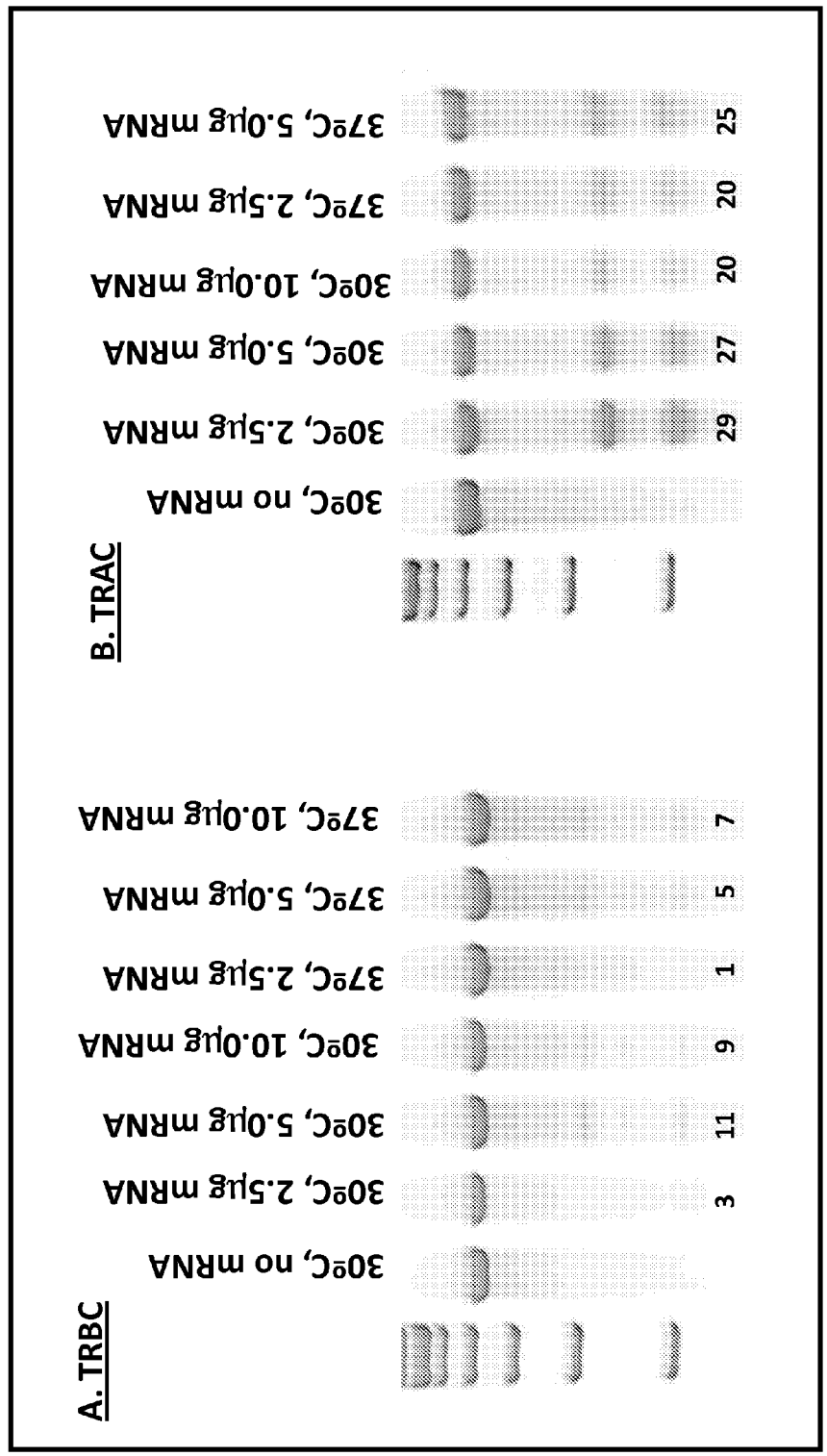
FIG. 20, panels A and B, depict a gel displaying the results of a Cel-I assay as described above to assess the amount of gene modification present when either mRNAs encoding the TCRβ-specific ZFNs (TRBC, FIG. 20A) or encoding the TCRα-specific ZFNs (TRAC, FIG. 20B) are used. In this example, mRNAs were nucleofected and cultured according to either standard conditions or using the "transient cold shock" conditions. The results agree generally with the results from FIG. 19 and indicate that both ZFN sets are capable of cleaving their intended targets.

FIG. 20 depicts a gel with the results of the Cel I analysis, performed as described above on samples incubated under the transient hypothermic or the standard conditions, and the percent gene modification activity data (displayed at the bottom of each lane) agrees roughly with the FACs analysis that was done on cells incubated at 37 degrees.

All patents, patent applications and publications mentioned herein are hereby incorporated by reference in their entirety.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

What is claimed is:

1. A protein comprising an engineered zinc finger DNA-binding domain, wherein the engineered zinc finger DNA-binding domain comprises four, five or six zinc finger DNA recognition regions designated and ordered F1 to F4, F1 to F5 or F1 to F6 from N-terminus to C-terminus and further wherein the engineered zinc finger DNA-binding domain comprises the zinc finger DNA recognition regions selected from the group consisting of:

(i) F1: QSSHLTR (SEQ ID NO:1);
F2: RSDHLTT (SEQ ID NO:2);
F3: RSDTLSQ (SEQ ID NO:3);
F4: RSADLSR (SEQ ID NO:4);
F5: QSSDLSR (SEQ ID NO:5); and
F6: RSDALTQ (SEQ ID NO:6), wherein the protein binds to the target site set forth in SEQ ID NO:97 in an endogenous human leukocyte antigen (HLA) A2 gene;

(ii) F1: QKTHLAK (SEQ ID NO:7);
F2: RSDTLSN (SEQ ID NO:8);
F3: RKDVRIT (SEQ ID NO:9);
F4: RSDHLST (SEQ ID NO:10); and
F5: DSSARKK (SEQ ID NO:11), wherein the protein binds to the target site set forth in SEQ ID NO:98 in an endogenous HLA A2 gene;

(iii) F1: QNAHRKT (SEQ ID NO:12);
F2: RSDSLLR (SEQ ID NO:13);
F3: RNDDRKK (SEQ ID NO:14);
F4: RSDHLST (SEQ ID NO:10); and
F5: DSSARKK (SEQ ID NO:11), wherein the protein binds to the target site set forth in SEQ ID NO:99 in an endogenous HLA A2 gene;

(iv) F1: DRSHLSR (SEQ ID NO:15);
F2: RSDDLTR (SEQ ID NO:16);
F3: DRSDLSR (SEQ ID NO:17); and
F4: QSGHLSR (SEQ ID NO:18), wherein the protein binds to the target site set forth in SEQ ID NO:100 in an endogenous HLA A3 gene;

(v) F1: DRSALSR (SEQ ID NO:19);
F2: QSSDLRR (SEQ ID NO:20);
F3: DRSALSR (SEQ ID NO:19);
F4: DRSHLAR (SEQ ID NO:21);
F5: RSDDLSK (SEQ ID NO:22); and
F6: DRSHLAR (SEQ ID NO:21), wherein the protein binds to the target site set forth in SEQ ID NO:101 in an endogenous HLA A3 gene;

(vi) F1: SSELLNE (SEQ ID NO:23);
F2: TSSHLSR (SEQ ID NO:24);
F3: QSGDRNK (SEQ ID NO:25);
F4: RSANLAR (SEQ ID NO:26); and F5: RSDNLRE (SEQ ID NO:27), wherein the protein binds to the target site set forth in SEQ ID NO:102 in an endogenous HLA B gene;
(vii) F1: QSGDLTR (SEQ ID NO:28);
F2: RSDDLTR (SEQ ID NO:16);
F3: DQSTLRN (SEQ ID NO:29);
F4: DRSNLSR (SEQ ID NO:30); and
F5: DAFTRTR (SEQ ID NO:31), wherein the protein binds to the target site set forth in SEQ ID NO:103 in an endogenous HLA B gene;
(viii) F1: RSDNLSE (SEQ ID NO:32);
F2: ASKTRKN (SEQ ID NO:33);
F3: TSGNLTR (SEQ ID NO:34); and
F4: RSDALAR (SEQ ID NO:35), wherein the protein binds to the target site set forth in SEQ ID NO:104 in an endogenous HLA B gene;
(ix) F1: DRSALSR (SEQ ID NO:19);
F2: QSGNLAR (SEQ ID NO:36);
F3: DRSALSR (SEQ ID NO:19);
F4: QSGHLSR (SEQ ID NO:18), wherein the protein binds to the target site set forth in SEQ ID NO:105 in an endogenous HLA B gene;
(x) F1: RSDNLSE (SEQ ID NO:32);
F2: ASKTRKN (SEQ ID NO:33);
F3: QSGHLSR (SEQ ID NO:18);
F4: TSGHLSR (SEQ ID NO:37); and
F5: QSGHLSR (SEQ ID NO:18), wherein the protein binds to the target site set forth in SEQ ID NO:106 in an endogenous HLA B gene;
(xi) F1: RSADLTR (SEQ ID NO:38);
F2: QSGDLTR (SEQ ID NO:28);
F3: QSGNLAR (SEQ ID NO:36); and
F4: QSGDLTR (SEQ ID NO:28), wherein the protein binds to the target site set forth in SEQ ID NO:107 in an endogenous HLA B gene;
(xii) F1: QSGHLSR (SEQ ID NO:18);
F2: RSDHLST (SEQ ID NO:10);
F3: QSADRTK (SEQ ID NO:39);
F4: TSGSLSR (SEQ ID NO:40); and
F5: QSADRTK (SEQ ID NO:39), wherein the protein binds to the target site set forth in SEQ ID NO:108 in an endogenous HLA C gene;
(xiii) F1: QSGDLTR (SEQ ID NO:28);
F2: RSDHLST (SEQ ID NO:10);
F3: QSADRTK (SEQ ID NO:39);
F4: RSDNLSA (SEQ ID NO:41); and
F5: RSDNRTT (SEQ ID NO:42), wherein the protein binds to the target site set forth in SEQ ID NO:109 in an endogenous HLA C gene;
(xiv) F1: QRSNLVR (SEQ ID NO:43);
F2: DRSALAR (SEQ ID NO:44);
F3: QSSDLRR (SEQ ID NO:20);
F4: RSDDLTR (SEQ ID NO:16); and
F5: RSDDLTR (SEQ ID NO:16), wherein the protein binds to the target site set forth in SEQ ID NO:110 in an endogenous HLA C gene;
(xv) F1: RSDDLTR (SEQ ID NO:16);
F2: DRSDLSR (SEQ ID NO:17);
F3: QSGHLSR (SEQ ID NO:18);
F4: RSDHLSA (SEQ ID NO:45); and
F5: ESRYLMV (SEQ ID NO:46), wherein the protein binds to the target site set forth in SEQ ID NO:111 in an endogenous HLA C gene;
(xvi) F1: RSDHLST (SEQ ID NO:10);
F2: DNANRTK (SEQ ID NO:47);
F3: QSGDLTR (SEQ ID NO:28);
F4: RSDALST (SEQ ID NO:48); and F5: ASSNRKT (SEQ ID NO:49), wherein the protein binds to the target site set forth in SEQ ID NO:112 in an endogenous DBP2 gene;
(xvii) F1: TSGNLTR (SEQ ID NO:34);
F2: DRSDLSR (SEQ ID NO:17);
F3: RSDNLSE (SEQ ID NO:32);
F4: RSANLTR (SEQ ID NO:50); and
F5: QSGHLSR (SEQ ID NO:18), wherein the protein binds to the target site set forth in SEQ ID NO:113 in an endogenous DBP2 gene;
(xviii) F1: RSDNLSE (SEQ ID NO:32);
F2: TSGSLTR (SEQ ID NO:51);
F3: TSGHLSR (SEQ ID NO:37);
F4: RSDNLSQ (SEQ ID NO:52); and
F5: ASNDRKK (SEQ ID NO:53), wherein the protein binds to the target site set forth in SEQ ID NO:114 in an endogenous DRA gene;
(xix) F1: RSDNLSR (SEQ ID NO:54);
F2: DNNARIN (SEQ ID NO:55);
F3: RSDSLSV (SEQ ID NO:56);
F4: QNQHRIN (SEQ ID NO:57); and
F5: RSDHLSR (SEQ ID NO:58), wherein the protein binds to the target site set forth in SEQ ID NO:115 in an endogenous DRA gene;
(xx) F1: DSSDRKK (SEQ ID NO:59);
F2: DRSHLTR (SEQ ID NO:60);
F3: RSDALAR (SEQ ID NO:35);
F4: QSSDLSR (SEQ ID NO:5); and
F5: RSDNLTT (SEQ ID NO:61), wherein the protein binds to the target site set forth in SEQ ID NO:116 in an endogenous transporter associated with antigen processing 1 (TAP1) gene;
(xxi) F1: RSANLAR (SEQ ID NO:26);
F2: QSGHLSR (SEQ ID NO:18);
F3: TSGNLTR (SEQ ID NO:34);
F4: QSGALVI (SEQ ID NO:62);
F5: RSDHLSE (SEQ ID NO:63); and
F6: RKHDRTK (SEQ ID NO:64), wherein the protein binds to the target site set forth in SEQ ID NO:117 in an endogenous TAP1 gene;
(xxii) F1: QSSDLSR (SEQ ID NO:5);
F2: QSGDLTR (SEQ ID NO:28);
F3: QSSHLTR (SEQ ID NO:1):
F4: RSDDRKT (SEQ ID NO:65);
F5: TSGNLTR (SEQ ID NO:34); and
F6: RSDDLTR (SEQ ID NO:16), wherein the protein binds to the target site set forth in SEQ ID NO:118 in an endogenous transporter associated with antigen processing 2(TAP2) gene;
(xxiii) F1: RSDNLST (SEQ ID NO:66);
F2: RSDALAR (SEQ ID NO:35);
F3: RSDVLSA (SEQ ID NO:67);
F4: DRSNRIK (SEQ ID NO:68);
F5: RREDLIT (SEQ ID NO:69); and
F6: TSSNLSR (SEQ ID NO:70), wherein the protein binds to the target site set forth in SEQ ID NO:119 in an endogenous TAP2 gene;
(xxiv) F1: RSDNLSE (SEQ ID NO:32);
F2: KRCNLRC (SEQ ID NO:71);
F3: DRSDLSR (SEQ ID NO:17);
F4: QTTHRNR (SEQ ID NO:72);
F5: DRSDLSR (SEQ ID NO:17), and
F6: QSSTRAR (SEQ ID NO:73), wherein the protein binds to the target site set forth in SEQ ID NO:120 in an endogenous tapasin gene;
(xxv) F1: QSSDLR (SEQ ID NO:5);
F2: RSDNLTR (SEQ ID NO:74);

F3: QSSHLTR (SEQ ID NO:1);
F4: QSSDLTR (SEQ ID NO:75);
F5: RSDNLAR (SEQ ID NO:76); and
F6: QKVNLMS (SEQ ID NO:77), wherein the protein binds to the target site set forth in SEQ ID NO:121 in an endogenous tapasin gene;

(xxvi) F1: TSGNLTR (SEQ ID NO:34);
F2: LSQDLNR (SEQ ID NO:78);
F3: RSDSLSA (SEQ ID NO:79);
F4: DRSHLAR (SEQ ID NO:21);
F5: RSDHLST (SEQ ID NO:10); and
F6: QSGHLSR (SEQ ID NO:18), wherein the protein binds to the target site set forth in SEQ ID NO:122 in an endogenous tapasin gene;

(xxvii) F1: RSDDLTR (SEQ ID NO:16);
F2: SSSNLTK (SEQ ID NO:80);
F3: TSGSLSR (SEQ ID NO:40);
F4: QSGDLTR (SEQ ID NO:28);
F5: RSDHLSE (SEQ ID NO:63); and
F6: RNRDRIT (SEQ ID NO:81), wherein the protein binds to the target site set forth in SEQ ID NO:123 in an endogenous tapasin gene;

(xxviii) F1: RSDDLTR (SEQ ID NO:16);
F2: RSDHLSE (SEQ ID NO:63);
F3: NSRNRKT (SEQ ID NO:82);
F4: RSDNLSQ (SEQ ID NO:52); and
F5: ASNDRKK (SEQ ID NO:53), wherein the protein binds to the target site set forth in SEQ ID NO:124 in an endogenous class 2 transactivator (CTIIA) gene;

(xxvix) F1: RSDDLSR (SEQ ID NO:83);
F2: RNDDRKK (SEQ ID NO:14);
F3: DRSDLSR (SEQ ID NO:17);
F4: RSDHLSE (SEQ ID NO:63); and
F5: ARSTRTN (SEQ ID NO:84), wherein the protein binds to the target site set forth in SEQ ID NO:125 in an endogenous CTIIA gene;

(xxx) F1: TSGNLTR (SEQ ID NO:34);
F2: QSGNLAR (SEQ ID NO:36);
F3: RSDHLTQ (SEQ ID NO:85);
F4: ASMALNE (SEQ ID NO:86); and
F5: TSSNLSR (SEQ ID NO:70), wherein the protein binds to the target site set forth in SEQ ID NO:126 in an endogenous regulatory factor X protein 5 (RXF5) gene;

(xxxi) F1: RSDVLSE (SEQ ID NO:87);
F2: RNQHRKT (SEQ ID NO:88);
F3: RSDHLST (SEQ ID NO:10);
F4: QSSDLRR (SEQ ID NO:20);
F5: RSDNLST (SEQ ID NO:66); and
F6: RSADRKN (SEQ ID NO:89), wherein the protein binds to the target site set forth in SEQ ID NO:127 in an endogenous RXF5 gene;

(xxxii) F1: QSGDLTR (SEQ ID NO:28);
F2: QWGTRYR (SEQ ID NO:90);
F3: ERGTLAR (SEQ ID NO:91);
F4: RSDNLRE (SEQ ID NO:27);
F5: QSGDLTR (SEQ ID NO:28); and
F6: TSGSLTR (SEQ ID NO:51), wherein the protein binds to the target site set forth in SEQ ID NO:128 in an endogenous T-cell receptor alpha (TRAC) gene;

(xxxiii) F1: QSGDLTR (SEQ ID NO:28);
F2: WRSSLAS (SEQ ID NO:92);
F3: QSGDLTR (SEQ ID NO:28);
F4: HKWVLRQ (SEQ ID NO:93); and
F5: DRSNLTR (SEQ ID NO:94), wherein the protein binds to the target site set forth in SEQ ID NO:129 in an endogenous TRAC gene;

(xxxiv) F1: RSDVLSA (SEQ ID NO:67);
F2: DRSNRIK (SEQ ID NO:68);
F3: RSDVLSE (SEQ ID NO:87);
F4: QSGNLAR (SEQ ID NO:36); and
F5: QSGSLTR (SEQ ID NO:95), wherein the protein binds to the target site set forth in SEQ ID NO:130 in an endogenous T-cell receptor beta (TRBC) gene; and (xxxv) F1: RSDHLST (SEQ ID NO:10);
F2: RSDNLTR (SEQ ID NO:74);
F3: DRSNLSR (SEQ ID NO:30);
F4: TSSNRKT (SEQ ID NO:96);
F5: RSANLAR (SEQ ID NO:26); and
F6: RNDDRKK (SEQ ID NO:14), wherein the protein binds to the target site set forth in SEQ ID NO:131 in an endogenous TRBC gene.

2. A fusion protein comprising the engineered zinc finger DNA-binding domain of claim 1 and a transcriptional regulatory domain or a nuclease domain.

3. The fusion protein of claim 2 wherein the transcriptional regulatory domain comprises an activation domain or a repression domain.

4. An isolated cell comprising the fusion protein of claim 2.

5. The fusion protein 2, wherein the nuclease domain comprises a cleavage domain or cleavage half-domain.

6. A polynucleotide encoding the protein of claim 1.

7. A gene delivery vector comprising the polynucleotide according to claim 6.

8. An isolated cell comprising the protein according to claim 1.

9. The isolated cell of claim 8, wherein the cell is selected from the group consisting of a stem cell, a progenitor cell, a T-cell or a Natural Killer (NK) cell.

* * * * *